US008465953B2

(12) United States Patent
Kim et al.

(10) Patent No.: US 8,465,953 B2
(45) Date of Patent: Jun. 18, 2013

(54) ETHANOL PRODUCTION IN NON-RECOMBINANT HOSTS

(75) Inventors: Youngnyun Kim, Oakland, CA (US); Keelnatham Shanmugam, Gainesville, FL (US); Lonnie O. Ingram, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 788 days.

(21) Appl. No.: 12/298,216

(22) PCT Filed: Apr. 26, 2007

(86) PCT No.: PCT/US2007/010306
§ 371 (c)(1),
(2), (4) Date: May 29, 2009

(87) PCT Pub. No.: WO2008/018930
PCT Pub. Date: Feb. 14, 2008

(65) Prior Publication Data
US 2009/0286293 A1    Nov. 19, 2009

Related U.S. Application Data

(60) Provisional application No. 60/796,652, filed on May 1, 2006, provisional application No. 60/848,234, filed on Sep. 29, 2006.

(51) Int. Cl.
*C12P 7/06* (2006.01)
*C12N 9/00* (2006.01)
*C12N 1/20* (2006.01)
*C12N 15/00* (2006.01)
*C07H 21/04* (2006.01)

(52) U.S. Cl.
USPC ..... 435/161; 435/183; 435/252.3; 435/320.1; 436/23.2

(58) Field of Classification Search
None
See application file for complete search history.

(56) References Cited

U.S. PATENT DOCUMENTS 5,916,787 A    6/1999    Ingram et al.

FOREIGN PATENT DOCUMENTS

WO    2005073364 A2    8/2005

OTHER PUBLICATIONS

Accession P0A9P2, published Jul. 21, 1986.*
de Carvalho Lima et al. J Ind Microbiol Biotechnol. Sep. 2002;29(3):124-8.*
EPO Form 1503, May 2, 2011, European Search Report for EP 07 83 5737.
Hasona Adnan et al: "Pyruvate formate lyase and acetate kinase are essential for anaerobic growth of *Escherichia coli* on xylose", Journal of Bacteriology, vol. 186, No. 22, Nov. 2004, pp. 7593-7600 XP002634712, ISSN: 0021-9193.
Nakano M M et al: "Characterization of Anaerobic Fermentative Growth of *Bacillus subtilis*: Identification of Fermentaton End Poducs and Genes Requied for Gowh", Journal of Bacerology, Amercan Sociey for Microbiology, Washington, DC; US, vol. 179, No. 21, Nov. 1, 1997, pp. 6749-6755, XP009000217, ISSN: 0021-9193.
San Martin R et al: "Pathways of Ethanol Production From Sucrose by a Mutant Thermophilic *Bacillus* in Continuous Culture", Journal of General Microbiology, Society for Microbiology, Reading, GB, vol. 139, No. 5, 1 Jan. 1993, pp. 1033-1040, XP001247278, ISSN: 0022-1287.
Causey T B et al: "Engineering the metabolism of *Escherichia coli* W3110 for the conversion of sugar to redox-neutral and oxidized products: Homoacetate production", Proceedings of the National Academy of Sciences of the United States of America, vol. 100, No. 3, Feb. 4, 2003, pp. 825-832, XP002634713, ISSN: 0027-8424.
Stephens P E et al: "Nucleotide Sequence of the Lipoamide Dehydrogenase Gene of *Escherichia coli* K12", European Journal of Biochemistry, Blackwell Publishing, Berlin, De, vol. 135, No. 3, Jan. 1, 1983, pp. 519-528, XP008014488, ISSN: 0014-2956, DOI: DOI: 10.1111/J. 1432-1033. 1983. TB07683.
Kim Youngnyun et al: "Dihydrolipoamide dehydrogenase mutuation alters the NADH sensitivity of pyruvate dehydrogenase complex of *Escherichia coli* K-12", Journal of Bacteriology, vol. 190, Nno. 11, Jun. 2008, pp. 3851-3858, XP002634714, ISSN: 0021-9193.
Wang Qingzhao et al: "Metabolic Flux Control at the Pyruvate Node in an Anaerobic *Escherichia coli* Strain with an Active Pyruvate Dehydrogenase", Applied and Environmental Microbiology, vol. 76, No. 7, Apr. 2010, pp. 2107-2114, XP002634715.
WO-FORM PCT/ISA/210 issued in PCT/US2007/010306, Sep. 26, 2008, ISR.
WO-FORM PCT/ISA/237 issued in PCT/US2007/010306, Sep. 26, 2008, Written Opinion.
Kim, Y. et al. Construction of an *Escherichia coli* K-12 mutant for homoethanologenic fermentation of glucose or xylose without foreign genes. Appl. Environ. Bacteriol. Jan. 2007, vol. 73, No. 6, pp. 1766-1771, see entire document.
Khesghi HS et al. (2000) "The potential of biomass fuels i the context of global climate change: focus on transportation fuels." Ann. Rev. Energy Env. 25:199-244.
Kuyper M. et al. (2005) "Evolutionary engineering of mixed-sugar utilization by a zylosefermenting *Saccharomyces cerevisiae* strain." FEMS Yeast Res. 5:925-934.
Mohagheghi A. et al. (2004) "Performance of a newly developed integrant of *Zymomonas mobilis* for ethanol production on corn stover hydrolysate." Biotechnol. Lett. 26:321-325.

(Continued)

*Primary Examiner* — Christian Fronda
(74) *Attorney, Agent, or Firm* — Edwards Wildman Palmer LLP; Peter F. Corless, Esq.; Richard B. Emmons

(57) ABSTRACT

Non-recombinant bacteria that produce ethanol as the primary fermentation product, associated nucleic acids and polypeptides, methods for producing ethanol using the bacteria, and kits are disclosed.

28 Claims, 21 Drawing Sheets

OTHER PUBLICATIONS

Wyman CE. (2003) "Potential synergies and challenges in refining cellulosic biomass to fuels, chemicals, and power" Biotechnol. Prog. 19:254-262.

Zaldivar J. et al. (2001) "Fuel ethanol production from lignocellulose: a challenge for metabolic engineering and process integration." Appl. Microbiol. Biotechnol. 56:17-34.

* cited by examiner

SEQ ID NO: 1

```
   1 ATGACCGCCGGAGATAAATATATAGAGGTCATGATGAGTACTGAAATCAAAACTCAGGTC
  61 GTGGTACTTGGGGCAGGCCCCGCAGGTTACTTCCGCTGCCTTCCGTTGCGCTGATTTAGT
 121 CTGGAAACCGTAATCGTAGAACGTTACAACACCCCTTGGCGGTGTTTGCCTGAACGTCGGC
 181 TGTATCCCTTCTAAAGCACTGCTGTTCGGCGAACCGAAAACGGTAGCGAAAAGTTATCGACAAGATTCGTACCTGG
 241 GCTGAACACGGTATCGTCTTCGGCGAACCGAAAACGGATATCGACAAGATTCGTACCTGG
 301 AAAGAGAAAGTGATCAATCAGCTGGTAAATTCACCGGGGCTAACACCCTGGAAGTTGAAGGT
 361 GTCAAAGTGGTCAACGGTCTGGTAAATTCACCGGGGCTAACACCCTGGAAGTTGAAGGT
 421 GAGAACGGCAAAACCGTGATCAACTTCGACAACGGATCATTGCAGCGGGTTCTCGCCCG
 481 ATCCAACTGCCGTTTATTCGCATGGAAGATCCCGGTATCGTGGACTCCACTGACGCGCTG
 541 GAACTGAAAGAAGTACCAGAACGCCTGCTCGGTAATGGGTGGCGTATCATCGGTCTGAAA
 601 ATGGGCACCGTTTACCGCGAGCTGACAAAGACATCGTTAAAGTCTTCACCAAGCGTATCAGCGAAGAAA
 661 GTTATCCCGGCAGCTGACAAAGACATCGTTAAAGTCTTCACCAAGCGTATCAGCGAAGAAA
 721 TTCAACCTGATGCTGGAAACCAAAGTTACCGCCGTTGAACGCCAGCGTTACGACGCCGTGCTGTA
 781 GTGACGATGGAAGGCAAAAAGCACCCGGTAAAAACCTCGACGCAGCCAAAGCAGGCGTGGAAGTT
 841 GCGATTGGTCGTGTGCGAACGGTAAAAACCTGACAAACGATGCTGGCATACAAAGGTGTTCAGAAGGTCAC
 901 GACGACCGTGGTTTCATCCGGTGACAACGATGCTGGCATACAAAGGTGTTCAGAAGGTCAC
 961 GCTATCGGCGATATCGTCGGTGAAGTTATCGCCGGGTAAGAACACTACTTCGATCGGAAGTTATCCGCC
1021 GTTGCCGATGAAGTTATCGCCGGGTAAGAACACTACTTCGATCGACTGGGTCTGAGAAGAAGCGAAAGAG
1081 ATCGCCTATACCGAACAGAAGTTGCATGGTGGCTGAGAAGAAGCGAAAGAG
1141 AAAGGCATCAGCTATGAAACCGCCACCTTCCGGTGCATGCTTCTGGTCGTGCTATCGCT
1201 TCCGACTGCCAGACGGTATGACCAAGCTGATTTTCGACAAAGAATCACCGTGTGATC
1261 GGTGGTGCATTGTCGGTTACTAACGGCGGCGAGCTGCTGGGTGAAATCGGCCTGCAATC
1321 GAAATGGGTTGTGATGCTGAAGACATCGCACTGACCATCCACGCCACCGACTCTGCAC
1381 GAGTCTGTGGGCCTGGCCGGCAGAAGTGTTCGAAGGTAGCATTACCGACCTGCCGAACCCG
1441 AAAGCGAAGAAGAAGTAA 1458
```

Figure 1 (A)

SEQ ID NO: 2

```
  1 MSTEIKTQVV VLGAGPAGYS AAPRCADLGL ETVIVERYNT LGGVCLNVGC IPSKALLHVA KVIEEAKALA EHGIVFGEPK TDIDKIRTWK EKVINQLTGG
101 LAGMAKGRKV KVNGLGKFT GANTLEVEGE NGKTVINFDN ALIAAGSRPI QLPFIPHEDP RIWDSTDALE LKEVPERLLV MGGGIIGLEM GTVYHALGSQ
201 IDVVEMFDQV IPAADKDIVK VFTKRISKKF NLMLETKVTA VEAKEDGIYV TMEGKKAPAE PQRYDAVLVA IGRVPNGKNL DAGKAGVEVD DRGFIRVDKQ
301 LRTNVPHIFA IGDIVGQPML AYKGVHEGHV AAEVIAGKKH YFDPKVIPSI AYTEPEVANV GLTEKERAKEK GISYETATFP WAASGRALAS DCADGMTKLI
401 FDKESHRVIG GAIVGTNGGE LLGEIGLAIE MGCDAEDIAL TIHAHPTLHE SVGLAAEVFE GSITDLPNPK AKKK
```

Figure 1 (B)

SEQ ID NO: 3

```
   1 ATGACCGCCGGAGATAAATATATAGAGGTCATGATGAGTACTGAAATCAAAACTCAGGTC
  61 GTGGTACTTGGGCAGGCCCCGCAGGTTACTCCGCTGCCTTCCGTTGCGCTGATTTAGGT
 121 CTGGAAACCGTAATCGTAGAACGTTACAACACCCTTGGCGGTGTTTGCTGAACGTCGGC
 181 TGTATCCCTTCTAAAGCACTGCTGCACGTAGCAAAGTTATCGAAGAAGCCAAAGCGCTG
 241 GCTGAACACCGTATCGTCTTCGGCGAACGAAAACGATATCGACAAGATTCGTACCTGG
 301 AAAGAGAAAGTGATCAATCAGCTGAACCGGTGGTCTGGCTGTATGGCGAAAGGCCGCAAA
 361 GTCAAAGTGGTCAACGTCTGGTAAATTCACCGGGCGATCATTCAGCGCGGGTTCTCGCCG
 421 GAGAACGGCAAAACCGTGATCAACTTCGACAACGCGATCATTGGGGACTCCACTGACGCTG
 481 ATCCAACTGCCGTTTATTCCGCATGAAGATCCGTATGGGTGGCGGTATCATCGGTCTGAA
 541 GAACTGAAAGAAGTACCAGAACGCTGGGTTCACAGATTGACGTGGTTGAAATGTTGACCAG
 601 ATGGGCACCGTTTACCACGCGTGGGTTCACAGATTGACGTGGTTGAAATGTTCGACCAG
 661 GTTATCCCGGCAGTCGACAAAGACATCGTTAAAGTCTTGACGCGTATTACCAAGCGTATATCAGCAAGAAA
 721 TTCAACCTGATGCTGGAAACCAAAGTTACCGCCGTTGAAGCGAAAGAAGACGCCATTAT
 781 GTGACGATGGAAGGCAAAAAGCACCCGCTGAACCGGTAAAAACCTGCGTTACGACGCCGTGCTGGTA
 841 GCGATTGGTCGTGTGCCGAACGGTAAAAACCTGACAAACAGCTGCGTACCAACGTACCGCACATCTTT
 901 GACGACCGTGGTTTCATCGCGTTGCAACCGATGCTGGCACACAAAGGTGTTCACGAAGGTCAC
 961 GCTATCGGCGATATCGTCGGTGCTGAAGTTACTGCCGCTGAAGTTATCCGTCC
1021 GTTGCCGCTGAAGTTATCGCCGTAAGAACACTACTTCGATCCGAAAGTTATCCGTCC
1081 ATCGCCTATACCAAACCAGAAGTTGCATGGTGGTCTGACTGAGAAGAAGCGAAAGAG
1141 AAAGGCATCAGCTATGAAACCGCCACCTTCCCGGGCGCTCTTCCGTCGTCTATCGCT
1201 TCCGACTGCGCAGACGGTATGACCAAGCTGATTTTCGACAAAGAATCTCACCGGTGATC
1261 GGTGGTGCGATTGTCGGTACTAACGGCGGCAGCTGCTGGGTGAAATCGGCCTGGCAATC
1321 GAAATGGGTTGTGATGCTGAAGACATCGCACTGACCATCGACGCCACCCGACTCTGCAC
1381 GAGTCTGTGGGCCTGGGCGGCAGAAGTGTTCGAAGGTAGCATTACCGACCTGCCGAACCCG
1441 AAAGCGAAGAGAAGTAA    1458
```

Figure 2 (A)

SEQ ID NO: 4

```
  1 MSTEIKTQVV VLGAGPAGYS AAFRCADLGL ETVIVERYNT LGGVCLNVGC IPSKALLHVA KVIEAKALA  EHGIVFGEPK TDIDKIRTWK EKVINQLTGG
101 LAGMAKGRKV KVVNGLGKFT GANTLEVEGE NGKTVINFDN AIIAAGSRPI QLPFIPHEDP RIWDSTDALE LKEVPERLLV MGGGIIGLEM GTVYHALGSQ
201 IDVVEMFDQV IPAADKDIVK VPTKRISKKF NLMLETKVTA VEAKEDGIYV TMEGKKAPAE PQRYDAVLVA IGRVPNGKNL DAGKAGVEVD DRGPIRVDKQ
301 LRTNVPHIFA IGDIVGQPML AHKGVHEGHV AAEVIAGKKH YFDPKVIPSI AYTKPEVAWV GLTEKEAKEK GISYETATFP WAASGRAIAS DCADGMTKLI
401 FDKESHRVIG GAIVGTNGGE LLGEIGLAIE MGCDAEDIAL TIHAHPTLHE SVGLAAEVFE GSITDLPNPK AKKK
```

Figure 2 (B)

SEQ ID NO: 5

W3110

```
   1 ATGACCGCCGAGATAATATATAGAGGTCATGATGAGTACTGAAATCAAAACTCAGGTC
  61 GTGGTACTTGGGCAGGCCTGATCGTTACTCAACAACCCTTGGCGGTGTTTGCCTGAACGTCGGC
 121 CTGGAAACCGTAATCGTAGAACGTTACAACACCCTTGGCGGTGTTTGCCTGAACGTCGGC
 181 TGTATCCCTTCTAAAGCACTGCTGCACGTAGCAACCGAAAACCGATATCGAAGATTCGTACCTGG
 241 GCTGAACACGGTATCGTCTTCGGCGAACCGAAAACCGAAAACCGATATCGTGGCTGTGTGCAAA
 301 AAAGAGAAAGTGATCAATCAGCTGACTGGGTAAATTCAGACGGGGCTAACACCCTGGAAGTTGAAGGT
 361 GTCAAAGTGGTCAAACGGTCTGGGTAAATTCACGGGGCTAACACCCTGGAAGTTGAAGGT
 421 GAGAACGGCAAAACCGTGATCAACTTCGACAACGCGATCATTCGGACTCCACTGACGCGTG
 481 ATCCAACTGCCGTTTATTCCGCATGAAGATCCCGTAATGGTGGCGTATCATCGGTCTGAAA
 541 GAACTGAAAGAAGTACCAGAACGCCTGGGTTCACAGATTGACGTGGTTGAAATGTTCGACCAG
 601 ATGGGCACCGTTTACGCAGTCGACAAAGACATCGTTAAAGTCTTACCGCCGTTGAAGCGTATCAGCAAGAAA
 661 GTTATCCCGGCAGCTGACAAAGACATCGTTAAAGTCTTACCGCCGTTGAAGCGTATCAGCAAGAAA
 721 TTCAACCTGATGCTGAAGAAGCAAAAGCACCCGTGAACCGCTGAACGGTAAAACCTCGACGCCGTGCTGTA
 781 GTGACGATGGAAGCAAAAGCACCCGTGAACGGTAAAACCTCGACGCCGTGCTGTA
 841 GCGATTGGTCGTGTGCCGAACGGTAAAACCTCGACAAACAGCTGCGTACCAACGTGCCACATCTTT
 901 GACGACCGTGGTTTCATCCGCTGGTCAACCGATGCTGGCACACAAGGTGTTCAGAAGGTCAC
 961 GCTATCGGCGATATCGTCGGTCAACCGATGCTGGCACACAAGGTGTTCAGAAGGTCAC
1021 GTTGCCGCTGAAGTTATCCGGTAAGAACACTACTTCGATCGAAAGTTATCCCGTCC
1081 ATCGCCTATACCGAACCAGAGTTGCATGGTGGTCTGACTGGGTCGAGAAGAAGCGAAAGAG
1141 AAAGGCATGCATGAAACCGCCACCTTCCCGTGGGCTGCTTCTGGTCGTCGTATCGCT
1201 TCCGACTGCGCAGACGTATGACCAAGCTGATTTCGACAAAGAATCTCACCGTGTGAT
1261 GGTGGTGCGATTGTCGGTACTAACGGCGGAGCTGCTGGGTGAATCGCCTGGCAATC
1321 GAAATGGTTGTGATGCTGAAGACATCGACCATCCACGCCACCGACTCTGCAC
1381 GAGTCTGTGGGCCTGGGCCGAGAAGTGTTCGAAGGTAGCATTACCGACCTGCCGAACCCG
1441 AAAGCGAAGAAGAAGTAA    1458
```

Figure 3 (A)

SEQ ID NO: 6

N3110 (wt)

```
  1 MSTEIKTQVV VLGAGPAGYS AAFRCADLGL ETVIVERYNT LGGVCLNVGC IPSKALLHVA KVIEEAKALA EHGIVFGEPK TDIDKIRTWK EKVINQLTGG
101 LAGMAKGRKV KVNGLGKFT GANTLEVEGE NGKTVINFDN AIIAAGSRPI QLPFIPHEDP RIWDSTDALE LKEVPERLLV MGGGIGLEM GTVYHALGSQ
201 IDVVEMFDQV IPAADKDIVK VFTKRISKKF NLMLETKVTA VEAKEDGIYV TMEGKAPAE PQRYDAVLVA IGRVPNGKNL DAGKAGVEVD DRGFIRVDKQ
301 LRTNVPHIFA IGDIVGQPML AHKGVHEGHV AAEVIAGKKH YFDPKVIPSI AYTEPEVAWV GLTEKEAKEK GISYETATFP WAASGRAIAS DCADGMTKLI
401 FDKESHRVIG GAIVGTNGGE LLGEIGLAIE MGCDAEDIAL TIHAHPTLHE SVGLAAEVFE GSITDLPNPK AKKK
```

Figure 3 (B)

```
PdhR W3110   MAYSKIRQPK LSDVIEQQLE FLILEGTLRP GEKLPPEREL AKQFDVSRPS LREAIQRLEA  60
PdhR SE2378  MAYSKIRQPK LPDVIEQQLE FLILEGTLRP GEKLPPEREL AKQFDVSRPS LREAIQRLEA  60

PdhR W3110   KGLLLRRQGG GTFVQSSLWQ SFSDPLVELL SDHPESQYDL LETRHALEGI AAYYAAL-RS 119
PdhR SE2378  KGLLLRRQGG GTFVQSSLWQ SFSDPLVELL SDHPESQYDL LETRHALEGI AAYYAALLRS 120

PdhR W3110   TDEDKERIRE LHHAIELAQQ SGDLDAESNA VLQYQIAVTE AAHNVVLLHL LRCMEPMLAQ 179
PdhR SE2378  TDEDKERIRE LHHAIELAQQ SGDLDAESNA VLQYQIAVTE AAHNVVLLHL LRCMEPMLAQ 180

PdhR W3110   NVRQNFELLY SRREMLPLVS SHRTRIPEAI MAGKPEEARE ASHRHLAFIE EILLDRSREE 239
PdhR SE2378  NVRQNFELLY SRREMLPLVS SHRTRIPEAI MAGKPEEARE ASHRHLAFIE EILLDRSREE 240

PdhR W3110   SRRERSLRRL EQRKN 253
PdhR SE2378  SRRERSLRRL EQRKN 254
```

Figure 6A

```
W3110   AACGAAAGAA TTAGTGATTT TTCTGGTAAA AATTATCCAG AAGATGTTGT AAATCAAGCG  60
SE2378  AACGAAAGAA TTAGTGATTT TTCTGGTAAA AATTATCCAG AAGATGTTGT AAATCAAGCG  60

W3110   CATATAAAAG CGCGGCAACT AAACGTAGAA CCTGTCTTAT TGAGCTTTCC GGCGAGAGTT 120
SE2378  CATATAAAAG CGCGGCAACT AAACGTAGAA CCTGTCTTAT TGAGCTTTCC GGCGAAAGTT 120

W3110   CAATGGGACA GGTTCCAGAA AACTCAACGT TATTAGATAG ATAAGGAATA ACCCATGTCA 180
SE2378  CAATGGGACA GGTTCCAGAA AACTCAACGT TATTAGATAG ATAAGGAATA ACCCATGTCA 180

W3110   GAACGTTTCC CAA 193
SE2378  GAACGTTTCC CAA 193
```

Figure 6B

Figure 8
A. Ethanologenic organisms
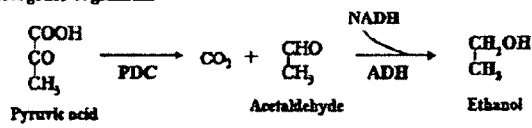
B. Native Pathway for Ethanol Production in *E. coli*
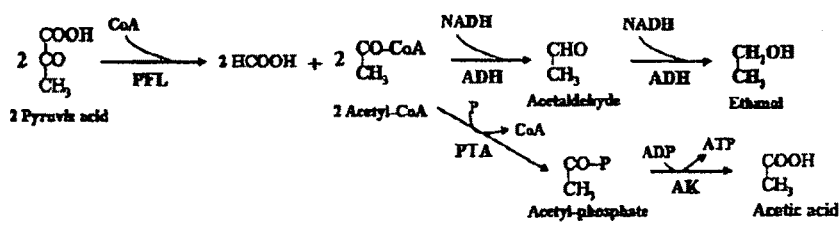
C. Proposed Pathway for Ethanol Production in *E. coli* Strain SE2378
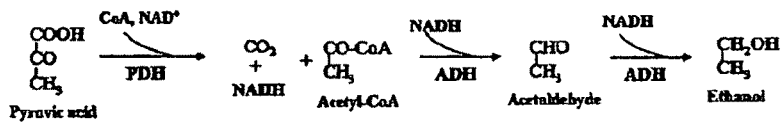

```
Clostridium tetani E88                              MNFKKTIAILLIRIAMVFKIC

```
Clostridium tetani E88                              AKKSELKLSLECDVAILGAGPGG-YVAAIQAAKLGAKVVIVEKD-KVGGTCLNRGCIPTKA 178
Thermoanaerobacter ethanolicus                      HSKRRIK-MDYDVIVLGGGPGG-YTAAIRSELGKKVAVVEEY-SLGGTCLNRGCIPTEV  79
Bacillus cereus ATCC 10987                          -MVVGDFPIELDTVVVGAGPGG-YVAAIRAAQLGQKVAIIEKA-NLGGVCLNVGCIPSKA  57
Lactobacillus plantarum WCFS1                       -MVVGDFAEERDTMIIGAGPGG-YVAAIRAAELGQKVTVEKE-YIGGVCLNVGCIPSKA   57
Lactococcus lactis subsp. cremoris SK11             -MVVGAQATEVDLVIIGSGPGG-YVAAIRAAELGKKVTIEKD-NVGGVCLNIGCIPSKA   57
Oenococcus oeni MCW PSU-1                           GGVGAQATDIDTVVIGSGPGG-YVAAIRAAELGQKVTIIEST-FIGGVCLNVGCIPSKA   61
Escherichia coli K12 MG1655                         ----MSTEIKTQVVVLGAGPAG-YSAAFRCADLGLETVIVERYNTLGGVCLNVGCIPSKA  55
Salmonella typhimurium LT2                          ----MSTEIKTQVVVLGAGPAG-YSAAFRCADLGLETVIVERYNTLGGVCLNVGCIPSKA  55
Vibrio fischeri ATCC 700601                         ----MSKQVKAQVVVLGSPAG-YSAAFRCADLGLETVLIERYSTLGGVCLNVGCIPSKA   55
Shewanella sp. ANA-3                                ----MSNEIKTQVVVLGAGPAG-YSAAFRAADLGLETVIVERFSTLGGVCLNVGCIPSKA  55
Pseudomonas aeruginosa PAO1 ATCC15692               ----MMESYDVIVIGAGPGG-YNAAIRAGQLGLKVACVEGRETLGGTCLNVGCMPSKA    53
Rhodobacter sphaeroides 2.4.1                       ----MATFDVIIIGAGPGG-YVSAIRCAQLGLKTAVVEGREALGGTCLNVGCIPSKA     52
Geobacter metallireducens GS-15                     ----------------------VEKRSALGGVCLNEGCIPSKA                  21
Acinetobacter sp. ADP1                              ----FDLVVIGAGPGG-YVAAIRAAQLGLKTAIVEAT-HLGGICLNWGCIPTKA        55
Gluconobacter oxydans 621H                          ----FDLIVGGGPGG-YVAALRASQLGMSVALVEST-HFGGVCLNWGCIPTKA         52
Corynebacterium glutamicum DSM20300                 ----YDVVVLGAGPGG-YVSAIRAAQLGKKVAVIEKQ-YWGGVCLNVGCIPSKS        52
Lactobacillus casei ATCC334                         ----DLVVLGGGPGG-YVAAIRAAQLGMQVVLVEKA-KVGGICLHKGCIPTKS         52
Streptomyces coelicolor M145/A3(2)                  PDVANDASTVFDLVILGGSGG-YAAALRGAQLGLDVALIEKN-KLGGTCLHNGCIPTKA   80
Streptococcus mutants ATCC 700610                   AQKTPLADDEYDMIVVGGGPAG-YYAAIRGAQLGGMVAIVEKS-EFGGTCLNKGCIPTKT 172
Methanosarcina barkeri Fusaro                       ----VENYDLIIIGTGSAMNYINPILDSNLKMFVAVIDKD-EPGGICLTRGCIPSKI    52
                                                                                                        ::   **   **.:*.:.*

Clostridium tetani E88                              FVRSSEVYSNVKNSE------KYGISLENFSIDIKKVVARKD-NIVDKLVGGIQYLIQKHN 232
Thermoanaerobacter ethanolicus                      YSHAAELINAIKDAK-----DFGIMAQY-AVDIAKLRQKKE-RVVKRLVGGVGYLMNLHH 132
Bacillus cereus ATCC 10987                          LINAGHRYENAMHSD-----DMGIT-AENVKVDFTKVQEWKN-GVVKKLTGGVEGLLKGNK 111
Lactobacillus plantarum WCFS1                       LISAGHRLQEAKDSK-----IFGIKNIQDPVLDFKVTQDMKDHQVVDRLITGGVEMLLKKHE 113
Lactococcus lactis subsp. cremoris SK11             LINICHHYQESLEEKGENPFGLS-VGNVKLNWESAQKWKQDKVVNQLTGGVKMLLKKHH 116
Oenococcus oeni MCW PSU-1                           LINVSHHYHDAVSEQ-----PFGLK-SSGTELDWKTTQEWKQKKVVNQLTGGVEMLLKKHR 116
Escherichia coli K12 MG1655                         LLHVAKVIEEAKALA-----EHGIV-FGEPKTDIDKIRTWKE-KVINQLTGGLAGMAKGRK 109
Salmonella typhimurium LT2                          LLHVAKVIEEAKALA-----EHGIV-FGEPKTDIDKIRTWKE-KVITQLTGGLAGMAKGRK 109
Vibrio fischeri ATCC 700601                         LLHVSKVIEEAKAMA-----EHGVV-FGEPQTDINKIRIWKD-KVTQLTGGLGGMAKMRN 109
Shewanella sp. ANA-3                                LLHVAKVIEEAKAVA-----AHGVV-EGEFPTIDLDKLRSFKQ-KVISQLTGGLGGNSKMRK 109
Pseudomonas aeruginosa PAO1 ATCC15692               LLHABELYAARSGGE-----FARLGIR-VSPELDLAQMMKQKD-ESVAALTRGVEFLPKKH 108
Rhodobacter sphaeroides 2.4.1                       LLHATHNLHEVHEM------FEKMGLMGAHPTVDMSKMQGYKQ-EVVDGNTKGIEFLEKKNK 107
Geobacter metallireducens GS-15                     LDSSELFALARDR-------PAGHGIAIDPPRLDLAPMMARKD-DVVKKLTDGVAFIFKKNK  76
Acinetobacter sp. ADP1                              LLAGELAHQFWHAS------QFGFELGDINFDLSKLVQHSR-QVSAQLVQGIEHLLRKMQ 109
Gluconobacter oxydans 621H                          LLRSSEIHHLLHELG-----TFGLSADNISFDLSKIVGRSR-SIARRNGGGIAHLLKKTK 106
Corynebacterium glutamicum DSM20300                 LIKNAEVAHTFTHEKK-----TFGIN-GEVTFNYEDAHKRSR-GVSDKIVGGVHYLMKKNK 106
Lactobacillus casei ATCC334                         LLHSGETLRLMQSAAT----FGGIIEGKVGIDFAKIQARKA-TVVDQLYRGVQGLMKKNK 107
Streptomyces coelicolor M145/A3(2)                  LLHAGEVADQSRESEQ-----FG-VKTSFEGVDMAGVHKYKD-EVIAGLYKGLQGLVASRK 134
Streptococcus mutants ATCC 700610                   YLKNAEILDGIKIAAG----RGINFASTNYTIDMDKTVAFKD-TVVKTITSGVQGLLKANK 228
Methanosarcina barkeri Fusaro                       LLYPAELIPEIETAS------IFGIMLEIKDIDFLAIMEMRPKSGEDIEAIRKSLTDDPY 107
```

| Organism | Sequence | # |
|---|---|---|
| Clostridium tetani E88 | KNIMGKDIQID--YSAVPSVIFTEPEIAVVGVCEKIAK---ENNLDVEVGKFPFSANGKA | 508 |
| Thermoanaerobacter ethanolicus | HNIAGEEKEAD--LSIVPNCLYTNPEIAWAGLNEVQAR---EKFGDVKIGTFPYTALGRA | 399 |
| Bacillus cereus ATCC 10987 | EAISGHASAID--YIGIPAVCFTDPELASVGYTKKQAE---EAGMTVVSKFPFAANGRA | 389 |
| Lactobacillus plantarum WCFS1 | GALSGKKTAND--YVSIPAVCFTDPELATVGMTKAEAE---EAGLQVTSKFPFAGNGRA | 391 |
| Lactococcus lactis subsp. cremoris SK11 | AAIAGAEDDVDL-HVALPAVAYTTELATVGETPESVK---DPK-DVKISKFPFAANGRA | 393 |
| Oenococcus oeni MCW PSU-1 | AAISGDQNAHDL-HYSLPAVAYTNYELATIGETPESVK---EKKLDAKAYKFPFAANGRA | 394 |
| Escherichia coli K12 MG1655 | EVIAGKKHYFD--PKVIPSIAYTEPEVAWVGLTEKEAK---EKGISYETATFPWAASGRA | 387 |
| Salmonella typhimurium LT2 | EVIAGKKHYFD--PKVIPSIAYTEPEVAWVGLTEKEAK---EKGISYETATFPWAASGPA | 387 |
| Vibrio fischeri ATCC 700601 | EVISGKKHYFD--PKVIPSIAYTEPEVAWVGKTEKEAK---EEGLNFEVATFPWAASGRA | 386 |
| Shewanella sp. ANA-3 | EVIAGMKHYFD--PKVIPSIAYTDPEVAWVGLTEKEAK---EQGIAYETATFPWAASGRA | 388 |
| Pseudomonas aeruginosa PAO1 ATCC15692 | ERIAGHAAEMN--AEVIPSVIYTQPEVASVGLGEEQLQ---AARREYKVGRFPFSANSRA | 388 |
| Rhodobacter sphaeroides 2.4.1 | EILAGKHGHVN--YGVIPGVIYTTPEVASVGRTEESLK---EEGRAYKVGKFPFMGNAPA | 383 |
| Geobacter metallireducens GS-15 | ERLTGQASVVD--YAYIPGIVYTWPEAAGVGRTEEELK---TEGVEYKVGKFPFMANGRA | 365 |
| Acinetobacter sp. ADP1 | EKIAGIADVHPLNRLQIPGCIFTHPQVASIGLTEQQAKAEG---KQIHIGKFPMSANGKA | 389 |
| Gluconobacter oxydans 621H | EKIAGRS-PQELHPLNIPGCTYSRPQIASVGLSEEKAIAAG---HKVKVGRFPFIANGKA | 389 |
| Corynebacterium glutamicum DSM20300 | ETJAGAETQTLGDYMMAPRATFCNPQVSSFGYTEEQAKEKWPD-REIKVASFPFSANGKA | 390 |
| Lactobacillus casei ATCC334 | EHRAGLP-VAPLNYNDVPRCTYTDPEIASVGYTSS----NYPQDRDVKIGRFNFNANAKA | 392 |
| Streptomyces coelicolor M145/A3(2) | ERLAGLK-TVFVDYDGVPRVTYCHPEVASVGLTEARAKEVYGADKVVSI-KFPLGGNGKS | 407 |
| Streptococcus mutants ATCC 700610 | ENAIWGNVRXAN-LKYTPAAVYTHPEVAMCGITEEQAR---QEYGNVLVGKSSFSGNGRA | 497 |
| Methanosarcina barkeri Fusaro | NAILKEKAKAD--YHAVPHAVFSYPEIAG VGMREQEAVEK-YGEERILIGLKFFEDTAKG | 386 |

| Organism | Sequence | # |
|---|---|---|
| Clostridium tetani E88 | LTILGEDRGFIKVIKEKATGKVVGASIIGAHASDLIAELI-LAVKNGLTSEQIAETIHAHP | 567 |
| Thermoanaerobacter ethanolicus | MTMGQNDGFVKIIAEEAKYNRVVGMEIIGAGATEIIHEGV-LAIKEEFTLEELADAIHAHP | 458 |
| Bacillus cereus ATCC 10987 | LSINSTDGF-QLVTRKEDGLLVGAQVAGAGASDIISEIG-LAIEAGMTAEDIAQTIHAHP | 448 |
| Lactobacillus plantarum WCFS1 | ISINAMDGFFRLVSTKDEGTIVGAQIAGPGASDLISELS-VAVNGGMNVEDLALTIHPHP | 450 |
| Lactococcus lactis subsp. cremoris SK11 | ISMNDTTGFLRLJITETKEGALIGAQIVGPGASDLISGLS-LAIENGLTSKDISLTIQPHP | 452 |
| Oenococcus oeni MCW PSU-1 | LSINEGKGFIRLISDNQTKALIGSQIVGPGASDLISELS-LAIEMGLTTEDISLTIHPHP | 453 |
| Escherichia coli K12 MG1655 | IASDCADGMTKLIFDKESHRVIGGAIVGTNGGELLGEIG-LAIEMGCDAEDIALTIHAHP | 446 |
| Salmonella typhimurium LT2 | IASDCADGMTKLIFDKESHRVIGGAIVGTNGGELLGEIG-LAIEMGCDAEDIALTIHAHP | 446 |
| Vibrio fischeri ATCC 700601 | IASDCADGMTKLIFDKETHRVIGGAIVGTNGGELLGEIG-LAIEMGCDAEDIALTIHAHP | 445 |
| Shewanella sp. ANA-3 | IASDCSEGMTKLIFDKDTHKVIGGAIVGVNGGELLGEIG-LAIEMGCDAEDIALTIHAHP | 447 |
| Pseudomonas aeruginosa PAO1 ATCC15692 | KINHESEGFIKILSDARSDQVLGVHMIGPGVSEMIGEAC-VAMEFSASAEDLALTCHPHP | 447 |
| Rhodobacter sphaeroides 2.4.1 | KAVFQAEGFVKMIADKETDRILGCBIIGPAAGDLIHEVC-VAMEFGASAQDLAMTCHAHP | 442 |
| Geobacter metallireducens GS-15 | KCMDETEGFVKILATPDTGRVLGIHVIGPRASDVIAEAV-TVMTYGGSAADIAMTFHAHP | 424 |
| Acinetobacter sp. ADP1 | IALGQTAGFVKTIVDVESGELLGAHMVGHEVTEQIQGYA-IAQALEATDEHLAQVIFPHP | 448 |
| Gluconobacter oxydans 621H | VAMGETDGMVKTVFDATSGELLGAHMIGAEVTEMIQGYV-ITRTGELTEARLVETVFPHP | 448 |
| Corynebacterium glutamicum DSM20300 | VGLAETDGFAKIVADAEFGELLGAHLVGANASELINELV-LAQNWDLTTEISRSVHIHP | 449 |
| Lactobacillus casei ATCC334 | IILGDTAGFVEVLRDVITDDIIGVSIIGAHATDMIAEMS-DAMYLDASATEIGDAVHPHP | 451 |
| Streptomyces coelicolor M145/A3(2) | RIL-KTAGEIKLVQ-VKDGAVVGVHMVGDRMGEQVGEAQ-LIYNWEALPAEVAQLIHAHP | 464 |
| Streptococcus mutants ATCC 700610 | IASMEAQGFVKVVADAKYHEILGVHIIGPAAAEMINEAS-TIMENELTVDELLRSIHGHF | 556 |
| Methanosarcina barkeri Fusaro | SAMEIRDYFVKVILDSEEEKIIGAHIIGPHASVLIHQIIPLMYTESRSPEPIMRGMDIHP | 446 |

Figure 9 (5/6)

| Organism | Sequence | Position |
|---|---|---|
| Clostridium tetani E88 | TTAEVVHEASLAVEGGALHFAE--------------------- | 589 |
| Thermoanaerobacter ethanolicus | TLSESVKEAAEDALGMPINKG---------------------- | 479 |
| Bacillus cereus ATCC 10987 | TLGEITMERAEVALGMPIHIVK---------------------- | 470 |
| Lactobacillus plantarum WCFS1 | TLGEVVQERADEAMGYPTHI----------------------- | 470 |
| Lactococcus lactis subsp. cremoris SK11 | TLGEAIMDTAELADGLPIHV---------------------- | 472 |
| Oenococcus oeni MCW PSU-1 | TLGEAIMDASELADGLPIHI----------------------- | 473 |
| Escherichia coli K12 MG1655 | TLHESVGLAAEVFEGSITDLPNPKAKKK--------------- | 474 |
| Salmonella typhimurium LT2 | TLHESVGLAAEVFEGSITDLPNPKAKKK--------------- | 474 |
| Vibrio fischeri ATCC 700601 | TLHESVGLAAEVTEGSITDLPNKKAVKKKK------------- | 475 |
| Shewanella sp. ANA-3 | TLHESVGLAAEIYEGSITDLPNPKAKKK--------------- | 475 |
| Pseudomonas aeruginosa PAO1 ATCC15692 | TRSEALHQAAMDVHGRAMQN----------------------- | 467 |
| Rhodobacter sphaeroides 2.4.1 | TWSEAVREAALACGDGAIHA----------------------- | 462 |
| Geobacter metallireducens GS-15 | TLAEAMKEAALDVEKRAIHATRRFPWEKISQPRSSKRTSRRASLSRAPRSPR | 476 |
| Acinetobacter sp. ADP1 | TLSEAMHESILASMQRAIHI---------------------- | 468 |
| Gluconobacter oxydans 621H | TISETMHEATLAAFDGPLHI---------------------- | 468 |
| Corynebacterium glutamicum DSM20300 | TLSEAVKEAAHGISGHMINF---------------------- | 469 |
| Lactobacillus casei ATCC334 | TLSEAIQEATLDTHKIAIHK---------------------- | 471 |
| Streptomyces coelicolor M145/A3(2) | TQNEALGEAHLALAGKPLHMHD--------------------- | 486 |
| Streptococcus mutans ATCC 700610 | TFSEVMYEAFADVLGEAIHNPPKPR------------------- | 581 |
| Methanosarcina barkeri Fusaro | SLSEVVTRAFYSRLPPEHYHHFLKHIGLED-------------- | 476 |

Figure 9 (6/6)

ETHANOL PRODUCTION IN NON-RECOMBINANT HOSTS

RELATED APPLICATION

This application is the U.S. national phase, pursuant to 35 U.S.C. §371, of PCT international application Ser. No. PCT/US2007/010306, filed Apr. 26, 2007, designating the United States and published in English on Feb. 14, 2008 as publication WO 2008/018930 A2, which claims priority to U.S. provisional application Ser. Nos. 60/796,652, filed May 1, 2006 and 60/848,234, filed Sep. 29, 2006. The entire disclosures of the aforementioned patent applications are incorporated herein by this reference.

GOVERNMENT SPONSORED RESEARCH

This work was supported, in part, by Grant No. DE-FG36-04GO14019 from the U.S. Department of Energy. Accordingly, the government has certain rights to the invention.

BACKGROUND OF THE INVENTION

Ethanol is an attractive alternate transportation fuel to replace at least a part of petroleum (Kheshgi, et al., 2000, Wooley, et al., 1999). Although ethanol is currently produced in the U.S. by fermenting glucose from cornstarch using *Saccharomyces cerevisiae* (Bothast, et al., 2005), expanding this process to produce a large fraction of the automotive fuel requirement would adversely impact the food and feed industry.

Lignocellulosic biomass is an attractive alternative feedstock that can be fermented to ethanol after appropriate pretreatment without impacting food and feed supply (Wyman, et al., 2003, Zaldivar, et al., 2001). In contrast to cornstarch, biomass contains significant amounts of pentose sugars that are recalcitrant to fermentation by yeast.

Conversion of complex sugars to ethanol requires microbial biocatalysts that effectively ferment both hexose and pentose sugars. Towards this goal, recombinant organisms have been developed in which heterologous genes were added to platform organisms such as yeasts, *Z. mobilis* and *E. coli*. For example, recombinant ethanologenic *Escherichia coli* containing the pdc and adh genes from *Zymomonas mobilis* ferment both hexoses and pentoses to ethanol at high rate and yield (Ingram, et al., 1999). In addition, genetic engineering of yeast and *Z. mobilis* by adding genes for pentose utilization has yet to yield a biocatalyst that matches the pentose fermentation characteristics of the recombinant ethanologenic *Escherichia coli* (Kuyper, et al., 2005, Mohagheghi, et al., 2004).

SUMMARY OF THE INVENTION

As noted above, conversion of lignocellulosic feedstocks to ethanol requires microbial biocatalysts that effectively ferment both hexose and pentose sugars. Such microbial biocatalysts include recombinant organisms in which heterologous genes were added to platform organisms such as yeasts and bacteria, e.g., *Zymomonas mobilis* and *Escherichia coli*.

However, the use of a recombinant organism for large-scale fuel production is perceived by some as a barrier to commercialization. Development of a non-recombinant ethanologen may reduce one of the perceived barriers to commercial ethanol production from lignocellulosic substrates.

Accordingly, the invention is based, at least on part, on the discovery of a mutation that redirects glycolysis via a homoethanol pathway in microorganisms that are otherwise non-ethanologenic and the development of non-recombinant ethanologenic microorganisms that ferment glucose and xylose to ethanol under anaerobic conditions based on that discovery. In particular, the pdh operon has been identified as the origin of the homoethanol pathway. More specifically, the lpd gene within the pdh operon has been identified as responsible for homoethanol fermentation by, e.g., *E. coli* under anaerobic conditions.

Thus, in one aspect, the invention provides an isolated non-recombinant bacterium comprising a mutation, wherein the mutation renders the non-recombinant bacterium capable of producing 4 moles of NADH per mole of sugar under anaerobic conditions.

In another aspect, the invention provides an isolated non-recombinant bacterium comprising a lpd gene having one or more mutations, wherein the mutation renders the non-recombinant bacterium capable of producing ethanol as the primary fermentation product under anaerobic conditions.

The invention also provides isolated nucleic acid molecules encoding dihydrolipoamide dehydrogenase (LPD) polypeptides or functional fragments thereof. When the nucleic acid molecules are expressed in a cell, e.g., a bacterium, the cell produces ethanol as the primary fermentation product.

Thus, in another aspect, the invention provides isolated nucleic acid molecules selected from the group consisting of:
a) a nucleic acid molecule comprising a nucleotide sequence which is at least 60% homologous to the nucleotide sequence of SEQ ID NO: 1 or SEQ ID NO: 3, or a complement thereof;
b) a nucleic acid molecule comprising a fragment of at least 100 nucleotides of a nucleic acid comprising the nucleotide sequence of SEQ ID NO: 1 or SEQ ID NO: 3, or a complement thereof;
c) a nucleic acid molecule which encodes a polypeptide comprising an amino acid sequence at least about 50% homologous to the amino acid sequence of SEQ ID NO: 2 or SEQ ID NO: 4;
d) a nucleic acid molecule which encodes a fragment of a polypeptide comprising the amino acid sequence of SEQ ID NO: 2 or SEQ ID NO: 4; wherein the fragment comprises at least 15 contiguous amino acid residues of the amino acid sequence of SEQ ID NO: 2 or SEQ ID NO: 4;
e) a nucleic acid which encodes a naturally occurring allelic variant of a polypeptide comprising the amino acid sequence of SEQ ID NO: 2 or SEQ ID NO: 4, wherein the nucleic acid molecule hybridizes to a complement of a nucleic acid molecule comprising SEQ ID NO: 1 or SEQ ID NO: 3, under stringent conditions;
f) a nucleic acid molecule comprising the nucleotide sequence of SEQ ID NO: 1 or SEQ ID NO: 3, or a complement thereof; and
g) a nucleic acid molecule which encodes a polypeptide comprising the amino acid sequence of SEQ ID NO: 2 or SEQ ID NO: 4;
wherein the nucleic acid molecule when expressed in a cell, renders the cell capable of producing ethanol as the primary fermentation product.

The invention also provides dihydrolipoamide dehydrogenase polypeptides or functional fragments thereof. When the polypeptides are expressed in a cell, e.g., a bacterium, the cell produces ethanol as the primary fermentation product.

Thus, in another aspect, the invention provides polypeptides selected from the group consisting of:

a) a fragment of a polypeptide comprising the amino acid sequence of SEQ ID NO: 2 or SEQ ID NO: 4, wherein the fragment comprises at least 15 contiguous amino acids of SEQ ID NO: 2 or SEQ ID NO: 4;
b) a naturally occurring allelic variant of a polypeptide comprising the amino acid sequence of SEQ ID NO; 2 or SEQ ID NO: 4, wherein the polypeptide is encoded by a nucleic acid molecule which hybridizes to the complement of a nucleic acid molecule comprising SEQ ID NO; 1 or SEQ ID NO: 3, under stringent conditions;
c) a polypeptide which is encoded by a nucleic acid molecule which is at least 50% identical to a nucleic acid comprising the nucleotide sequence of SEQ ID NO: 1 or SEQ ID NO: 3;
d) a polypeptide comprising an amino acid sequence which is at least 90% identical to the amino acid sequence of SEQ ID NO: 2 or SEQ ID NO: 4; and
e) an isolated polypeptide comprising the amino acid sequence of SEQ ID NO: 2 or SEQ ID NO: 4; and wherein the polypeptide when expressed in a cell, renders the cell capable of producing ethanol as the primary fermentation product.

In one embodiment, the ethanol produced by the cell comprises greater than 50% of total non-gaseous fermentation products under anaerobic conditions. In another embodiment of this aspect, the polypeptide has dihydrolipoamide dehydrogenase activity under anaerobic conditions. In a further embodiment, the cell is a bacterial cell.

In a further aspect, the invention provides a bacterial host cell comprising the isolated nucleic acid molecules encoding dihydrolipoamide dehydrogenase polypeptides or fragments thereof.

In another aspect, the invention provides a method for producing a polypeptide selected from the group consisting of:
a) a polypeptide comprising the amino acid sequence SEQ ID NO: 2 or SEQ ID NO: 4;
b) a fragment of a polypeptide comprising the amino acid sequence of SEQ ID NO: 2 or SEQ ID NO: 4; wherein the fragment comprises at least 15 contiguous amino acids of SEQ ID NO: 2 or SEQ ID NO: 4; and
c) a naturally occurring allelic variant of a polypeptide comprising the amino acid sequence of SEQ ID NO: 2 or SEQ ID NO: 4,
wherein the polypeptide is encoded by a nucleic acid molecule which hybridizes to a complement of a nucleic acid molecule comprising SEQ ID NO: 1 or SEQ ID NO: 3, under stringent conditions;
comprising culturing bacterial host cells containing the isolated nucleic acid molecules encoding dihydrolipoamide dehydrogenase polypeptides or fragments thereof, under conditions in which the nucleic acid molecule is expressed.

In a further aspect, the invention provides non-recombinant bacteria as described above, which comprise an isolated nucleic acid molecule described above.

A further aspect of the invention provides a non-recombinant bacterium comprising a lpd gene having one or more mutations, wherein the mutation renders the non-recombinant bacterium capable of producing ethanol as the primary fermentation product under anaerobic conditions, and wherein the bacterium is prepared by a process comprising the steps of:
a) growing a candidate mutant strain of the bacterium under anaerobic growth conditions in sugar-rich medium; and
b) selecting mutants that produce ethanol as the major product of fermentation.

In another aspect, the invention provides a method of producing ethanologenic non-recombinant bacteria of the invention comprising the steps of:
a) growing a candidate mutant strain of the bacterium under anaerobic growth conditions in sugar-rich medium; and
b) selecting mutants that produce ethanol as the major product of fermentation.

In one embodiment, the invention provides the isolated non-recombinant bacterium of any of the above-mentioned aspects, wherein the mutation in the lpd gene causes NADH insensitivity.

In another embodiment of the above-described aspects, the mutants result from mutation in the lpd gene. In a particular embodiment, the mutation in the lpd gene causes NADH insensitivity.

In another aspect, the invention provides a method for producing ethanol from an oligosaccharide source. The method comprises contacting the oligosaccharide with a non-recombinant bacterium or host cell of the invention as described above, to thereby produce ethanol from an oligosaccharide source. In a particular embodiment of the method, the oligosaccharide is selected from the group consisting of lignocellulose, hemicellulose, cellulose, pectin and any combination thereof.

In yet another aspect, the invention provides a kit comprising a non-recombinant bacterium or host cell of the invention as described above, and instructions for producing ethanol in accordance with the methods and processes described herein. In one embodiment, the kit comprises a sugar source.

In still another aspect, the invention provides novel *E. coli* strains, including strains AH218 (NRRL B-30967), AH241 (NRRL B-30968), AH242 (NRRL B-30969), SE2377 (NRRL B-30970), SE2378 (NRRL B-30971), SE2382 (NRRL B-30972), SE2383 (NRRL B-30973), SE2384 (NRRL B-30974), and SE2385 (NRRL B-30975), which were deposited on Sep. 27, 2006 with the Agricultural Research Culture Collection (NRRL), 1815 N. University Street, Peoria, Ill., USA.

Other features and advantages of the invention will be apparent from the following detailed description and claims.

BRIEF DESCRIPTION OF THE DRAWINGS

FIG. 1 (A) shows the nucleic acid sequence for the lpd gene with a mutation at base 997 (SEQ ID NO: 1) and (B) the corresponding amino acid sequence (SEQ ID NO: 2).

FIG. 2 (A) shows the nucleic acid sequence for the lpd gene with a mutation at base 1093 (SEQ ID NO: 3) and (B) the corresponding amino acid sequence (SEQ ID NO: 4).

FIG. 3 (A) shows the nucleic acid sequence for the wild type lpd gene (SEQ ID NO: 5) and (B) the corresponding amino acid sequence (SEQ ID NO: 6).

FIG. 6 shows the amino acid sequence of the pdhR gene product from the wild type W3110 strain and the SE2378 mutant (A). The nucleic acid sequence of the intergenic region of strain SE2378 is shown in (B).

FIG. 8 (A-C) is a schematic that shows the proposed pathway for ethanol production from pyruvate in *E. coli* strain SE2378, native *E. coli*, and other ethanologenic microorganisms.

FIG. 9 shows a multiple amino acid sequence alignment (using the CLUSTAL multiple sequence alignment program) of the LPD of *Escherichia coli* K12 MG1655 with selected LPD sequences, i.e. *Clostridium tetani* E88, *Thermoanaerobacter ethanolicus, Bacillus cereus* ATCC 10987, *Lactobacillus plantarum* WCFS1, *Lactococcus lactis* Subspecies *cremoris* SK11, *Oenococcus oeni* MCW PSU-1, *Salmonella typhimurium* LT2, *Vibrio fischeri* ATCC 700601, *Shewanella* sp ANA-3, *Pseudomonas aeruginosa* PAO1 (ATCC15692), *Rhodobacter sphaeroides* 2.4.1, *Geobacter metallireducens* GS-15, *Acinetobacter* sp. ADP1, *Gluconobacter oxydans* 621H, *Corynebacterium glutamicum* DSM20300, *Lactobacillus casei* ATCC334, *Streptomyces coelicolor* M145/A3(2), *Streptococcus mutans* ATCC 700610, *Methanosarcina barkeri* Fusaro. The histadine residue at amino acid 322, the proline residue at amino acid 355, and the glutamate residue at amino acid 356 are highlighted with an asterisk (*).

DETAILED DESCRIPTION OF THE INVENTION

Figure 4:
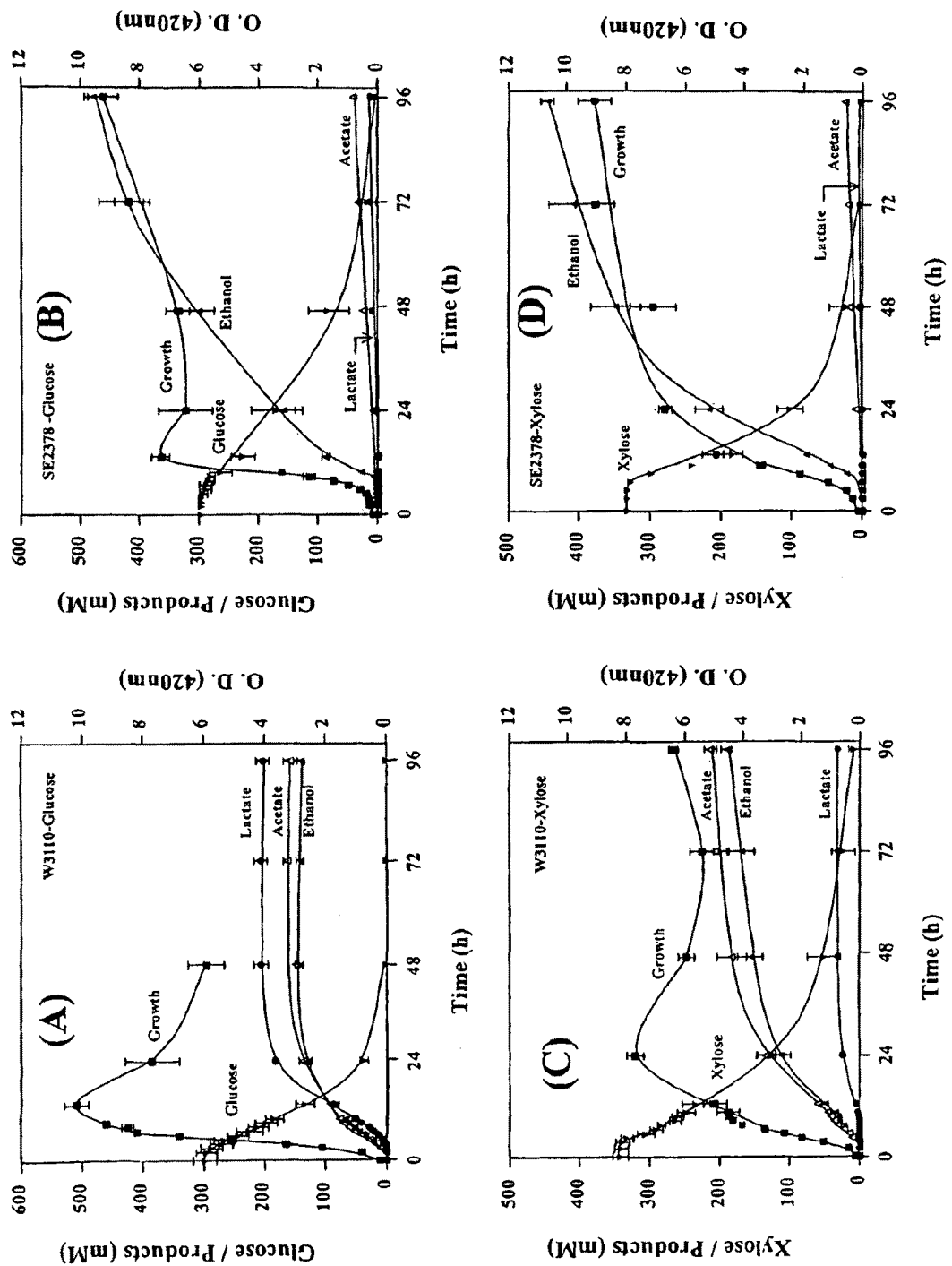
FIG. 4 shows a graph depicting the growth and fermentation characteristics of *E. coli* wild type, strain W3110, and ethanologenic mutant, strain SE2378, in LB-medium with glucose or xylose (50 g L$^{-1}$) at 37° C. and pH 7.0. Panel (A) shows the wild type W3110 strain, grown in glucose; Panel (B) shows the SE2378 strain, grown in glucose; Panel (C), shows the wild type W3110 strain, grown in, xylose; Panel (D) shows the SE2378 strain, grown in xylose

In order for the full scope of the invention to be clearly understood, the following definitions are provided.

I. Definitions

As used herein, the terms "non-recombinant bacterium" and "bacterium" are intended to include a bacterial cell that does or does not contain heterologous polynucleotide sequence, and is suitable for further modification using the compositions and methods of the invention, e.g. suitable for genetic manipulation, e.g., which can incorporate heterologous polynucleotide sequences, e.g., which can be transfected. The term is intended to include progeny of the cell originally transfected. In particular embodiments, the cell is a Gram-negative bacterial cell or a Gram-positive cell. The term "derived from" as in "polynucleotide or gene derived from a bacterium" is intended to include the isolation (in whole or in part) of a polynucleotide segment from the indicated source (i.e., the bacterium) or the purification of a polypeptide from an indicated source (i.e., the bacterium). In this regard, the term is intended to include, for example, direct cloning, PCR amplification, or artificial synthesis from, or based on, a sequence associated with the indicated polynucleotide source.

The term "anaerobic conditions" in intended to include conditions that do not include oxygen; i.e., conditions in which oxygen is substantially absent. In certain embodiments of the invention, anaerobic conditions comprise a closed vessel or container, for example a vessel closed with a stopper. To create conditions that do not include oxygen, the gas phase is removed from the vessel or container using a vacuum pump, and replaced with nitrogen gas. Oxygen is substantially absent when the oxygen level is too low to be detected. The term "aerobic conditions" is intended to include conditions that include oxygen; i.e., conditions in which oxygen is present.

The term "ethanologenic" is intended to include the ability of a microorganism to produce ethanol from a carbohydrate as a primary fermentation product. The term is intended to include naturally occurring ethanologenic organisms and ethanologenic organisms with naturally occurring or induced mutations.

The term "non-ethanologenic" is intended to include the inability of a microorganism to produce ethanol from a carbohydrate as a primary fermentation product. The term is intended to include microorganisms that produce ethanol as the minor fermentation product comprising less than 40% of total non-gaseous fermentation products.

The terms "fermenting" and "fermentation" are intended to include the degradation or depolymerization of a complex sugar and bioconversion of that sugar residue into ethanol, acetate and succinate. The terms are intended to include the enzymatic process (e.g. cellular or acellular, e.g. a lysate or purified polypeptide mixture) by which ethanol is produced from a carbohydrate, in particular, as a primary product of fermentation.

The terms "primary fermentation product" and "major fermentation product" are used herein interchangeably and are intended to include non-gaseous products of fermentation that comprise greater than about 50% of total non-gaseous product. The primary fermentation product is the most abundant non-gaseous product. In certain embodiments of the invention, the primary fermentation product is ethanol.

The term "minor fermentation product" as used herein is intended to include non-gaseous products of fermentation that comprise less than 40% of total non-gaseous product. In certain embodiments of the invention, the minor fermentation product is ethanol.

The term "homoethanol fermentation pathway" as used herein is intended to include the fermentation pathway in an organism, e.g., a bacterium, that facilitates production of ethanol as the primary fermentation product.

The term "alternative fermentation pathway" as used herein is intended to include the fermentation pathway wherein ethanol is not the primary fermentation product.

A "gene," as used herein, is a nucleic acid that can direct synthesis of an enzyme or other polypeptide molecule, e.g., can comprise coding sequences, for example, a contiguous open reading frame (ORF) that encodes a polypeptide, or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. In addition, the term "gene" is intended to include a specific gene for a selected purpose. A gene can be endogenous to the host cell or can be recombinantly introduced into the host cell, e.g., as a plasmid maintained episomally or a plasmid (or fragment thereof) that is stably integrated into the genome. A heterologous gene is a gene that is introduced into a cell and is not native to the cell.

The terms "pdh operon" and "pdh locus" are used interchangeable and are intended to mean the pdhR, lpd, and aceEF cluster of genes that are expressed as a group, and their associated promoter and operator. By convention, the term "pdh operon" refers to the genes which encode the operon, whereas the term "PDH" refers to the complex of proteins that are encoded by the operon. Pyruvate dehydrogenase activity is responsible for the production of acetyl CoA for the TCA cycle and energy production. The term pdh operon can include a pdh operon from any aerobic organism. All aerobic organisms, from eukaryotes to humans, contain the three components of PDH. Many bacteria have the genes encoding PDH contained in an operon. The three genes, aceE, aceF and lpd are essential for the activity of PDH, and these three genes are found in all aerobic organisms whether they are organized as an operon or as independent genes.

The term "dihydrolipoamide acetyltransferase" (aceF) is intended to include the E2 acetyltransferase enzymes of the pyruvate dehydrogenase gene locus. By convention, the term "aceF" refers to a dihydrolipoamide acetyltransferase gene whereas the term "AceF" refers to an aceF gene product, i.e., a dihydrolipoamide acetyltransferase polypeptide or enzyme.

The term "pyruvate decarboxylase/dehydrogenase of the PDH complex" (aceE) is intended to include the E1 decarboxylase enzyme of the pyruvate dehydrogenase gene locus. By convention, the term "aceE" refers to a pyruvate decarboxylase/dehydrogenase gene whereas the term "AceE" refers to an aceE gene product, i.e., a pyruvate decarboxylase/dehydrogenase polypeptide or enzyme.

The term "pyruvate dehydrogenase repressor" (pdhR) is intended to include the transcriptional repressor of the pdh operon. By convention, the term "pdhR" refers to a pyruvate dehydrogenase repressor gene whereas the term "PdhR" refers to a pdhR gene product, i.e., a pyruvate dehydrogenase repressor polypeptide.

The term "dihydrolipoamide dehydrogenase" (lpd) is intended to include the enzyme that is part of the pyruvate dehydrogenase gene locus or "pdh operon". By convention, the term "lpd" refers to a dihydrolipoamide dehydrogenase gene whereas the term "LPD" refers to a lpd gene product, i.e., a dihydrolipoamide dehydrogenase polypeptide or enzyme. The nucleotide sequence of the wild-type lpd gene is represented by SEQ ID NO: 5, shown in FIG. 3(A), and the amino acid sequence of the polypeptide expressed by the wild-type lpd gene is represented by SEQ ID NO: 6, shown in FIG. 3(B).

The term "lactate dehydrogenase" (ldhA) is intended to include the enzyme that converts pyruvate to lactate under fermentative conditions. By convention, the term "ldhA" refers to a lactate dehydrogenase gene whereas the term "LDHA" refers to a ldhA gene product, i.e., a lactate dehydrogenase polypeptide or enzyme.

The term "pyruvate formate lyase" (pfl) is intended to include the enzyme that converts pyruvate to Acetyl-CoA and formate under fermentative conditions. By convention, the term "pfl" refers to a pyruvate formate lyase gene whereas the term "PFL" refers to a pfl gene product, i.e., a pyruvate formate lyase polypeptide or enzyme.

The term "alcohol dehydrogenase" (adhE) is intended to include the enzyme that converts Acetyl-CoA to ethanol under fermentative conditions. By convention, the term "adhE" refers to an alcohol dehydrogenase gene whereas the term "ADHE" refers to a adhE gene product, i.e., a alcohol dehydrogenase polypeptide or enzyme.

The term "NADH insensitivity" means a decrease in sensitivity of the PDH enzyme to NADH. The term is intended to include a partial decrease insensitivity or a complete lack of sensitivity.

The term "nucleic acid" is intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. In one embodiment, the gene of polynucleotide segment is involved in at least one step in the bioconversion of a carbohydrate to ethanol. Accordingly, the term is intended to include any gene encoding a polypeptide such as a pyruvate decarboxylase, an alcohol dehydrogenase, a secretory polypeptide/s, or a polysaccharase, e.g., a glucanase, or a combination thereof. A gene in an organism can be clustered in an operon, as defined herein, wherein the operon is separated from other genes and/or operons by intergenic DNA. Individual genes contained within a pdh operon can overlap without intergenic DNA between the individual genes.

The term "homologous" is intended to include a first amino acid or nucleotide sequence which contains a sufficient or minimum number of identical or equivalent amino acid residues or nucleotides, e.g., an amino acid residue which has a similar side chain, to a second amino acid or nucleotide sequence such that the first and second amino acid or nucleotide sequences share common structural domains and/or a common functional activity.

The term "heterologous polypeptide" is intended to include a polypeptide or fragment thereof that can be encoded by a heterologous nucleic acid derived from any source, e.g., eukaryotes, prokaryotes, archaea, virii, or synthetic nucleic acid fragments.

The term an "isolated polypeptide" (e.g., an isolated or purified biosynthetic enzyme) is substantially free of cellular material or other contaminating polypeptides from the microorganism from which the polypeptide is derived, or substantially free from chemical precursors or other chemicals when chemically synthesized.

The term "fragment" as in "nucleotide fragment" or "polypeptide fragment" is intended to mean a portion of the nucleotide sequence or polypeptide sequence that is substantially identical to at least a portion of sequence from which it is derived, and where the polypeptide retains the biological activity from the sequence from which it is derived.

The term "pH" is intended to mean a measure of the molar concentration of hydrogen ions in a solution, and as such is a measure of the acidity or basicity of the solution. According to the standard in the art, the term pH is used to define solutions. The usual range of pH values encountered is between 0 and 14, with 0 being the value for concentrated hydrochloric acid (1 M HCl), 7 the value for pure water (neutral pH), and 14 being the value for concentrated sodium hydroxide (1 M NaOH).

The term "pK" is intended to mean a measure of proton binding affinity, and is often used interchangeably with pH. One skilled in the art will recognize that the term pK is used to define proteins, amino acids and peptides. One skilled in the art will also recognize that the acidic strength of the carboxyl, amino and ionizable R-groups in amino acids can be defined by the association constant, K, or more commonly the negative logarithm of $K_a$, the $pK_a$.

The term "vector" is intended to include any plasmid vector suitable for ligation of nucleotide sequence of interest and transformation into host cell.

The term "sugar" is intended to include any carbohydrate source comprising a sugar molecule(s). Such sugars are potential sources of sugars for depolymerization (if required) and subsequent bioconversion to acetaldehyde and subsequently to ethanol by fermentation according to the products and methods of the present invention. Sources of sugar include starch, the chief form of fuel storage in most plants, and cellulose, the main extracelluloar structural component of the rigid cell walls and the fibrous and woody tissues of plants. The term is intended to include monosaccharides, also called simple sugars, oligosaccharides and polysaccharides. In certain embodiments, sugars include, e.g., glucose, xylose, arabinose, mannose, galactose, sucrose, and lactose. In other embodiments, the sugar is glucose.

The term "Gram-negative bacterial cell" is intended to include the art-recognized definition of this term. Exemplary Gram-negative bacteria include *Acinetobacter, Gluconobacter, Escherichia, Geobacter, Shewanella, Salmonella, Eneterobacter* and *Klebsella*.

The term "Gram-positive bacteria" is intended to include the art-recognized definition of this term. Exemplary Gram-positive bacteria include *Bacillus, Clostridium, Corynebacterium, Lactobacillis, Lactococcus, Oenococcus, Streptococcus* and *Eubacterium*.

The phrase "mutant nucleic acid molecule" or "mutant gene" is intended to include a nucleic acid molecule or gene having a nucleotide sequence which includes at least one alteration (e.g., substitution, insertion, deletion) such that the polypeptide or polypeptides that can be encoded by the mutant exhibits an activity that differs from the polypeptide or polypeptide encoded by the wild-type nucleic acid molecule or gene.

The term "amino acid" is intended to include the 20 alpha-amino acids that regularly occur in proteins. Basic charged amino acids include arginine, asparagine, glutamine, histidine and lysine. Neutral charged amino acids include alanine, cysteine, glycine, isoleucine, leucine, methionine, phenylalanine, proline, serine, threonine, tryptophan, tyrosine, and valine. Acidic amino acids include aspartic acid and glutamic acid.

The term "mutagenizing agent" is intended to include any agent that can be used according to the method of the invention to modify a nucleotide sequence.

The term "spontaneous mutation" is intended to include a mutation that occurs in the absence of mutagens. The term can include a mutation that occurs in the method of the invention without the addition of a mutagenizing agent.

II. Non-Recombinant Bacteria

During mixed acid fermentations, the enzymes of glycolysis convert each mole of glucose into 2 moles of pyruvate plus 2 moles of NADH and a net 2 moles of ATP. The production of compounds more reduced than pyruvate (ethanol, lactate, etc.) serves as a mechanism to oxidize NADH and regenerate $NAD^+$, essential for continued glycolysis. In the only known homoethanol pathway that evolved in yeast, plants, and bacteria (i.e., *Z. mobilis*), pyruvate is decarboxylated to yield carbon dioxide and acetaldehyde by the non-oxidative pyruvate decarboxylase. The resulting acetaldehyde serves as the electron acceptor for NADH oxidation by alcohol dehydrogenase during production of one ethanol.

A completely different ethanol pathway exists in many other types of bacteria, in which pyruvate is first converted to acetyl-CoA and formate by pyruvate formate-lyase, an oxidative decarboxylation in which reducing equivalents are contained in the formate and dissipated as hydrogen gas (and $CO_2$) by formate hydrogen-lyase. Acetyl-CoA is subsequently used as the electron acceptor for the oxidation of two NADH molecules by adhE-encoded aldehyde-alcohol dehydrogenase activities. Due to the requirement of 2 NADH per ethanol, half of the acetyl-CoA remains and is converted to acetate and an additional ATP. Thus the native *E. coli* pathway for ethanol from acetyl-CoA cannot support homoethanol fermentation due to the need for 2 NADH per ethanol produced from acetyl-CoA. Redox balance is preserved by acetate production. This is the main reason that wild type *E. coli* produces equimolar amounts of acetate and ethanol during fermentation.

Pyruvate dehydrogenase oxidatively decarboxylates pyruvate to acetyl-CoA and conserves the associated reductant as NADH. This is in contrast to PFL in which the associated reductant is dissipated as hydrogen gas through formate as an intermediate and is not available for metabolic activity in the presence of glucose. By metabolizing pyruvate with PDH, an additional NADH per pyruvate is made available that can be used to fully reduce each acetyl-CoA to ethanol. Although genes coding for pyruvate dehydrogenase are typically expressed under both aerobic and anaerobic conditions in *E. coli*, the activity of this complex during anaerobic growth is very low.

The invention is based, at least on part, on the discovery of a mutation that redirects glycolysis via a homoethanol pathway in microorganisms that are otherwise non-ethanologenic and the development of non-recombinant ethanologenic microorganisms that ferment glucose and xylose to ethanol under anaerobic conditions based on that discovery. In accordance with this redirected glycolysis, the non-recombinant bacteria of the invention produce 4 moles of NADH per mole of sugar, or 2 NADH per pyruvate, under anaerobic conditions.

Thus, in one aspect, the invention provides a non-recombinant bacterium comprising a mutation, wherein the mutation renders the non-recombinant bacterium capable of producing 4 moles of NADH per mole of sugar under anaerobic conditions. In one embodiment, the mutation is located in a pdh operon. In a particular embodiment, the pdh operon comprises pdhR, aceEF and lpd genes. In a further embodiment, the mutation is in the lpd gene.

In another embodiment, the production of 4 moles of NADH per mole of sugar results in the production of ethanol as the primary fermentation product. In a particular embodiment, the sugar is selected from the group consisting of: glucose, xylose, arabinose, mannose, galactose, sucrose, and lactose.

In another aspect, the invention provides a non-recombinant bacterium comprising a lpd gene having one or more mutations, wherein the mutation renders the non-recombinant bacterium capable of producing ethanol as the primary fermentation product under anaerobic conditions.

In one embodiment, the ethanol produced comprises greater than 50% of total non-gaseous fermentation products under anaerobic conditions.

In a further embodiment, the non-recombinant bacterium, in the absence of the mutation, is non-ethanologenic. In yet a further embodiment, the non-ethanologenic bacterium produces ethanol as a minor fermentation product. In one embodiment, the ethanol produced is less than 40% of the total non-gaseous fermentation products.

In yet a further embodiment of the invention, the mutation in the lpd gene provides a homoethanol pathway by which ethanol is produced by the bacterium as the primary fermentation product.

In a further embodiment, one or more alternative pathways for fermentation in the bacterium are inactivated. In one embodiment the alternative pathways are inactivated by mutation. Such a mutation includes deletion, substitution or addition of nucleotides in one or more genes in the alternative pathway. In another embodiment, the mutation is in an ldh gene, e.g., the ldhA gene. In yet another embodiment, the mutation is in the pfl gene, e.g., the pflB gene. In still another embodiment, the alternative pathways for fermentation include lactate production by lactate dehydrogenase (ldh), acetate, ethanol, formate or $H_2$ and $CO_2$ conversion by pyruvate formate-lyase (pfl) or production of succinate.

In various embodiments of the non-recombinant bacteria and bacterial cells described herein, the bacteria are selected from the group consisting of Gram-negative bacteria and Gram-positive bacteria. In certain embodiments, the bacteria are Gram-negative bacteria. In particular embodiments, the Gram-negative bacteria are selected from the group consisting of *Acinetobacter, Gluconobacter, Escherichia, Geobacter, Shewanella, Salmonella, Eneterobacter* and *Klebsella*. In other embodiments, the bacteria are Gram-positive bacteria. In particular embodiments, the Gram-positive bacteria are selected from the group consisting of *Bacillus, Clostridium, Corynebacterium, Lactobacillis, Lactococcus, Oenococcus, Streptococcus* and *Eubacterium*. In still further embodiments, the bacteria are *Escherichia coli*.

As described above, the non-recombinant bacteria of the invention comprise one or more mutations, e.g., a mutation in an lpd gene. In one embodiment, the mutation comprises substitution of an amino acid with another amino acid, such that the substitution changes the pK of the polypeptide expressed by the mutated lpd gene. In certain embodiments, the mutation in the lpd gene causes NADH insensitivity. That is, a cell carrying such a mutation manifests a decrease in sensitivity of the PDH enzyme to NADH. Thus, an NADH insensitive cell produces four NADH molecules per glucose (2 from glycolysis and 2 from PDH reaction), and all four NADHs may be used to reduce two acetyl-CoA to ethanol. In certain embodiments, NADH insensitivity of the PDH to NADH and its ability to function even with a high NADH/NAD ratio enables a cell, e.g., a bacterial cell, to be a homoethanol producer.

In one embodiment, the polypeptide comprises SEQ ID NO: 6 and the mutation comprises a substitution of a wild type amino acid with another amino acid at:
 a) position 322 or any position within about 50 positions on either side of position 322 in SEQ ID NO: 6; or
 b) position 354 or any position within about 50 positions on either side of position 354 in SEQ ID NO: 6.

In certain embodiments, the other amino acid is a neutral amino acid selected from the group consisting of alanine, cysteine, glycine, isoleucine, leucine, methionine, phenylalanine, proline, serine, threonine, tryptophan, tyrosine, and valine. In other embodiments, the other amino acid is a basic amino acid selected from the group consisting of arginine, asparagine, glutamine, histidine and lysine.

In one embodiment, the mutation comprises a substitution of H at position 322 with any amino acid, such that the amino acid substitution increases the acidity of the polypeptide expressed by the mutated lpd gene. In a particular embodiment, the non-recombinant bacterium has a mutation that comprises a substitution of H to Y at position 322 in SEQ ID NO: 6. In one embodiment, the non-recombinant bacterium is *E. coli* strain SE2377, represented by a deposit with the Agricultural Research Culture Collection and designated as deposit number NRRL B-30970. In another embodiment, the non-recombinant bacterium is *E. coli* strain SE2383, represented by a deposit with the Agricultural Research Culture Collection and designated as deposit number NRRL B-30973. In yet another embodiment, the non-recombinant bacterium is *E. coli* strain SE2384, represented by a deposit with the Agricultural Research Culture Collection and designated as deposit number NRRL B-30974. In a further embodiment, strain SE2377 comprises SEQ ID NO: 1, or a fragment thereof. In another further embodiment, strain SE2383 comprises SEQ ID NO: 1, or a fragment thereof. In still another further embodiment, strain SE2384 comprises SEQ ID NO: 1, or a fragment thereof.

In another embodiment, the mutation comprises a substitution of E at position 354 with any amino acid, such that the amino acid substitution reduces the acidity of the polypeptide expressed by the mutated lpd gene. In a particular embodiment, the non-recombinant bacterium has a mutation that comprises a substitution of E to K at position 354 in SEQ ID NO: 6. In one embodiment, the non-recombinant bacterium is *E. coli* strain SE2378, represented by a deposit with the Agricultural Research Culture Collection and designated as deposit number NRRL B-30971. In another embodiment, the non-recombinant bacterium is *E. coli* strain SE2382, represented by a deposit with the Agricultural Research Culture Collection and designated as deposit number NRRL B-30972. In yet another embodiment, the non-recombinant bacterium is *E. coli* strain SE2385, represented by a deposit with the Agricultural Research Culture Collection and designated as deposit number NRRL B-30975. In a further embodiment, strain SE2378 comprises SEQ ID NO: 3, or a fragment thereof. In another further embodiment, strain SE2382 comprises SEQ ID NO: 3, or a fragment thereof. In still a further embodiment, strain 2385, comprises SEQ ID NO: 3, or a fragment thereof.

The non-recombinant bacteria comprising one or more of the mutations described above are suitable for producing ethanol from sugar. In accordance with the invention, the mutation provides a homoethanol fermentation pathway. In certain embodiments, the ethanol produced comprises greater than 50% of total non-gaseous fermentation products under anaerobic conditions.

In one embodiment, the mutation result from spontaneous mutation. In another embodiment, the bacterium is exposed to a mutagenizing agent. In a particular embodiment, the mutagenizing agent is selected from the group consisting of ethyl methane sulfonate, 2-aminopurine, ICR-191, methyl methane sulfonate, N-methyl-N'-nitro-N-nitrosoguanidine. In a further particular embodiment, the mutagenizing agent is ethyl methane sulfonate (EMS).

In another embodiment, one or more alternative pathways for fermentation in the bacterium are inactivated. Alternative pathways for fermentation include lactate production by lactate dehydrogenase (ldh), acetate, ethanol, formate, $H_2$ and $CO_2$ starting with pyruvate formate-lyase (pfl) and succinate. In one embodiment, the alternative pathways for fermentation are inactivated by mutation. In particular embodiments, the alternative fermentation pathways are inactivated by introducing deletion mutations in the bacterium.

II. Isolated Nucleic Acid Molecules and Genes

The invention also provides isolated nucleic acid molecules encoding dihydrolipoamide dehydrogenase (lpd) polypeptides or fragments thereof. The nucleic acid molecules of the invention comprise an lpd gene with one or more mutations that when present in bacterium of the invention results in the production by the bacterium of ethanol as the primary fermentation product under anaerobic conditions.

The nucleic acid molecules of the invention include DNA molecules and RNA molecules and analogs of the DNA or RNA generated using nucleotide analogs. The nucleic acid molecule can be single-stranded or double-stranded, but advantageously is double-stranded DNA.

In one aspect, the invention provides isolated nucleic acid molecules selected from the group consisting of:
a) a nucleic acid molecule comprising a nucleotide sequence which is at least 60% homologous to the nucleotide sequence of SEQ ID NO: 1 or SEQ ID NO: 3, or a complement thereof;
b) a nucleic acid molecule comprising a fragment of at least 100 nucleotides of a nucleic acid comprising the nucleotide sequence of SEQ ID NO: 1 or SEQ ID NO: 3, or a complement thereof;
c) a nucleic acid molecule which encodes a polypeptide comprising an amino acid sequence at least about 50% homologous to the amino acid sequence of SEQ ID NO: 2 or SEQ ID NO: 4;
d) a nucleic acid molecule which encodes a fragment of a polypeptide comprising the amino acid sequence of SEQ ID NO: 2 or SEQ ID NO: 4; wherein the fragment comprises at least 15 contiguous amino acid residues of the amino acid sequence of SEQ ID NO: 2 or SEQ ID NO: 4;
e) a nucleic acid which encodes a naturally occurring allelic variant of a polypeptide comprising the amino acid sequence of SEQ ID NO: 2 or SEQ ID NO: 4, wherein the nucleic acid molecule hybridizes to a complement of a nucleic acid molecule comprising SEQ ID NO: 1 or SEQ ID NO: 3, under stringent conditions;
f) a nucleic acid molecule comprising the nucleotide sequence of SEQ ID NO: 1 or SEQ ID NO: 3, or a complement thereof; and
g) a nucleic acid molecule which encodes a polypeptide comprising the amino acid sequence of SEQ ID NO: 2 or SEQ ID NO: 4;
wherein the nucleic acid molecule when expressed in a cell, renders the cell capable of producing ethanol as the primary fermentation product.

In one embodiment, the ethanol produced by the cell comprises greater than 50% of total non-gaseous fermentation products under anaerobic conditions. In another embodiment, the cell is a bacterial cell. In yet another embodiment, the bacterial cell, in the absence of expression of the nucleic acid molecule, is non-ethanologenic. In a particular embodiment, the non-ethanologenic bacterial cell produces ethanol as the minor fermentation product; i.e., less than about 40% of total non-gaseous fermentation products.

In another embodiment, the bacterial cell produces ethanol as the primary fermentation product under anaerobic conditions. In a particular embodiment, expression of the nucleic acid molecule in the bacterial cell provides a homoethanol fermentation pathway in the bacterial cell through which ethanol is produced as the primary fermentation product.

In yet another embodiment of this aspect of the invention, the nucleic acid molecule comprises a fragment of SEQ ID NO: 1 wherein the nucleic acid molecule is at least 100 nucleotides in length and contains a T at a position corresponding to position 997 of SEQ ID NO: 1.

In another embodiment, the nucleic acid molecule comprises a fragment of SEQ ID NO: 3 wherein the nucleic acid molecule is at least 100 nucleotides in length and contains a G at a position corresponding to position 1023 of SEQ ID NO: 1.

In one embodiment, the lpd nucleic acid molecule of the invention is at least 60%, 70%, 75%, 80%, 85%, 90%, 91%, 92%, 93%, 94%, 95%, 96%, 97%, 98%, or more identical to the nucleotide sequence (e.g., when compared to the overall length of the nucleotide sequence) shown in SEQ ID NO: 1 or SEQ ID NO: 3, or a complement thereof. SEQ ID NO: 1 and SEQ ID NO: 3 are shown in FIGS. 1(A) and 3(A), respectively.

In another embodiment, the invention provides an isolated nucleic acid molecule comprises a fragment of at least 100, 150, 200, 250, or 300 nucleotides of a nucleic acid molecule comprising the nucleotide sequence of SEQ ID NO: 1 or SEQ ID NO: 3, or a complement thereof.

In another particular embodiment, the invention provides a nucleic acid molecule which encodes a polypeptide comprising an amino acid sequence at least about 50%, 60%, 70%, 75%, 80%, 85%, 90%, 91%, 92%, 93%, 94%, 95%, 96%, 97%, 98%, or more identical to the amino acid sequence of SEQ ID NO: 2 or SEQ ID NO: 4, shown in FIG. 1(B) and FIG. 2 (B).

In another embodiment, the nucleic acid molecule encodes a fragment of a polypeptide comprising the amino acid sequence of SEQ ID NO: 2 or SEQ ID NO: 4, wherein the fragment comprises at least 15, 25, 35, 45, 55, 65 contiguous amino acid residues of the amino acid sequence of SEQ ID NO: 2 or SEQ ID NO: 4.

In a further aspect, the invention provides non-recombinant bacteria as described above, which comprise an isolated nucleic acid molecule described above. In one embodiment, the non-recombinant bacterium produces ethanol from a sugar. In another embodiment, the sugar is selected from the group consisting of glucose, xylose, arabinose, mannose, galactose, sucrose, and lactose.

The lpd genes, as described herein (and italicized by convention), include a nucleic acid molecule (e.g., a DNA molecule or segment thereof), for example, a polypeptide or RNA-encoding nucleic acid molecule that, in an organism, is separated from another gene or other genes, by intergenic DNA (i.e., intervening or spacer DNA which naturally flanks the gene and/or separates genes in the chromosomal DNA of the organism). A gene can direct synthesis of an enzyme or other polypeptide molecule (e.g., can comprise coding sequences, for example, a contiguous open reading frame (ORF) which encodes a polypeptide) or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes.

An embodiment of the present invention features mutant lpd nucleic acid molecules or genes. Typically, a mutant nucleic acid molecule or mutant gene as described herein, includes a nucleic acid molecule or gene having a nucleotide sequence which includes at least one alteration (e.g., substitution, insertion, deletion) such that the polypeptide or polypeptide that can be encoded by the mutant exhibits an activity that differs from the polypeptide or polypeptide encoded by the wild-type nucleic acid molecule or gene. Advantageously, a mutant nucleic acid molecule or mutant gene (e.g., a mutant lpd gene) encodes a LPD polypeptide having improved activity, e.g., dihydrolipoamide dehydrogenase activity.

In one embodiment, a nucleic acid molecule of the invention hybridizes under stringent conditions to a nucleic acid molecule having a nucleotide sequence set forth as SEQ ID NO: 1 or SEQ ID NO: 3. Such stringent conditions are known to those skilled in the art and can be found in *Current Protocols in Molecular Biology*, John Wiley & Sons, N.Y. (1989), 6.3.1-6.3.6. A particular, non-limiting example of stringent (e.g. high stringency) hybridization conditions are hybridization in 6× sodium chloride/sodium citrate (SSC) at about 45° C., followed by one or more washes in 0.2×SSC, 0.1% SDS at 50-65° C. Advantageously, an isolated nucleic acid molecule of the invention that hybridizes under stringent conditions to the sequence of SEQ ID SEQ ID NO: 1, SEQ ID NO: 3 corresponds to a naturally occurring nucleic acid molecule. Typically, a naturally occurring nucleic acid molecule includes an RNA or DNA molecule having a nucleotide sequence that occurs in nature.

A nucleic acid molecule of the present invention (e.g., a nucleic acid molecule having the nucleotide sequence of SEQ ID NO: 1, SEQ ID NO: 3) can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989) or can be isolated by the polymerase chain reaction using synthetic oligonucleotide primers designed based upon the sequence of SEQ ID NO: 1, SEQ ID NO: 3. A nucleic acid of the invention can be amplified using cDNA, mRNA or alternatively, genomic DNA, as a template and appropriate oligonucleotide primers according to standard PCR amplification techniques. In another embodiment, an isolated nucleic acid molecule of the invention comprises a nucleic acid molecule which is a complement of the nucleotide sequence shown in SEQ ID NO: 1, SEQ ID NO: 3.

Additional lpd nucleic acid sequences are those that comprise the nucleotide sequence of SEQ ID NO: 1, SEQ ID NO: 3, that encode a homologue of the polypeptide having the amino acid sequence set forth in SEQ ID NO: 2 or SEQ ID NO: 4 (e.g., encode a polypeptide having at least 30%, 40%, 50%, 60%, 70%, 80%, 90%, 95% or more identity to the polypeptide having the amino acid sequence as set forth in SEQ ID NO: 2, SEQ ID NO: 4, and having a substantially identical activity as the polypeptide), hybridize under stringent conditions to all or a fragment of a nucleic acid molecule having the nucleotide sequence of SEQ ID NO: 1, SEQ ID NO: 3 or to all or a fragment of a nucleic acid molecule that encodes a polypeptide having the amino acid sequence of SEQ ID NO: 2, SEQ ID NO: 4, or are complementary to a lpd nucleotide sequence as set forth herein, and such that the lpd nucleic acid sequences, when expressed in a cell, result in the production by the cell of ethanol as the primary fermentation product under anaerobic conditions In one embodiment, the nucleic acid molecule encodes a polypeptide or a biologically active fragment of a polypeptide comprising the amino acid sequence of SEQ ID NO: 2 or SEQ ID NO: 4, wherein the polypeptide or the biologically active fragment retains the ability to produce ethanol in a host cell.

In another embodiment, an lpd nucleic acid molecule or gene encodes a homologue of the LPD polypeptide having the amino acid sequence of SEQ ID NO: 2 or SEQ ID NO: 4. Typically, the term "homologue" includes a polypeptide or polypeptide sharing at least about 30-35%, advantageously at least about 35-40%, more advantageously at least about 40-50%, and even more advantageously at least about 60%, 70%, 80%, 90% or more identity with the amino acid sequence of a wild-type polypeptide or polypeptide described herein and having a substantially equivalent functional or biological activity as the wild-type polypeptide or polypeptide. For example, a LPD homologue shares at least about 60%, advantageously at least about 60%, 70%, 75%, 80%, 85%, 90%, 91%, 92%, 93%, 94%, 95%, 96%, 97%, 98%, or more identity with the polypeptide having the amino acid sequence set forth as SEQ ID NO: 2 or SEQ ID NO: 4, and has a substantially equivalent functional or biological activity (i.e., is a functional equivalent) of the polypeptide having the amino acid sequence set forth as SEQ ID NO: 2 or SEQ ID NO: 4 (e.g., has a substantially equivalent dihydrolipoamide dehydrogenase activity).

In an embodiment, an lpd nucleic acid molecule or gene comprises a nucleotide sequence that encodes a polypeptide as set forth as SEQ ID NO: 2 or SEQ ID NO: 4.

In another embodiment, an lpd nucleic acid molecule hybridizes to all or a fragment of a nucleic acid molecule having the nucleotide sequence set forth in SEQ ID NO: 1 or SEQ ID NO: 3, or hybridizes to all or a portion of a nucleic acid molecule having a nucleotide sequence that encodes a polypeptide having the amino acid sequence of any of SEQ ID NO: 2 or SEQ ID NO: 4.

Such hybridization conditions are known to those skilled in the art and can be found in *Current Protocols in Molecular Biology*, Ausubel, et al., eds., John Wiley & Sons, Inc. (1995), sections 2, 4 and 6. Additional stringent conditions can be found in *Molecular Cloning: A Laboratory Manual*, Sambrook, et al., Cold Spring Harbor Press, Cold Spring Harbor, N.Y. (1989), chapters 7, 9 and 11. A particular, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A particular, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A particular, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SCC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m (°C.)=81.5+16.6(\log_{10}[Na^+])+0.41(\%G+C)-(600/N)$, where N is the number of bases in the hybrid, and $[Na^+]$ is the concentration of sodium ions in the hybridization buffer ($[Na^+]$ for 1×SSC=0.165 M).

It will also be recognized by the skilled practitioner that additional reagents can be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or, alternatively, 0.2×SSC, 1% SDS). In another embodiment, an isolated nucleic acid molecule comprises a nucleotide sequence that is complementary to a lpd nucleotide sequence as set forth herein (e.g., is the full complement of the nucleotide sequence set forth as SEQ ID NO: 1 or SEQ ID NO: 3).

III. Polypeptides

The invention features polypeptides (e.g., mutant ethanologenic enzymes, for example, dihydrolipoamide dehydrogenase (LPD)). When the polypeptides are expressed in a cell, e.g., a bacterium, the cell produces ethanol as the primary fermentation product under anaerobic conditions.

Thus, in another aspect, the invention provides polypeptides selected from the group consisting of:
 a) a fragment of a polypeptide comprising the amino acid sequence of SEQ ID NO: 2 or SEQ ID NO: 4, wherein the fragment comprises at least 15 contiguous amino acids of SEQ ID NO: 2 or SEQ ID NO: 4;
 b) a naturally occurring allelic variant of a polypeptide comprising the amino acid sequence of SEQ ID NO; 2 or SEQ ID NO: 4, wherein the polypeptide is encoded by a nucleic acid molecule which hybridizes to the complement of a nucleic acid molecule comprising SEQ ID NO; 1 or SEQ ID NO: 3, under stringent conditions;
 c) a polypeptide which is encoded by a nucleic acid molecule which is at least 50% identical to a nucleic acid comprising the nucleotide sequence of SEQ ID NO: 1 or SEQ ID NO: 3;
 d) a polypeptide comprising an amino acid sequence which is at least 90% identical to the amino acid sequence of SEQ ID NO: 2 or SEQ ID NO: 4; and
 e) an isolated polypeptide comprising the amino acid sequence of SEQ ID NO: 2 or SEQ ID NO: 4; and wherein the polypeptide when expressed in a cell, renders the cell capable of producing ethanol as the primary fermentation product.

In one embodiment, the ethanol produced by the cell comprises greater than 50% of total non-gaseous fermentation products under anaerobic conditions. In another embodiment of this aspect, the polypeptide has dihydrolipoamide dehydrogenase activity under anaerobic conditions. In a further embodiment, the cell is a bacterial cell.

In yet another embodiment, the bacterial cell, in the absence of expression of the polypeptide, is non-ethanologenic. In a particular embodiment, the non-ethanologenic bacterial cell produces ethanol as the minor fermentation product; i.e., less than about 40% of total non-gaseous fermentation products.

In a further embodiment, the bacterial cell produces ethanol as the primary fermentation product under anaerobic conditions, and in yet a further embodiment the the ethanol produced comprises greater than 50% of total non-gaseous fermentation products under anaerobic conditions. In a particular embodiment, expression of the polypeptide in the bacterial cell provides a homoethanol fermentation pathway in the bacterial cell.

In another embodiment, the isolated polypeptide of the invention is a fragment of a polypeptide comprising the amino acid sequence of SEQ ID NO: 2 or SEQ ID NO: 4, wherein the fragment comprises at least 15, 25, 35, 45, 55, or 65 contiguous amino acid residues of the amino acid sequence of SEQ ID NO: 2 or SEQ ID NO: 4

In another embodiment, the invention provides an isolated polypeptide having at least about 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or more identity (e.g., when compared to the overall length of the amino acid sequence) to the amino acid sequence shown in SEQ ID NO: 2 or SEQ ID NO:4.

In a further aspect, the invention provides a bacterial host cell comprising the isolated nucleic acid molecules encoding dihydrolipoamide dehydrogenase polypeptides or fragments thereof.

In one embodiment, the bacterial host cell comprises a vector comprising the nucleotide sequence of SEQ ID NO: 1 or SEQ ID NO: 3, or a fragment thereof. In another embodiment, the bacterial host cell comprises the vector is pKY33.

The invention also provides a method for producing a polypeptide selected from the group consisting of:
 a) a polypeptide comprising the amino acid sequence SEQ ID NO: 2 or SEQ ID NO: 4;
 b) a fragment of a polypeptide comprising the amino acid sequence of SEQ ID NO: 2 or SEQ ID NO: 4; wherein the fragment comprises at least 15 contiguous amino acids of SEQ ID NO: 2 or SEQ ID NO: 4; and
 c) a naturally occurring allelic variant of a polypeptide comprising the amino acid sequence of SEQ ID NO: 2 or SEQ ID NO: 4,
wherein the polypeptide is encoded by a nucleic acid molecule which hybridizes to a complement of a nucleic acid molecule comprising SEQ ID NO: 1 or SEQ ID NO: 3, under stringent conditions;
comprising culturing bacterial host cells containing the isolated nucleic acid molecules encoding dihydrolipoamide dehydrogenase polypeptides or fragments thereof, under conditions in which the nucleic acid molecule is expressed.

In one embodiment, the LPD polypeptide or gene product is derived from a non-recombinant ethanologenic Gram-positive or Gram-negative bacterium. In exemplary embodiments, the LPD polypeptide or gene product is derived from an ethanologenic Gram-negative microorganism selected from the group consisting of *Acinetobacter, Gluconobacter, Escherichia, Geobacter, Shewanella, Salmonella, Eneterobacter* and *Klebsella*.

In another embodiment, the LPD polypeptide or gene product is derived from an ethanologenic Gram-positive microorganism selected from the group consisting of *Bacillus, Clostridium, Corynebacterium, Lactobacillis, Lactococcus, Oenococcus, Streptococcus* and *Eubacterium*.

Included within the scope of the present invention are LPD polypeptides or gene products that are *Escherichia coli* derived polypeptides or gene products encoded by naturally occurring bacterial genes. Further included within the scope of the present invention are bacterial-derived polypeptides or gene products which differ from naturally-occurring bacterial and/or *Escherichia coli* genes (e.g., lpd), for example, genes which have nucleic acids that are mutated, inserted or deleted, but which encode polypeptides substantially similar to the naturally-occurring gene products of the present invention, e.g., comprise a dihydrolipoamide dehydrogenase activity.

It is well understood that one of skill in the art can mutate (e.g., substitute) nucleic acids which encode for conservative amino acid substitutions. It is further well understood that one of skill in the art can substitute, add or delete amino acids to a certain degree without substantially affecting the function of a gene product (e.g., dihydrolipoamide dehydrogenase) as compared with a naturally-occurring gene product, each instance of which is intended to be included within the scope of the present invention.

Included within the scope of the invention are non-recombinant bacterium comprising an lpd gene comprising a mutation, wherein the substitution is a mutation of H at position 322, or E at position 354, in the wild type lpd gene (SEQ ID NO: 6), to any amino acid, such that the amino acid alters the acidity of the region. In further embodiments, the amino acid is a neutral charged amino acid at physiological pH. In yet further embodiments, the amino acid is a basic charged amino acid at physiological pH.

In an embodiment, an isolated polypeptide of the present invention (e.g., an isolated dihydrolipoamide dehydrogenase enzyme) has an amino acid sequence shown in SEQ ID NO: 2 or SEQ ID NO: 4. In other embodiments, an isolated polypeptide of the present invention is a homologue of at least one of the polypeptides set forth as SEQ ID NO: 2 or SEQ ID NO: 4 (e.g., comprises an amino acid sequence at least about 30-40% identical, advantageously about 40-50% identical, more advantageously about 50-60% identical, and even more advantageously about 60-70%, 70-80%, 80-90%, 90-95% or more identical to the amino acid sequence of SEQ ID NO: 2 or SEQ ID NO: 4, and has an activity that is substantially similar to that of the polypeptide encoded by the amino acid sequence of SEQ ID NO: 2 or SEQ ID NO: 4, respectively.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), advantageously taking into account the number of gaps and size of the gaps necessary to produce an optimal alignment.

The comparison of sequences and determination of percent identity between two sequences can be accomplished using a mathematical algorithm. A particular, non-limiting example of a mathematical algorithm utilized for the comparison of sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs (version 2.0) of Altschul, et al. (1990) *J. Mol. Biol.* 215:403-410. BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul, et al. (1997) *Nucleic Acids Research* 25(17):3389-3402. When utilizing BLAST and Gapped BLAST programs, the default parameters of the respective programs (e.g., XBLAST and NBLAST) can be used. See http://www.ncbi.nlm.nih.gov. Another particular, non-limiting example of a mathematical algorithm utilized for the comparison of sequences is the algorithm of Myers and Miller (1988) *Comput Appl Biosci.* 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

For example, in one embodiment of the invention the percent identity between two amino acid sequences is determined using the Blast server at NCBI or ClustalW at the European Biotechnology Institute. For instance, the amino acid sequence of dihydrolipoamide dehydrogenase from various organisms is compared to that of *E. coli* Lpd protein, and the percent identity of a specific sequence to that of the *E. coli* sequence can be obtained from either of the two databases. Table 7 and FIG. 9 illustrate these comparisons. The values in parenthesis represent the total similarity of the specific protein to that of the *E. coli* Lpd and include both the amino acid positions that are identical as well as the positions at which a conservative substitution occurred. For *Bacilus subtilis*, two dihydrolipoyl dehydrogenases, one from the PDH complex and the other from acetoin dehydrogenase, were included, for comparison.

One of ordinary skill in the art will recognize that based on the aforementioned calculations, there is a high degree of conservancy in LPD among a range of bacterial species, including bacteria that are far removed from each other phylogentically (based on 16S ribosomal RNA(DNA) sequence), such as, e.g., Gram-positive and Gram-negative bacteria, arcbaea and *Streptomyces*.

The enzyme puruvate dehydrogenase is found in all aerobic organisms and is the pivotal enzyme in the conversion of glucose to energy. Dihydrolipoamide dehydrogenase (Lpd) is one of the three subunits of the PDH complex. The Lpd contains two unique motifs: a flavin binding motif (amino acids 15-45) and a pyridine nucleotide-disulfide oxidoreductase motif (amino acids 347-456) (*E. coli* Lpd numbering). The amino acid sequences of the Lpd proteins from several organisms have significant homology due to their unique role in PDH complex The amino acid sequence identity between *E. coli* Lpd and other bacterial Lpds ranges from 30% to 99%. In the extreme case of the Lpd from *E. coli* and Human, 42% of the amino acids in the sequence are identical. In the flavin binding region of the Lpd (amino acids 15-45), this sequence identity increases to 67%. In one sub-section of this sequence of 18 amino acids (positions 28-55), all but one amino acid is conserved in the Lpd sequences of *E. coli*, human and mouse. Histidine at 322 and glutamate at 354 are also conserved among these proteins. Due to this very high degree of sequence conservation, *E. coli* Lpd mutations that are described in the present disclosure are expected to have similar phenotypes upon introduction into the Lpd proteins from other organisms. Thus, the methods of the invention are not limited to the strains taught herein.

IV. Methods of Making Non-Recombinant Bacterium

A further aspect of the invention provides a non-recombinant bacterium comprising a lpd gene having one or more mutations, wherein the mutation renders the non-recombinant bacterium capable of producing ethanol as the primary fermentation product under anaerobic conditions, and wherein the bacterium is prepared by a process comprising the steps of:
a) growing a candidate mutant strain of the bacterium under anaerobic growth conditions in sugar-rich medium; and
b) selecting mutants that produce ethanol as the major product of fermentation.

In one embodiment of the method, the ethanol produced comprises greater than 50% of total non-gaseous fermentation products under anaerobic conditions.

In another aspect, the invention provides a method of producing the ethanologenic non-recombinant bacteria of the invention comprising the steps of:
a) growing a candidate mutant strain of the bacterium under anaerobic growth conditions in sugar-rich medium; and
b) selecting mutants that produce ethanol as the major product of fermentation.

In embodiments of the foregoing methods and processes of the invention, the sugar in the sugar-rich medium is selected from the group consisting of glucose, xylose, arabinose, mannose, galactose, sucrose, and lactose. In one embodiment of the present invention, the non-recombinant bacterium having the aforementioned attributes is also ethanologenic. Accordingly, the invention provides methods for making the ethanologenic non-recombinant bacterium. Further, the invention provides methods for screening for the desired ethanologenic phenotype.

The parent strain of the invention is characterized by a low level of ethanol production under anaerobic conditions, when grown in sugar rich medium. An example of such a strain could be strain AH242; however, any strain that is characterized by low levels of ethanol production under anaerobic conditions is suitable for use in the method. Further mutation of the parent strain according to known methods in the art (Dastenko and Wanner, 2000. Proc. Natl. Acad. Sci. USA 97:6640-6645.) are carried out to render the parent strain incapable of anaerobic growth (defective) in all media. Additionally, a cassette for antibiotic resistance is added for selection purposes, according to practice well known in the art.

Typically, selection is carried out by culturing the growth defective strain in aerobic conditions until mid exponential phase of growth is reached, spreading the culture on agar, and exposing the culture to mutagenizing agent. One of ordinary skill in the art will recognize that a number of mutagenizing agents can be used, including ethyl methane sulfonate, 2-aminopurine, ICR-191, methyl methane sulfonate, N-methyl-N'-nitro-N-nitrosoguanidine, or any other agent known to cause a change in nucleotide sequence. After exposure to mutagenizing agents in anaerobic conditions, the cultures are switched to aerobic conditions, then back to anaerobic conditions. Colonies that grew were chosen and streaked on to fresh plates and grown under anaerobic conditions. Each colony can be separately cultured and grown on the appropriate antibiotic plate to confirm that the mutant carries the antibiotic resistance of the parent. One of ordinary skill in the art will understand that bacterial culture procedures are carried out according to protocol standard to the art.

High performance liquid chromatography can be used to determine the yield of fermentation products in the spent medium of the isolated mutants. For example, ethanol, acetate, formate and succinate can be detected by HPLC.

One of ordinary skill in the art can recognize that based on the aforementioned examples, and based on homology among bacterial strains, the methods of the instant invention are not limited to the strains taught in the instant application.

V. Methods for Producing Ethanol

In another aspect, the invention provides a method for producing ethanol from an oligosaccharide source. The method comprises contacting the oligosaccharide with a non-recombinant bacterium or host cell of the invention as described above, to thereby produce ethanol from an oligosaccharide source. In a particular embodiment of the method, the oligosaccharide is selected from the group consisting of lignocellulose, hemicellulose, cellulose, pectin and any combination thereof.

The host cell of the invention is characterized by a low level of ethanol production under anaerobic conditions. Wild type *E. coli* produces ethanol and acetate at a ratio of 1:1 during anaerobic growth. During stationary phase of growth, wild type *E. coli* produces lactate as the main product, and the fraction of ethanol in the total fermentation products is about 20%. The products in all these fermentations comprise various acids, thus leading to the term, mixed acid fermentation. In one aspect, the instant invention provides a non-recombinant bacterium comprising an lpd gene having one or more mutations, wherein the mutation renders the non-recombinant bacterium capable of producing ethanol as the primary fermentation product under anaerobic conditions. The primary fermentation product is intended to include non-gaseous products of fermentation that comprise greater than 50% of total non-gaseous product. The primary fermentation product is the most abundant non-gaseous product.

Typically, fermentation conditions are selected that provide an optimal pH and temperature for promoting the best growth kinetics of the producer host cell strain and catalytic conditions for the enzymes produced by the culture (Doran, et al., (1993) *Biotechnol. Progress.* 9:533-538). For example, for *Klebsiella*, e.g., the P2 strain, optimal conditions were determined to be between 35-37° C. and pH 5.0-pH 5.4. Under these conditions, even exogenously added fungal endoglucanases and exoglucanases are quite stable and continue to function for long periods of time. Other conditions are discussed in the Examples. Moreover, it will be appreciated by the skilled artisan, that only routine experimentation is needed, using techniques known in the art, for optimizing a given fermentation reaction of the invention. See, for example, U.S. Pat. Nos. 5,424,202 and 5,916,787, which are specifically incorporated herein by this reference.

In yet another aspect, the invention provides a kit comprising a non-recombinant bacterium or host cell of the invention as described above, and instructions for producing ethanol in accordance with the methods and processes described herein. In one embodiment, the kit comprises a sugar source.

VI. Exemplification

The invention is further illustrated by the following examples, which should not be construed as limiting. Throughout the examples, the following materials and methods are used unless otherwise stated.

Materials and Methods

Bacterial Strains

*E. coli* K-12 strain W3110 (ATCC 27325) and a derivative, strain AH242, represented by a deposit with the Agricultural Research Culture Collection and designated as deposit number NRRL B-30967 (ΔldhA and Δ(focA-pflB)), were used in this study. Strain SE2378 is an ethanologenic mutant of strain AH242. Deletion of the genes pflB, adhE, mgsA and aceF were as per Dastenko, et al. The ldhA deletion strain was constructed after introduction of transposon Tn10 into ldhA followed by selection in fusaric acid medium (Klekner, et al. 1991; Maloy, et al. 1981). Construction of the other strains utilized standard genetic and molecular biology techniques (Maniatis, et al. 1982; Miller, et al. 1972). The genotypes of the strains used herein are listed in Table 1, shown below.

TABLE 1

Bacterial strains and Relevant Genotype

| Strain | Relevant Genotype | Source |
|---|---|---|
| W3110 | Wild type | ATCC 27325 |
| AH240 | Δ(focA-pflB)-FRT-Km-FRT | This study |
| AH241 | Δ(ldhA) | This study |
| AH242 | Δ(ldhA) Δ(focA-pflB)-FRT-Km-FRT | This study |
| SE2378 | AH242, Anaerobic growth-plus | This study |
| YK1 | SE2378, Km$^s$ | This study |
| YK29 | AH242, Km$^s$ | This study |
| YK91 | YK1, Δ(adhE)-FRT-Km-FRT | This study |
| YK93 | YK1, Δ(aceF)-FRT-Km-FRT | This study |
| YK96 | YK1, Δ(mgsA)-FRT-Km-FRT | This study |
| YK152 | YK29, Δ(aceF)-FRT-Km-FRT | This study |
| YK153 | W3110, Δ(aceF)-FRT-Km-FRT | This study |
| YK157 | YK152, aceF$^+$ (W3110) | YK152 × P1(W3110) |
| YK158 | YK152, aceF$^+$ (SE2378) | YK152 × P1(SE2378) |

Growth Medium and Fermentation

Rich medium (L-broth) contained (per liter), trypticase peptone (10 g), yeast extract (5 g) and NaCl (5 g) (Lee, et al. 1985). Mineral salts medium was described previously (Lee, et al. 1985) Glucose or xylose was added as needed. Fermentations were conducted at 37° C. as described previously (Hasona, et al. 2004). Culture pH was maintained at 7.0 by the addition of KOH. Batch fermentations were conducted in 13×100 mm screw cap tubes filled to the top as previously described (Patel, et al. 2006)

Vectors and Transformation

Cloning and expression of lpd as well as the genes in the pdh region is accomplished according to standard procedures described in the art. Vectors employed in transformation can include pTrc99a (GE), pCR2.1-TOPO, pBR322, pUC19, pACYC184, pBAD24, in addition to other commonly known vectors. A CaCl$_2$ based chemical transformation method was used, according to standard procedure found in Maniatis, et al. (1989).

Analytical Methods

Sugars and fermentation products were determined by HPLC (Underwood, et al. 2002). Pyruvate decarboxylase activity was measured in disrupted cell preparations as previously described (Talarico, et al. 2001).

EXAMPLE 1

Isolation of Ethanologenic Non-Recombinant *E. coli* Strains SE2377, SE2378, SE2382, SE2383, SE2384, SE2385

In this example, the isolation of non-recombinant ethanologenic strains of the bacterium *E. coli* is described.

The starting strain AH242 was used for isolation of the described homoethanologenic mutants of *Escherichia coli*. Strain AH242 is incapable of anaerobic growth in rich medium containing sugars due to mutations in the ldh and pflB genes encoding lactate dehydrogenase (LDH) and pyruvate formate lyase (PFL), respectively (Mat-Jan, et al. 1989). Despite these mutations, the aerobic growth of AH242 remains unaffected. The anaerobic growth defect in AH242 is a result of a deficiency in the re-oxidation of NADH to NAD$^+$, an essential substrate for the key glycolytic enzyme glyceraldehyde-3-phosphate debydrogenase, and the associated ATP production. The absence of LDH eliminates NADH oxidation by the reduction of pyruvate to lactate. In the absence of acetyl CoA that is normally produced by PFL, there is insufficient acetyl CoA available for effective NADH oxidation by native aldehyde, and alcohol dehydrogenase activities.

In the instant invention, starting with the AH242 strain, the focA- and -pflB (pyruvate formate lyase) deletion was constructed using previously described methods (Datsenko and Wanner, 2000). The single deletion mutants, AH240, -(focA-pflB) and AH241-(ldhA) were the parent strains of the double mutant AH242 strain. At the location of deletion, the FRT-Km-FRT cassette was inserted, thus rendering strain AH242 kanamycin-resistant. Due to the two mutations, strain AH242 is anaerobic growth defective in all media. Table 2, below, lists the growth characteristics of the *E. coli* mutants with mutations in anaerobic fermentation pathways.

TABLE 2

Growth characteristics of *E. coli* mutants with mutations in anaerobic fermentation pathways.

| | | Specific growth rate (h$^{-1}$) | | | | | |
|---|---|---|---|---|---|---|---|
| | | Aerobic | | | Anaerobic | | |
| Strain | Genotype | LB | Minimal | Minimal (+Ace, Succ) | LB | Minimal | Minimal (+Ace, Succ) |
| W3110 | wild type | 1.31 | 1.05 | 0.97 | 0.98 | 0.51 | 0.51 |
| AH240 | pflB | 1.23 | 0.95 | 0.99 | 0.79 | NG | 0.26 |
| AH241 | ldhA | 1.35 | 0.96 | 0.94 | 0.81 | 0.39 | 0.30 |
| AH242 | pflB, ldhA | 1.21 | 1.18 | 0.97 | NG | NG | NG |
| SE2378 | pflB ldhA, Ana$^+$ | 1.18 | 0.51 | 0.82 | 0.46 | NG | NG (0.21) |

LB, L-broth;
Minimal - glucose minimal medium supplemented without or with acetate and succinate (1 mg/ml each).
NG—No growth.
Value in parenthesis was the growth rate in glucose-minimal medium with acetate, succinate and glutamate (1 mg/ml).

The resulting anaerobic growth defective strain AH242 was cultured in 5 ml L-broth in aerobic conditions, at 37° C., in a shaker at 200 RPM. At mid-exponential phase of growth, the culture was removed from the shaker and spread on L-agar with glucose, or L-agar with glucose plus a redox dye of neutral red. A Whatman paper filter was placed on the surface of each of the agar medium. The mutagenizing agent ethyl methane sulfonate (EMS) was added to the disc, and the plates were transferred to an anaerobic jar containing an H$_2$+CO$_2$ generator envelope with palladium catalyst to create an O$_2$ free environment. Other standard agents suitable for use in mutagenesis can be employed in the invention. The anaerobic jar with the plates was incubated at 37° C. for 5 days.

After 5 days no visible growth was detected on either of the indicated media. Subsequently, both dishes were incubated under aerobic conditions for ~20 hours. At the end of this incubation, a lawn of bacterial cells was observed in both media in all areas except the area surrounding where the paper disc with EMS was placed. Cells on the surface of each media were transferred to fresh media of the same composition by replica plating and placed in an anaerobic jar for 5 days. After 5 days, each plate had over 100 colonies in all areas except for where the EMS was placed. 31 colonies were chosen from each of the glucose (15 colonies) and glucose+neutral red plates (16 colonies) and streaked on fresh L-agar+glucose. The plates were grown under anaerobic conditions. All colonies grew under anaerobic conditions.

31 mutants were inoculated to L-broth+glucose cultures, and after growth each was transferred to the surface of L-agar+kanamnycin plates. All mutants grew in the presence of kanamycin, indicating they carried the antibiotic resistance of the parent strain AH242.

The 31 mutants were transferred to L-broth+glucose in screw cap tubes, and incubated at 37° C. without mixing. After visible growth was detected, the medium was separated from the cells, and the fermentation products in the spent medium were determined using high performance liquid chromatography (Underwood, et al., 2002). Table 3 shows that thirty of the thirty-one mutants produced ethanol as the primary, or major fermentation product (73%). The remaining product was a combination of succinate and acetate.

These results show that non-recombinant mutants from the AH242 parent strain, that is incapable of growth in an anaerobic environment, have been isolated that are capable of growth in anaerobic conditions, and produce ethanol as the major fermentation product.

TABLE 3

Fermentation profiles of ethanologenic mutant derivatives of E. coli strain AH242

| Isolate Number | Glucose Consumed (mM) | Fermentation Products (mM) | | | | | Total Product | |
|---|---|---|---|---|---|---|---|---|
| | | Succinate | Lactate | Formate | Acetate | Ethanol | Ethanol % | Yield (%) |
| SE2138 | 19.7 | 3.7 | 22.0 | 3.5 | 7.2 | 8.2 | 20 | |
| 1 | 19.7 | 2.8 | — | — | 3.1 | 31.1 | 84 | 90 |
| 2 | 18.7 | 2.1 | — | — | 3.1 | 28.4 | 84 | 94 |
| 3 | 19.7 | 2.7 | — | — | 3.6 | 30.6 | 83 | 92 |
| 4 | 19.7 | — | — | — | 5.4 | 30.7 | 85 | 92 |
| 5 (SE2383) | 19.7 | 3.3 | — | — | 3.9 | 29.4 | 80 | 93 |
| 6 | 19.7 | 2.9 | — | — | 3.0 | 30.8 | 84 | 93 |
| 7 | 19.7 | 1.7 | — | — | 4.8 | 30.3 | 82 | 93 |
| 8 | 19.7 | 2.8 | 0.5 | 3.3 | 3.4 | 26.8 | 81 | 85 |
| 9 | 19.7 | 2.4 | — | — | 3.1 | 30.4 | 85 | 91 |
| 10 (SE2384) | 5.6 | 2.0 | — | — | 2.6 | 5.8 | 56 | 93 |
| 11 | 19.7 | 2.8 | — | — | 3.2 | 32.0 | 84 | 96 |
| 12 | 19.7 | 3.3 | 0.2 | — | 3.0 | 30.7 | 83 | 94 |
| 13 | 19.7 | 2.5 | 0.2 | — | 2.4 | 32.4 | 86 | 95 |
| 14 (SE2376) | 19.7 | 2.3 | — | — | 2.9 | 33.3 | 86 | 98 |
| 15 (SE2385) | 19.7 | 2.6 | — | — | 3.1 | 32.7 | 85 | 98 |
| 17 | 15.0 | 1.8 | — | — | 2.4 | 24. | 85 | 96 |
| 18 (SE2377) | 19.7 | 2.3 | — | 2.7 | 4.0 | 31.2 | 83 | 95 |
| 19 (SE2378) | 19.7 | 2.6 | — | — | 2.7 | 33. | 86 | 98 |
| 20 | 9.9 | 0.9 | 7.6 | — | 2.2 | 11.4 | 52 | 100 |
| 21 | 19.5 | 1.9 | — | — | 2.6 | 31.9 | 88 | 93 |
| 22 | 19.7 | 2.5 | 4.9 | — | 2.9 | 28.2 | 73 | 98 |
| 23 | 19.7 | 2.6 | — | — | 2.9 | 33.2 | 86 | 98 |
| 24 | 19.7 | 2.5 | 3.8 | — | 3.0 | 29.2 | 76 | 98 |
| 25 | 19.7 | 3.1 | — | — | 2.7 | 32.6 | 85 | 98 |
| 26 | 19.7 | 2.4 | 4.5 | — | 2.7 | 27.4 | 74 | 93 |
| 27 | 19.7 | 2.1 | 0.2 | — | 2.5 | 32.0 | 87 | 93 |
| 28 | 18.7 | 3.3 | 0.6 | 3.5 | 4.9 | 26.3 | 78 | 90 |
| 29 | 19.7 | 3.1 | — | — | 3.6 | 32.2 | 81 | 100 |
| 30 | 14.5 | 2.1 | — | — | 2.8 | 23.5 | 83 | 98 |
| 31 (SE2382) | 19.7 | 2.3 | — | — | 2.8 | 32.8 | 87 | 96 |
| 32 | 19.7 | 2.9 | — | — | 3.0 | 32.0 | 84 | 96 |

EXAMPLE 2

Growth Rate and Fermentation Profile of Ethanologenic Non-Recombinant Bacterium

In this example, the growth rate and fermentation profile of ethanologenic non-recombinant bacterium are described. From the above studies, mutant strain SE2378, which is capable of growth in anaerobic conditions, and produces ethanol as the major fermentation product, was selected for further study.

Growth Characteristics

Growth characteristics of E. coli mutants with mutations in anaerobic fermentation pathways were examined. Aerobic growth of strain SE2378 was comparable to the wild type E. coli strain W3110 or any of the single or double (focA-pflB) or ldhA mutants when cultured in rich medium as described in Table 2, above. In minimal medium, the aerobic growth rate of strain SE2378 was about half of the parent strain AH242. Supplementation of the growth medium with acetate and succinate restored the growth rate to near that of the parent. Although strain SE2378 grew anaerobically, the growth rate, even in rich medium, was only about 50% of that of the AH240 and AH241 single mutants (see Table 2, above). Strain SE2378 did not grow anaerobically in glucose-minimal medium, a phenotype associated with the pflB mutation (Clark, et al. 1989). Supplementation of the minimal medium with acetate supported the growth of the pflB mutant, strain AH240, but not the ethanologenic derivative strain SE2378. Strain SE2378 also required glutamate in addition to acetate for anaerobic growth in glucose-minimal medium. Previous studies have shown that the ethanologenic *Escherichia coli* strain KO11 also requires glutamate for optimum fermentation of xylose (Underwood, et al. 2004). This glutamate requirement can be overcome by the addition of a protective osmolyte, betaine, to the medium. However, the glutamate requirement for anaerobic growth of strain SE2378 in minimal medium was not suppressed by betaine, indicating a biosynthetic deficiency in acetyl-CoA flux to 2-ketoglutarate, a precursor of glutamate, rather than an osmotic requirement. It is thought that the acetyl-CoA was rapidly converted to ethanol by this ethanologen, and that acetyl-CoA is rate-limiting for biosynthesis. With these supplements, the growth rate of strain SE2378 in minimal medium reached that of the pflB parent strain, AH240. Corn steep liquor, a low cost medium supplement, replaced glutamate for growth of strain SE2378 in glucose-minimal medium.

Glucose Fermentations

In pH controlled fermentations with 50 g l$^{-1}$ glucose (Hasona, et al., 2004), strain SE2378 grew with a specific growth rate of 0.46 h$^{-1}$ after a lag of about 6 hours, and produced ethanol as the primary product (FIG. 3 and Table 4, below). Since the immediate parent strain, AH242 is unable to grow anaerobically, the fermentation of strain SE2378 was compared to that of wild type strain W3110. W3110 completed the fermentation of 50 g l$^{-1}$ glucose in 24 hours, while the mutant strain required about 72 hours. This difference can be primarily attributed to a difference in cell density (2.5 mg/ml dry wt for the wild type versus 1.7 mg/ml dry wt for the mutant) and the maximum specific rate of sugar metabolism of the two strains (4.1 to 3.3 g glucose h$^{-1}$ g cells$^{-1}$ for the wild type and the mutant, respectively; Table 5 below). Strain SE2378 produced about 480 mmol l$^{-1}$ ethanol (22 g l$^{-1}$), 88% of the total products which included small amounts of acetate, lactate and succinate. This is in contrast to wild type W3110 fermentations in which ethanol represented only 27% of the products at 6.6 g l$^{-1}$ (Table 4) The maximum specific productivity observed for strain SE2378 was 1.34 g h$^{-1}$ g cell$^{-1}$ (Table 5) comparable to the value of 1.6 g h$^{-1}$ g cell$^{-1}$ reported for batch fermentations with yeast (Smits, et al., 2000).

TABLE 5

Growth and Ethanol production by *E. coli* strain SE2378 grown on Glucose or Xylose.

|  | W3110 | | SE2378 | |
|---|---|---|---|---|
|  | Glucose | Xylose | Glucose | Xylose |
| $\mu_{Max}$ | 0.44 | 0.37 | 0.46 | 0.38 |
| $Y_{X/S}$ | 0.04 | 0.04 | 0.04 | 0.04 |
| $Q_S$ | 2.94 | 1.58 | 1.29 | 1.65 |
| $Q_P$ | 0.50 | 0.36 | 0.61 | 0.53 |
| $Y_{P/S}$ | 0.12 | 0.18 | 0.41 | 0.42 |
| $q_S$ | 4.10 | 4.93 | 3.26 | 5.33 |
| $q_P$ | 0.49 | 0.89 | 1.34 | 2.24 |

Abbreviations: $\mu_{Max}$, specific growth rate, h$^{-1}$; $Y_{X/S}$, g cells (g substrate)$^{-1}$; $Q_S$, g sugar consumed L$^{-1}$ h$^{-1}$; $Q_P$, g ethanol L$^{-1}$ h$^{-1}$; $Y_{P/S}$, g ethanol (g substrate)$^{-1}$; $q_S$, g sugar consumed (g cell dry weight)$^{-1}$ h$^{-1}$; $q_P$, g ethanol (g cell dry weight)$^{-1}$ h$^{-1}$ Xylose Fermentations Both the wild type W3110 and the mutant SE2378 strain grew at similar rates during anaerobic fermentation with 50 g l$^{-1}$ xylose, although strain SE2378 lagged by approximately 8 hours (FIG. 3 and Tables 4 and 5, above). Specific growth rates on xylose were 80% of those with glucose, consistent with previously published reports (Gonzalez, et al. 2002). The mutant strain fermented xylose more rapidly than the wild type W3110. After 48 hours, xylose utilization exceeded glucose utilization for strain SE2378. Approximately 88% of the fermentation products recovered with strain SE2378 was ethanol; 20 g l$^{-1}$ from 50 g l$^{-1}$ of xylose. The maximum specific productivity of ethanol for strain SE2378 with xylose was 2.23 g h$^{-1}$ g cells$^{-1}$.

The specific ethanol productivity of both W3110 and SE2378 was higher with xylose than with glucose, as shown in Table 5. This may be indicative of the lower energy yields from xylose metabolism (Hasona, et al., 2004). For wild type, the net ATP yield from xylose is only about 1.5 per xylose, as compared to 3.0 per glucose. This would require that cells use more xylose to produce the same amount of cell mass. However the specific rate of xylose consumption by the wild type was only slightly higher than that of glucose (4.93 vs. 4.10 g h$^{-1}$ g cells$^{-1}$), as seen in Table 5 above, thus accounting for the lower cell yield and the longer fermentation time compared to glucose fermentation. In contrast, strain SE2378 lacks pyruvate formate lyase, an enzyme that is critical for xylose fermentation in minimal medium (Hasona, et al. 2004). Due to this mutation, the net calculated ATP yield from xylose fermentation in strain SE2378 is only 0.67 per xylose. It is apparently this lower ATP yield that is driving the high xylose

TABLE 4

Fermentation characteristics of *E. coli* strain SE2378 and wild type strain W3110[a]

| Strain | Glucose Consumed (mM) | Products (mM) | | | | | Ethanol Yield[b] | Total Product Yield[c] |
|---|---|---|---|---|---|---|---|---|
|  |  | Ethanol | Acetate | Formate | Lactate | Succinate |  |  |
| Glucose fermentation | | | | | | | | |
| W3110 | 298 ± 19 | 142 ± 6 | 162 ± 6 | 206 ± 11 | 206 ± 11 | 18 ± 0.7 | 0.24 ± 0.01 | 0.89 ± 0.05 |
| SE2378 | 296 ± 4 | 478 ± 15 | 27 ± 2 | 0 | 13 ± 2 | 27 ± 2 | 0.81 ± 0.02 | 0.92 ± 0.04 |
| Xylose fermentation | | | | | | | | |
| W3110 | 333 ± 8 | 191 ± 7 | 215 ± 10 | 248 ± 53 | 32 ± 3 | 57 ± 1 | 0.34 ± 0.00 | 0.89 ± 0.02 |
| SE2378 | 325 ± 2 | 444 ± 9 | 25 ± 2 | 0 | 0 | 33 ± 5 | 0.82 ± 0.01 | 0.93 ± 0.02 |

[a]Fermentations were conducted in L-broth supplemented with 50 gl$^{-1}$ sugar at pH 7.0 and 37° C.
[b]Ethanol yields as a fraction of the theoretical maximum (0.51 g ethanol per g sugar).
[c]Ethanol as a molar fraction of total products per mole of glucose fermented.

flux in this ethanologenic mutant. The specific productivity of ethanol from xylose of 2.23 g h$^{-1}$ g cells$^{-1}$ is higher than the value of 1.6 g h$^{-1}$ g cells$^{-1}$ on glucose for yeast (Smits, et al. 2000) and for glucose and xylose in the ethanologenic E. coli strain KO11 carrying the Z. mobilis pdc and adh genes (about 2 g h$^{-1}$ g cells$^{-1}$).

These results show that the non-recombinant SE2378 mutant produces ethanol as the primary fermentation product from both glucose and xylose. Further, the rate of ethanol production is comparable to other ethanologenic organisms.

EXAMPLE 3

Identification of Mutant Lpd Gene from Non-Recombinant Ethanologenic E. coli In this example, the identification of mutant LPD gene from E. coli strains SE2377, SE2378, SE2382, SE2383, SE2384, SE2385 is described.

Figure 5:
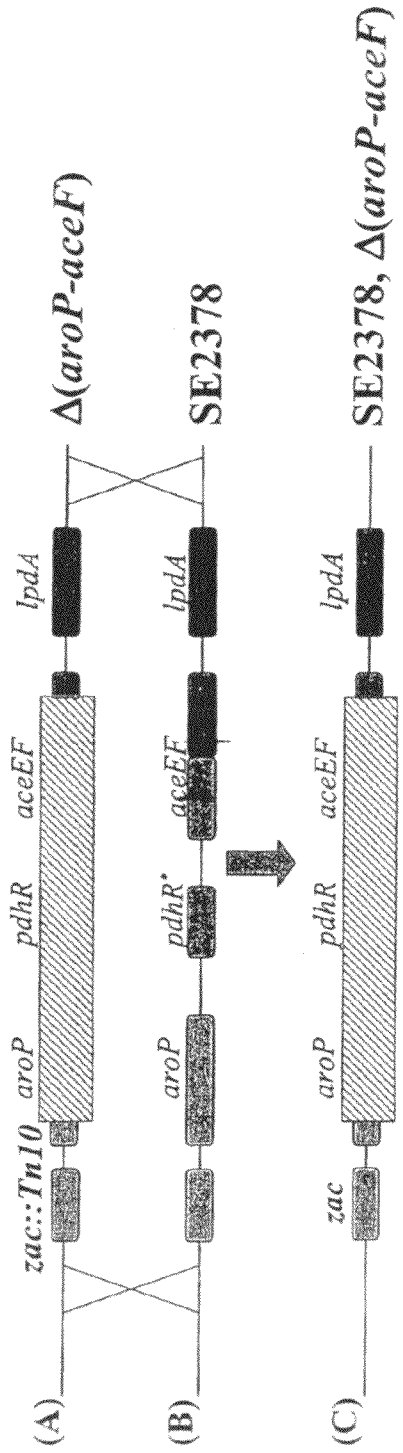
FIG. 5 shows the transduction of deletion mutant (aroP-aceEF) (A) (ΔaroP-aceEF) into strain SE2378 (B). Mutations in strain SE2378 were mapped by co-transduction with zac::Tn10. When aroP-pdhR-aceEF genes were deleted by co-transduction, the transductant (C) lost its ability to grow in LB containing 1% glucose under anaerobic conditions, while the same deletion in wild type background did not affect anaerobic growth.

Mutations in the non-recombinant ethanologenic E. coli mutant strains were mapped by co-transduction with zac::Tn10. When aroP-pdhR-aceEF genes were deleted by co-transduction (FIG. 5), the transductant lost its ability to grow in LB containing 1% glucose under anaerobic conditions, while the same deletion in wild type background did not affect anaerobic growth. These results suggest a role for pyruvate dehydrogenase enzyme in the anaerobic growth of strain SE2378. The mutation responsible for the ethanologenic phenotype in the SE2377, SE2378, SE2382, mutant strains identified mapped in the pyruvate dehyrogenase gene locus.

The pyruvate dehydrogenase complex (PDH) consists of three enzymes, pyruvate dehydrogenase/decarboxylase (enzyme 1, E1), lipoate transacetylase (enzyme 2, E2), and dihydrolipoamide dehydrogenase (enzyme 3, E3) subunits. It is known that the pdhR promoter is the promoter for the transcription of the pdhR-aceEF-lpd genes, despite the presence of independent promoters for aceEF and lpdA genes (Quail et al, 1995). Since the expression of the PDH operon is negatively regulated by pdhR protein (Quail, et al., 1995), the pdhR genes of SE2377, SE2378, SE2382 were sequenced (FIG. 6A). The sequence analysis of strain SE2378 revealed two mutations within the coding region of pdhR: 1 an amino acid substitution (S12P) and 1 amino acid insertion of leucine as amino acid 118. Another nucleotide substitution of G to A was found in the intergenic region between the pdhR gene and the aceE gene (FIG. 6B). Strain SE2377 and SE2382 did not carry any mutation in the pdhR-aceEF region of genomic DNA. However, these strains, as well as strains SE2383, SE2384 and SE2385, all had single mutations in the lpd gene (FIG. 5A). The PdhR protein is a pyruvate-responsive regulator of the pdhR-lpd operon and thus mutations in this protein are not unexpected. The aceEF may contain its own transcription start site for aceEF-lpd in addition to the start site at the beginning of the pdhR for transcription of pdhR-lpd. Thus, the mutations in the intergenic region may also support an elevated level of aceEF-lpd expression in the anaerobic cell. It has previously been reported that the level of pyruvate dehydrogenase/decarboxylase activity of PDH complex in E. coli is about 5-fold higher in cells grown aerobically vs. anaerobically (deGraef, et al., 1999).

These results provide location of the mutations in the identified ethanologenic E. coli strains of the instant invention.

EXAMPLE 4

Mutation in the Lpd Gene is Responsible for Ethanologenic Phenotype

In this example, mutation in the PDH complex, and specifically the lpd gene is shown to be causative for the ethanologenic phenotype.

Preliminary genetic analysis of strain SE2378 revealed that the mutation(s) responsible for anaerobic growth and homoethanol production are located in or near the genes coding for the PDH complex (pdh locus: pdhR, aceF, lpd). To confirm that PDH is required for the ethanologenic phenotype of strain SE2378, a mutation in the aceF gene (dihydrolipyl acetyltransferase; E2 enzyme of PDH) was transduced into strain YK1, a derivative of strain SE2378 that lacks the kanamycin-resistance gene. The transductant strain YK93, lost the ability to grow anaerobically, as shown in Table 6, below.

TABLE 6

Growth characteristics of ethanologenic E. coli strain SE2378 with a mutation in the pdh locus, (aceF)

| | | Specific growth rate (h$^{-1}$) | | | | |
|---|---|---|---|---|---|---|
| | | Aerobic | | | Anaerobic | |
| Strain | Genotype | LB | Minimal | Minimal (+Ace, Succ) | LB | Minimal |
| W3110 | wild type | 1.31 | 1.05 | 0.97 | 0.98 | 0.51 |
| YK153 | W3110, aceF | 0.46 | NG | 0.55 | 1.07 | 0.44 |
| YK29 | pflB, ldhA | 1.29 | 0.99 | 0.99 | NG | NG |
| YK152 | YK29, aceF | 0.83 | NG | 0.50 | NG | NG |
| YK1 | pflB, ldhA, Ana$^+$ | 1.14 | 0.51 | 0.83 | 0.41 | NG* |
| YK93 | YK1, aceF | 0.68 | NG | 0.46 | NG | NG |
| YK157 | YK152, aceF$^+$ (W3110) | 1.32 | 0.96 | 0.87 | NG | NG |
| YK158 | YK152, aceF$^+$ (SE2378) | 1.17 | 0.51 | 0.80 | 0.45 | NG* |

Minimal - glucose minimal medium supplemented without or with acetate and succinate (1 mg/ml each).

NG—No growth.

*The two ethanologenic derivatives require acetate and glutamate for anaerobic growth in minimal medium as of strain SE2378.

This anaerobic-minus phenotype of strain YK93 was similar to that of strain AH242, the parent of strain SE2378. Although an aceF mutant is aerobic-minus in minimal medium due to the cell's inability to produce acetyl co-A for biosynthesis, under anaerobic growth conditions this function is catalyzed by the PFL and thus, an aceF mutation does not affect anaerobic growth of E. coli (strain YK153, W3110 with aceF mutation, as shown in Table 6). Anaerobic growth of strain YK93 was defective in all of the media that was tested. The aceF mutation in strain YK152 was transduced to aceF+ by phage P1 with the gene from either W3110 (wild type) or SE2378 (ethanologen) and the transductants were selected for growth in minimal medium under aerobic conditions. The transductants were also tested for anaerobic growth and fermentation products. The transductants that received the aceF+ gene from the wild type strain W3110, grew aerobically in minimal medium but failed to grow anaerobically in any of the media tested due to the presence of ldhA and pflB mutations. All the transductants that received the aceF+ gene from strain SE2378 grew anaerobically and all the tested transductants produced ethanol as the main fermentation product. These results show that the ethanologenic phenotype of strain SE2378 requires intact pdh locus and PDH activity, and agree with a PDH-dependent pathway for ethanol production (see FIG. 8 C). In this pathway for homoethanol production, pyruvate is oxidatively decarboxylated to acetyl-coA by PDH and further reduced to acetylaldehyde and ethanol by the alcohol dehydrogenase (FIG. 8C). Deletion of either aceF (PDH-minus; strain YK93) that is required for acetyl-coA production or adhE (ADH minus; strain YK91), needed for ethanol production, resulted in anaerobic growth negative phenotype supporting the role of this pathway for homoethanol production and redox balance in strain SE2378 that is lacking fermentative lactate dehydrogenase and pyruvate formate lyase.

In the next set of experiments, the lpd gene is shown to be causative for the ethanologenic phenotype. The lpd gene from the wild type strain W3110, and from the ethanologenic mutant strain SE2378 were cloned in to an expression vector for the production of the LPD protein from the trc promoter with IPTG as inducer. These plasmids were transformed in to strain YK100 that carries three deletions: ldhA, (focA-pflB), and lpd. Beyond the three mutations, strain YK100 is similar to W3110 strain. Due to the three deletions, strain YK100 is defective for anaerobic growth in all media tested, and is defective for aerobic growth in minimal medium. As discussed previously, the pyruvate dehydrogenase complex (PDH) consists of three enzymes, pyruvate dehydrogenase/decarboxylase (enzyme 1), lipoate transacetylase (enzyme 2), and lipoamide dehydrogenase (enzyme 3). Aerobic growth of E. coli is impaired by a mutation in any one of the three components of the PDH complex.

Figure 7:
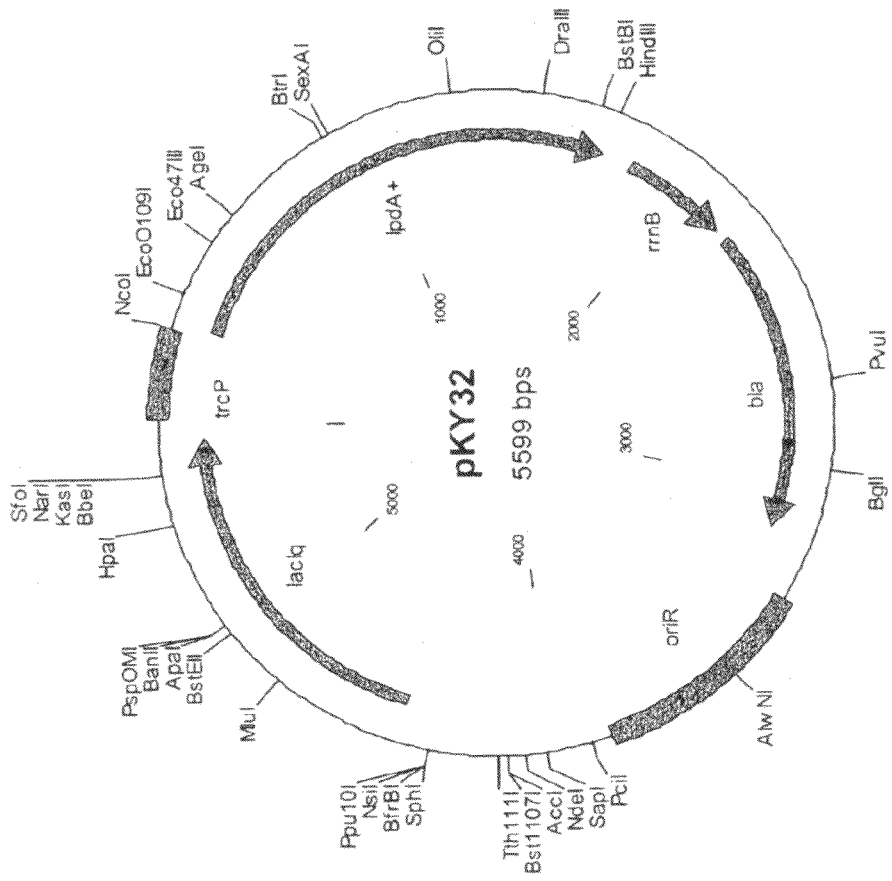
FIG. 7 shows plasmids used for expression of W3110 or SE2378 lpd in YK100 host. Plasmid pKY32 (A) contains the lpd gene from the wild type, strain W3110. Plasmid pKY33 (B) contains the lpd gene from the ethanologenic mutant SE2378.
Figure 7:
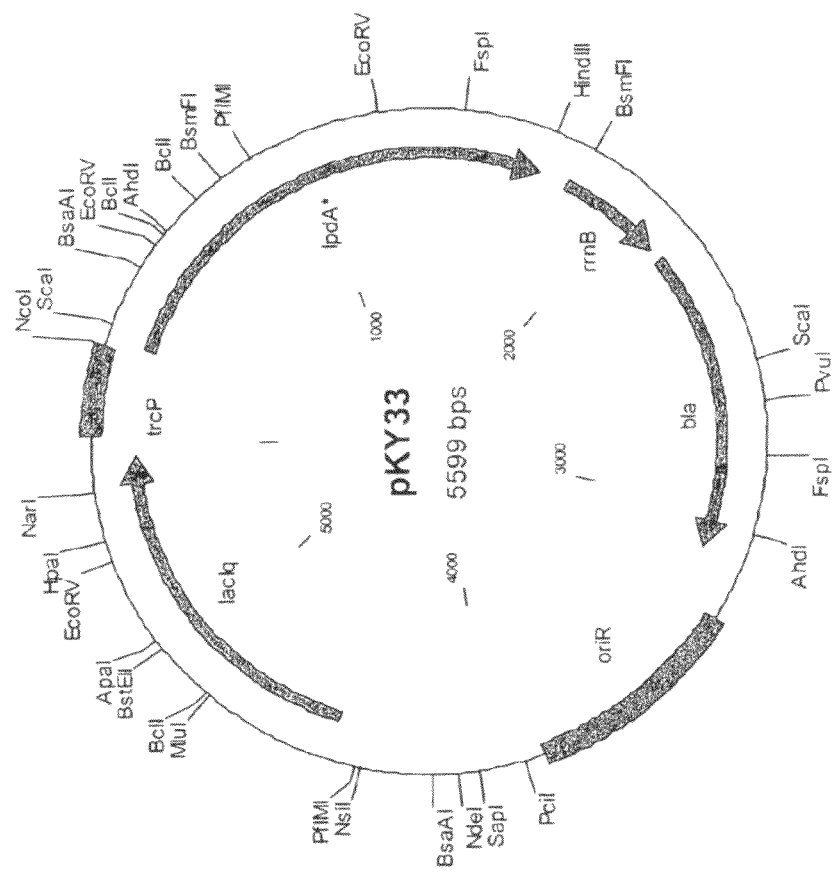

Plasmid pKY32 (FIG. 7A), containing the lpd gene (Lpd+) from strain W3110, or plasmid pKY33 (FIG. 7B) containing the mutant lpd gene (Lpd*) from strain SE2378, was transformed in to strain YK100, and ampicillin resistant transformants were selected. These transformants were PDH-positive as seen by aerobic growth in minimal medium; enzyme 1 and enzyme 2 of the PDH complex came from the chromosome and the Lpd came from the plasmid. Only the transformants with plasmid pKY33 carrying the lpd gene from the ethanologenic SE2378 strain were able to grow under anaerobic conditions. Ethanol was the major fermentation product in the spent medium from strain YK100/pKY33 (named YK129). In contrast, strain YK100 with plasmid pKY32 carrying the native lpd gene from W3110 did not grow under anaerobic conditions.

Taken together, these results show that the LPD protein is responsible for the observed activity of the pyruvate dehydrogenase complex under anaerobic growth conditions, and further that the mutated form of Lpd is sufficient to support homoethanol production by E. coli. The reason the lpd mutant of E. coli is ethanologenic is its ability to produce 4 NADH per glucose.

EXAMPLE 5

Mutation in the Lpd Gene is Responsible for NADH Insensitivty

Figure 10:
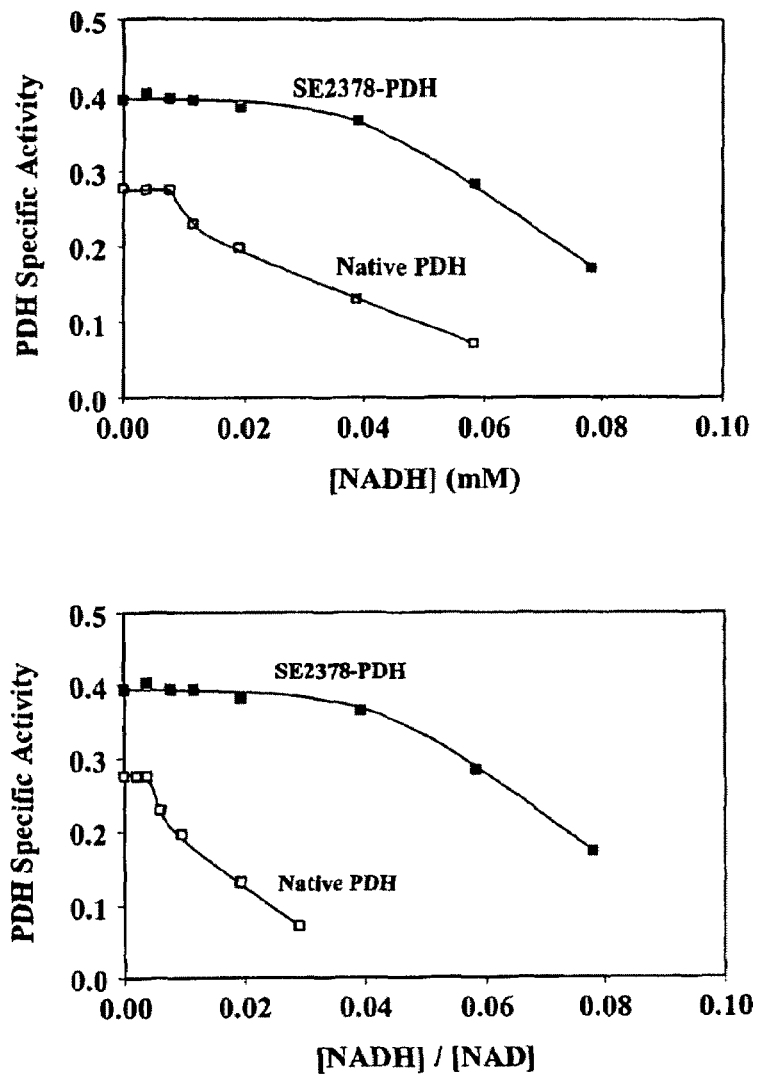
FIG. 10 is a graph showing inhibition of PDH activity by NADH. *E. coli* wild type, strain W3110 or the ethanologenic mutant, strain SE2378. In the top panel, NAD concentration was 2 mM for both strain W3110 and strain SE2378. In the bottom panel, NAD concentration was 2 mM NAD for the native enzyme from strain W3110 and 1 mM for the mutated form of the enzyme from strain SE2378.
Figure 11:
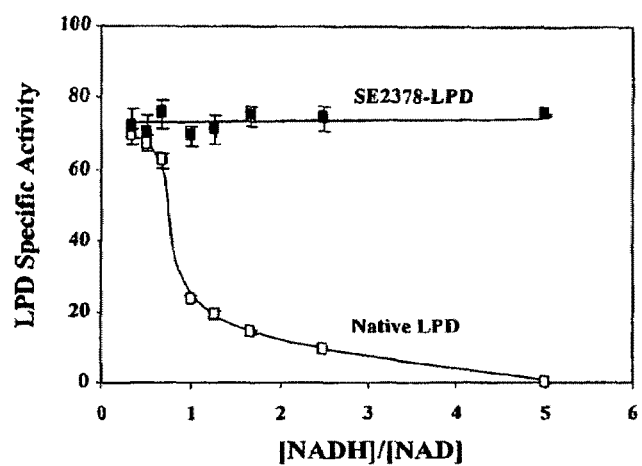
FIG. 11 is a graph showing inhibition of LPD by NADH. The ratio of NADH to NAD on the activity of the enzyme was determined for both the native and mutated form of LPD.

In this example, mutation in the lpd gene is shown to cause NADH insensitivity. More particularly, it was found that dihydrolipoamide dehydrogenase (LPD) activity that is NADH sensitive in the wild type (native) enzyme is changed to NADH-insensitive in the mutant, as shown in FIG. 10 and FIG. 11. Because LPD is a component of the pyruvate dehydrogenase complex (PDH) this NADH insensitivity of the LPD is carried through to the PDH from the ethanologenic mutant.

E. coli wild type, strain W3110, or the ethanologenic mutant, strain SE2378 were cultured in glucose-mineral salts medium to mid-exponential phase of growth. The cells were then harvested and an extract was prepared. Enzyme activity in the cell extract was determined with pyruvate and NAD as substrates, and varying concentrations of NADH as the inhibitor of enzyme activity. FIG. 10 shows inhibition of PDH activity by NADH. In the top panel, NAD concentration was 2 mM NAD for both wild type, strain W3110, and the ethanologenic mutant, strain SE2378. In the bottom panel, NAD concentration was 2 mM NAD for native enzyme from strain W3110, and 1 mM for the mutated form of the enzyme from strain SE2378.

The lpd gene from E. coli wild type, strain W3110, and the ethanologenic mutant, strain SE2378, was amplified by PCR and cloned into a protein expression vector, pET15b. The DNA sequence of the lpd gene in the selected plasmid was verified by sequencing the insert DNA. Expression of the lpd gene in the plasmid was induced and the protein was purified. Enzyme activity was determined in the reverse reaction in which the two substrates were lipoamide (3 mM) and NADH (0.1 mM) in 0.1 M K-phosphate buffer, pH 8.0 with 1.5 mM EDTA. FIG. 11 shows inhibition of LPD by NADH. Under these conditions, the native enzyme had no detectable activity, as shown in the graph in FIG. 11. NAD, the product of the reaction is a required activator of the enzyme activity and the activity increased with increasing NAD concentration. The ratio of NADH to NAD on the activity of the enzyme was determined for both the native and mutated from of the enzyme and the results are presented in FIG. 11.

PDH is produced by all aerobic organisms (from bacteria to man). This enzyme oxidatively decarboxylates pyruvate to acetyl-CoA, CO2 and NADH and the acetyl-CoA is then fed into the TCA cycle for further oxidation and subsequent energy production. In E. coli, PDH is produced under both aerobic and anaerobic conditions. However, under anaerobic conditions the enzyme is inactive due to inhibition of PDH by NADH. NADH is usually present at a higher concentration in the anaerobic cell, and thus prevents generation of NADH that cannot be oxidized by the cell that is lacking external electron acceptors. As a consequence the cell produces only 2 NADH per glucose, and the second set of reductant is released as hydrogen gas. Because one acetyl-CoA reduction to ethanol requires two NADH, the wild type cell cannot produce two ethanols per glucose.

In the ethanologenic mutant strains of the instant invention, PDH is less sensitive to NADH. This decreased sensitivity allows the enzyme to function even under anaerobic conditions with a higher NADH pool. Due to this biochemical change, the cell can produce four NADH molecules per glucose (2 from glycolysis and 2 from PDH reaction). All four NADHs are used to reduce two acetyl-CoA to ethanol, making the mutant a homoethanol producer. Biochemically and physiologically, the cell is a homoethanol producer due to the decrease in sensitivity of the PDH to NADH, and its ability to function even with a high NADH/NAD ratio.

Finally, in an additional experiment (data not shown), the mutation (E354K) in the LPD found in strain SE2378 was introduced into the LPD of *B. subtilis*, an aerobic organism, at the analogous location. The E356K mutation supported anaerobic growth of the mutant (MR1).

EXAMPLE 6

Comparison Alignment of Lpd Sequences from Other Organisms

In this example, comparison alignments of the amino acid sequences of the dihydrolipoamide dehydrogenase (LPD) enzymes from different organisms are compared and contrasted.

Pyruvate dehydrogenase (PDH) is present in all aerobic organisms from bacteria to humans. LPD is an essential component of the PDH enzyme complex, and it is present in both the PDH complex and 2-oxoglutarate dehydrogenase complex. In *E. coli*, the lpd is shared by these two enzyme complexes, and due to this requirement, the lpd gene is transcribed from an independent promoter, in addition to a promoter lying upstream of the pdhR gene.

Lpd homologs are found in all domains of life. Among bacterial strains, Lpd protein ranges from 458 to 581 amino acids, with an anhydrous molecular weight of 49000 to 62000 Da. Amino acid sequence identity of 20 Lpd homologs from bacteria from various phylogenetic groupings is shown in Table 7 below.

The amino acid sequence of dihydrolipoamide dehydrogenase from various organisms was compared to that of *E. coli* LPD protein using Blast server at NCBI or ClustalW at the European Biotechnology Institute. Percent identity of a specific sequence to that of the *E. coli* sequence was obtained from either of the two databases. The values in parenthesis represent the total similarity of the specific protein to that of the *E. coli* Lpd and include both the amino acid positions that are identical as well as the positions at which a conservative substitution occurred. For *Bacilus subtilis*, two dihydrolipoyl dehydrogenases, one from the PDH complex and the other from acetoin dehydrogenase, were included, for comparison.

Sequence identity varies from a low of 24% for *Methanosarcinia barkeri*, an archaeon, to 98% for *Salmonella typhimurium*. strain LT2, a Gram-negative bacterium. That *Salmonella typhimurium* LT2 LPD protein is most closely related to the *E. coli* LPD is consistent with the classification of the two bacteria as Gram-negative bacteria in the same family enterobacteriaceae. The *Escherichia coli* strain W3110 or MG1655 Lpd amino acid sequence was aligned with known Lpd sequences from *Acinetobacter* sp. ADP1, *Bacillus cereus* ATCC 10987, *Bacillus subtilis* strain 168, *Clostridium tetani* strain Massachusetts/E88, *Corynebacterium glutamicum* strain ATCC13032, *Geobacter metallireducens* GS-15, *Gluconobacter oxydans* 621H, *Lactobacillus casei* ATCC334, *Laclococcus lactis* subspecies *cremoris* SK11, *Lactobacillus plantarum* WCFS1, *Methanosarcinia barkeri* strain Fusaro, *Oenococcus oeni* MCW PSU-1, *Pseudomonas aeruginosa* PAO1 (ATCC15692), *Rhodobacter sphaeroides* 2.4.1, *Salmonella typhimurium* LT2, *Shewanella* sp ANA-3, *Streptococcus mutans* ATCC 700610, *Streptomyces coelicolor* M145, *Thermoanaerobacter ethanolicus*, *Vibrio fischeri* strain ATCC 700601. Homology alignment is shown in FIG. 9 [this figure will have to be renumbered]. When comparing total percent identity, the *E. coli* LPD appears to be most similar to other Gram-negative LPDs; however, when calculations of percent identity are made based on conservative substitution, Table 4 reflects a higher percent homology among the LPD proteins in the diverse organisms examined. For example, the amino acid sequence identity of *Bacillus subtillis* strain 168 LPD protein compared to that of *E. coli* LPD protein is 34%. However, taking in to account only conservative substitutions, the identity score increases to 57%. As can be seen from the alignment figure, several amino acids are highly conserved among the group of 20 LPD homologs from a very diverse group of organisms. Residues that are shared among the organisms are highlighted with an asterisk. Regions of interest are underlined. Among the sequences of the diverse organisms analyzed, the sequence identity is highest in the N-terminal region. Sequence identity can be seen between amino acids 40 and 55 (*E. coli* LPD numbering), which could represent a possible Flavin site. Another region of similarity is between amino acids 180 and 190. Throughout the sequence there are several positions at which the amino acid residues are conserved in all 20 LPDs from the diverse organisms analyzed. Notably, amino acid position 322 encodes histidine (H), and in three strains of the instant invention (SE2377, SE2383 and SE2382), there was a mutation in the histadine at position 322 to tyrosine (Y). Histidine at position 322 is conserved in all 20 LPDs from Gram-positive, Gram-negative bacteria to archaea. Other residues that are conserved across this diverse range include the proline at position 355 (18/20 LPDs) and the glutamate at position 356 (17/20 LPDs).

TABLE 7

Amino acid sequence identity of *E. coli* LPD protein to LPD homologs from other organisms.

| Organism | No. of amino acids | % Identity (Adjusted %)[a] |
|---|---|---|
| *Acinetobacter* sp. strain ADP1 | 468 | 35 (55) |
| *Bacillus cereus* strain ATCC 10987 | 470 | 44 (62) |
| *Bacillus subtilis* strain 168 E3 protein of Pyruvate DH | 470 | 47 (64) |
| *Bacillus subtilis* strain 168 E3 protein of Acetoin DH | 458 | 35 (57) |
| *Clostridium tetani* strain Massachusetts/E88 | 589 | 35 (58) |
| *Corynebacterium glutamicum* strain ATCC 13032 | 469 | 34 (53) |
| *Escherichia coli* strain W3110 or MG1655 | 474 | 100 |
| *Geobacter metallireducens* GS-15 | 476 | 35 (57) |

TABLE 7-continued

Amino acid sequence identity of *E. coli* LPD protein to LPD homologs from other organisms.

| Organism | No. of amino acids | % Identity (Adjusted %)[a] |
|---|---|---|
| *Gluconobacter oxydans* strain 621H | 468 | 32 (51) |
| *Lactobacillus casei* strain ATCC 334 | 471 | 30 (52) |
| *Lactococcus lactis* subsp. *cremoris* strain SK11 | 472 | 40 (59) |
| *Lactobacillus plantarum* strain WCFS1 (NCIMB 8826) | 470 | 39 (58) |
| *Methanosarcina barkeri* strain Fusaro | 476 | 24 (49) |
| *Oenococcus oeni* strain MCW PSU-1 | 473 | 39 (59) |
| *Pseudomonas aeruginosa* strain PAO1 ATCC 15692 | 467 | 37 (57) |
| *Rhodobacter sphaeroides* strain 2.4.1 | 462 | 40 (58) |
| *Salmonella typhimurium* LT2 ATCC 700720 | 474 | 98 (99) |
| *Shewanella* sp. strain ANA-3 | 475 | 85 (94) |
| *Streptococcus mutans* strain ATCC 700610 | 581 | 36 (56) |
| *Streptomyces coelicolor* strain M145 | 486 | 36 (55) |
| *Thermoanaerobacter ethanolicus* | 479 | 40 (58) |
| *Vibrio fischeri* strain ATCC 700601 | 475 | 86 (94) |

[a] Represents the amino acids that are identical and also conservative amino acid changes

REFERENCES

Bothast R J and Schlicher M A. 2005. Biotechnological processes for conversion of corn in to ethanol. Appl. Microbiol. Biotechnol. 67: 19-25.

Clark, D P. 1989. The fermentation pathways of *Escherichia coli*. FEMS Micrbiol. Rev. 5:223-234.

Datsenko and Wanner. 2000. One-step inactivation of chromosomal genes in *Escherichia coli* K-12 using PCR products. PNAS USA 97:6640-6645.

De Graef M R, Alexeeva S, Snoep J L, Teixeira de Mattos M J. 1999. The steady state internal redox state (NADH/NAD) reflects the external redox state and is correlated with catabolic adaptation in *Escherichia coli*. J. Bacteriol. 181:2351-2357.

Gonzalez R, Tao H, Shanmugam K T, York S W, Ingram L O. 2002. Global gene expression differences associated with changes in glycolytic flux and growth rate in *Escherichia coli* during fermentation of glucose and xylose. Biotechnol. Prog. 18:6-20.

Hasona A, Kim Y, Healy F G, Ingram L O and Shanmugam K T. 2004. Pyruvate formate lyase and acetate kinase are essential for anaerobic growth of *Escherichia coli* on xylose. J. Bacteriol. 186:7593-7600.

Ingram L O, Aldrich H C, Borges A C, Causey T B, Martinez A, Morales F, Saleh A, Underwood S A, Yomano L P, York S W, Zaldivar J, Zhou S. 1999. Enteric bacterial catalysts for fuel ethanol production. Biotechnol. Prog. 15:855-866.

Khesghi H S, Prince R C, Marland G. 2000. The potential of biomass fuels in the context of global climate change: focus on transportation fuels. Ann. Rev. Energy Env. 25:199-244.

Kuyper M, Toirkens M J, Diderich J A, Winkler A A, van Dijken J P, Pronk J T (2005) Evolutionary engineering of mixed-sugar utilization by a xylose-fermenting *Saccharomyces cerevisiae* strain. FEMS Yeast Res. 5:925-934.

Lee J H, Patel P, Sankar P, Shanmugam K T (1985) Isolation and characterization of mutant strains of *Escherichia coli* altered in H2 metabolism. J. Bacteriol. 162:344-352.

Maoly S and Nunn W D. 1981. Selection for loss of tetracycline resistance by *Escherichia coli*. J. Bacteriol. 145:1110-1112.

Maniatis T, et al. Molecular Cloning. A. Laboratory Manual. CSH Lab. N.Y. (1989)

Mat-Jan F, Alam K Y, Clark D P (1989) Mutants of *Escherichia coli* deficient in the fermentative lactate dehydrogenase. J. Bacteriol. 171:342-348.

Mohagheghi A, Dowe N, Schell D, Chou Y, Eddy C, Zhang M (2004) Performance of a newly developed integrant of *Zymomonas mobilis* for ethanol production on corn stover hydrolysate. Biotechnol. Lett. 26:321-325.

Patel, M A, Ou M S, Harbrucker H C, Aldrich M L, Buszko M L, Ingram L O, Shanmugam K T. 2006. Isolation and characterization of acid-tolerant, thermophilic bacteria for effective fermentation of biomass-derived sugars to lactic acid. Appl. Environ. Microbiol. 72: 3228-3235.

Quail M A, Hayden D J, Guest J R (1994) The pdhR-aceEF-lpd operon of *Escherichia coli* expresses the pyruvate dehydrogensae complex. Mol. Microbiol. 12:95-104.

Shanmugam K T, Valentine R C (1980) Nitrogen fixation (nif) mutants of *Klebsiella pneumoniae*. Methods in Enzymol. 69:47-52.

Smits H P, Hauf J, Muller S, Hobley T J, Zimmermann F K, Hahn-Hagerdal B, Nielsen J, Olsson L (2000) Simultaneous overexpression of enzymes of the lower part of glycolysis can enhance the fermentative capacity of *Saccharomyces cerevisiae*. Yeast 16:1325-1334.

Talarico L A, Ingram L O, Maupin-Furlow J A (2001) Production of the Gram-positive *Sarcina ventriculi* pyruvate decarboxylase in *Escherichia coli*. Microbiology 147:2425-2435.

Underwood S A, Zhou S, Causey T B, Yomano L P, Shanmugam K T, Ingram L O (2002) Genetic changes to optimize carbon partitioning between ethanol and biosynthesis in ethanologenic *Escherichia coli*. Appl. Environ. Microbiol. 68:6263-6272.

Underwood S A, Buszko M L, Shanmugam K T, Ingram L O. 2004. Lack of protective osmolytes limits final cell density and volumetric productivity of ethanologenic *Escherichia coli* KO11 during xylose fermentation. Appl. Environ. Microbiol. 70:2734-2740.

Wooley R, Ruth M, Glassner D, Sheehan J (1999) Process design and costing of bioethanol technology: a tool for determining the status and direction of research and development. Biotechnol. Prog. 15:794-803.

Wyman C E (2003) Potential synergies and challenges in refining cellulosic biomass to fuels, chemicals, and power. Biotechnol. Prog. 19:254-262.

Zaldivar J, Nielsen J, Olsson L (2001) Fuel ethanol production from lignocellulose: a challenge for metabolic engineering and process integration. Appl. Microbiol. Biotechnol. 56:17-34.

EQUIVALENTS

Those skilled in the art will recognize, or be able to ascertain using no more than routine experimentation, many equivalents to the specific embodiments of the invention described herein. Such equivalents are intended to be encompassed by this invention.

INCORPORATION BY REFERENCE

All publications, patent applications and patents identified herein are expressly incorporated herein by reference in their entirety.

```

What is claimed is:

1. A method for producing ethanol from an oligosaccharide source comprising contacting the oligosaccharide with an isolated non-recombinant bacterium comprising an lpd gene having a mutation, wherein the mutation is one that corresponds to the substitution of the His residue at amino acid position 322 relative to an *E. coli* LPD sequence and the mutation renders the non-recombinant bacterium capable of producing ethanol as the primary fermentation product under anaerobic conditions, thereby producing ethanol from an oligosaccharide source.

2. The method of claim 1, wherein the ethanol produced comprises greater than 50% of total non-gaseous fermentation products under anaerobic conditions.

3. The method of claim 1, wherein the bacterium, in the absence of the mutation, is non-ethanologenic.

4. The method of claim 3, wherein ethanol is the minor fermentation product and comprises less than 40% of total non gaseous fermentation products.

5. The method of claim 1, wherein the mutation provides a homoethanol fermentation pathway.

6. The method of claim 1, wherein one or more alternative pathways for fermentation in the bacterium are inactivated.

7. The method of claim 6, wherein the alternative pathways for fermentation include lactate production by lactate dehydrogenase (ldhA), acetate, ethanol, formate, $H_2$ and $CO_2$ starting with pyruvate formate-lyase (pfl) and succinate.

8. The method of claim 7, wherein the alternative pathways for fermentation are inactivated by mutation.

9. The method of claim 8, wherein the mutation is in the ldhA gene.

10. The method of claim 8, wherein the mutation is in the pfl gene.

11. The method of claim 9, wherein the mutation is in the ldhA or pflB genes.

12. The method of claim 10, wherein the mutation is in the ldhA or pflB genes.

13. The method of claim 1, wherein the oligosaccharide is selected from the group consisting of lignocellulose, hemicellulose, cellulose, pectin and any combination thereof.

14. The method of claim 1, wherein mutation in the lpd gene causes NADH insensitivity.

15. A method for producing ethanol from an oligosaccharide source comprising contacting the oligosaccharide with an isolated non-recombinant bacterium comprising an *E. coli* lpd gene having a mutation selected from the group consisting of H322Y and E354K, wherein the mutation renders the non-recombinant bacterium capable of producing ethanol as the primary fermentation product under anaerobic conditions, thereby producing ethanol from an oligosaccharide source.

16. The method of claim 15, wherein the ethanol produced comprises greater than 50% of total non-gaseous fermentation products under anaerobic conditions.

17. The method of claim 15, wherein the bacterium, in the absence of the mutation, is non-ethanologenic.

18. The method of claim 17, wherein ethanol is the minor fermentation product and comprises less than 40% of total non gaseous fermentation products.

19. The method of claim 15, wherein the mutation provides a homoethanol fermentation pathway.

20. The method of claim 15, wherein one or more alternative pathways for fermentation in the bacterium are inactivated.

21. The method of claim 20, wherein the alternative pathways for fermentation include lactate production by lactate dehydrogenase (ldhA), acetate, ethanol, formate, $H_2$ and $CO_2$ starting with pyruvate formate-lyase (pfl) and succinate.

22. The method of claim 21, wherein the alternative pathways for fermentation are inactivated by mutation.

23. The method of claim 22, wherein the mutation is in the ldhA gene.

24. The method of claim 22, wherein the mutation is in the pfl gene.

25. The method of claim 23, wherein the mutation is in the ldhA or pflB genes.

26. The method of claim 24, wherein the mutation is in the ldhA or pflB genes.

27. The method of claim 15, wherein the oligosaccharide is selected from the group consisting of lignocellulose, hemicellulose, cellulose, pectin and any combination thereof.

28. The method of claim 15, wherein mutation in the lpd gene causes NADH insensitivity.

* * * * *

                        SEQUENCE LISTING

<160> NUMBER OF SEQ ID NOS: 30

<210> SEQ ID NO 1
<211> LENGTH: 1458
<212> TYPE: DNA
<213> ORGANISM: Escherichia coli

<400> SEQUENCE: 1
atgaccgccg gagataaata tatagaggtc atgatgagta ctgaaatcaa aactcaggtc      60
gtggtacttg gggcaggccc cgcaggttac tccgctgcct tccgttgcgc tgatttaggt     120
ctggaaaccg taatcgtaga acgttacaac acccttggcg gtgtttgcct gaacgtcggc     180
tgtatccctt ctaaagcact gctgcacgta gcaaaagtta tcgaagaagc caaagcgctg     240
gctgaacacg gtatcgtctt cggcgaaccg aaaaccgata tcgacaagat tcgtacctgg     300
aaagagaaag tgatcaatca gctgaccggt ggtctggctg tatggcgaa aggccgcaaa      360 gtcaaagtgg tcaacggtct gggtaaattc accggggcta cacccctgga agttgaaggt     420
gagaacggca aaaccgtgat caacttcgac aacgcgatca ttgcagcggg ttctcgcccg     480
atccaactgc cgtttattcc gcatgaagat ccgcgtatct gggactccac tgacgcgctg     540
gaactgaaag aagtaccaga acgcctgctg gtaatgggtg gcggtatcat cggtctggaa     600
atgggcaccg tttaccacgc gctgggttca cagattgacg tggttgaaat gttcgaccag     660
gttatcccgg cagctgacaa agacatcgtt aaagtcttca ccaagcgtat cagcaagaaa     720
ttcaacctga tgctggaaac caaagttacc gccgttgaag cgaaagaaga cggcatttat     780
gtgacgatgg aaggcaaaaa agcacccgct gaaccgcagc gttacgacgc cgtgctggta     840
gcgattggtc gtgtgccgaa cggtaaaaac ctcgacgcag gcaaagcagg cgtggaagtt     900
gacgaccgtg gtttcatccg cgttgacaaa cagctgcgta ccaacgtacc gcacatcttt     960
gctatcggcg atatcgtcgg tcaaccgatg ctggcataca aaggtgttca cgaaggtcac    1020
gttgccgctg aagttatcgc cggtaagaaa cactacttcg atccgaaagt tatcccgtcc    1080
atcgcctata ccgaaccaga agttgcatgg gtgggtctga ctgagaaaga agcgaaagag    1140
aaaggcatca gctatgaaac cgccaccttc ccgtgggctg cttctggtcg tgctatcgct    1200
tccgactgcg cagacggtat gaccaagctg attttcgaca aagaatctca ccgtgtgatc    1260
ggtggtgcga ttgtcggtac taacggcggc gagctgctgg gtgaaatcgg cctggcaatc    1320
gaaatgggtt gtgatgctga agacatcgca ctgaccatcc acgcgcaccc gactctgcac    1380
gagtctgtgg gcctggcggc agaagtgttc gaaggtagca ttaccgacct gccgaacccg    1440
aaagcgaaga agaagtaa                                                   1458

<210> SEQ ID NO 2
<211> LENGTH: 474
<212> TYPE: PRT
<213> ORGANISM: Escherichia coli
```

<400> SEQUENCE: 2

```
Met Ser Thr Glu Ile Lys Thr Gln Val Val Leu Gly Ala Gly Pro
 1               5                  10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala Tyr Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415
```

```
Asn Gly Gly Glu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 3
<211> LENGTH: 1458
<212> TYPE: DNA
<213> ORGANISM: Escherichia coli

<400> SEQUENCE: 3
```

| | | |
|---|---|---|
| atgaccgccg agataaaata tatagaggtc atgatgagta ctgaaatcaa aactcaggtc | 60 |
| gtggtacttg gggcaggccc cgcaggttac tccgctgcct ccgttgcgc tgatttaggt | 120 |
| ctggaaaccg taatcgtaga cgttacaac accttggcg tgtttgcct gaacgtcggc | 180 |
| tgtatcccctt ctaaagcact gctgcacgta gcaaaagtta tcgaagaagc caaagcgctg | 240 |
| gctgaacacg gtatcgtctt cggcgaaccg aaaaccgata tcgacaagat tcgtacctgg | 300 |
| aaagagaaag tgatcaatca gctgaccggt ggtctggctg gtatggcgaa aggccgcaaa | 360 |
| gtcaaagtgg tcaacggtct gggtaaattc accggggcta caccctgga agttgaaggt | 420 |
| gagaacggca aaccgtgat caacttcgac aacgcgatca ttgcagcggg ttctcgcccg | 480 |
| atccaactgc cgtttattcc gcatgaagat ccgcgtatct gggactccac tgacgcgctg | 540 |
| gaactgaaag aagtaccaga acgcctgctg gtaatgggtg cggtatcat cggtctggaa | 600 |
| atgggcaccg tttaccacgc gctgggttca cagattgacg tggttgaaat gttcgaccag | 660 |
| gttatcccgg cagctgacaa agacatcgtt aaagtcttca ccaagcgtat cagcaagaaa | 720 |
| ttcaacctga tgctggaaac caagttacc gccgttgaag cgaaagaaga cggcattat | 780 |
| gtgacgatgg aagcaaaaa agcacccgct gaaccgcagc gttacgacgc cgtgctggta | 840 |
| gcgattggtc gtgtgccgaa cggtaaaaac ctcgacgcag gcaaagcagg cgtggaagtt | 900 |
| gacgaccgtg gtttcatccg cgttgacaaa cagctgcgta ccaacgtacc gcacatcttt | 960 |
| gctatcggcg atatcgtcgg tcaaccgatg ctggcacaca aggtgttca cgaaggtcac | 1020 |
| gttgccgctg aagttatcgc cggtaagaaa cactacttcg atccgaaagt tatcccgtcc | 1080 |
| atcgcctata ccaaaccaga agttgcatgg gtgggtctga ctgagaaaga agcgaaagag | 1140 |
| aaaggcatca gctatgaaac cgccaccttc ccgtgggctg cttctggtcg tgctatcgct | 1200 |
| tccgactgcg cagacggtat gaccaagctg attttcgaca agaatctca ccgtgtgatc | 1260 |
| ggtggtgcga ttgtcggtac taacggcggc gagctgctgg gtgaaatcgg cctggcaatc | 1320 |
| gaaatgggtt gtgatgctga agacatcgca ctgaccatcc acgcgcaccc gactctgcac | 1380 |
| gagtctgtgg gcctggcggc agaagtgttc gaaggtagca ttaccgacct gccgaacccg | 1440 |
| aaagcgaaga agaagtaa | 1458 |

```
<210> SEQ ID NO 4
<211> LENGTH: 474
<212> TYPE: PRT
<213> ORGANISM: Escherichia coli

<400> SEQUENCE: 4

Met Ser Thr Glu Ile Lys Thr Gln Val Val Val Leu Gly Ala Gly Pro
1               5                  10                  15
```

```
Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Lys Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
```

His Glu Ser Val Gly Leu Ala Ala Glu Val Phe Glu Gly Ser Ile Thr
    450                 455                 460
Asp Leu Pro Asn Pro Lys Ala Lys Lys Lys
465                 470

<210> SEQ ID NO 5
<211> LENGTH: 1458
<212> TYPE: DNA
<213> ORGANISM: Escherichia coli

<400> SEQUENCE: 5

```
atgaccgccg agataaaata tatagaggtc atgatgagta ctgaaatcaa aactcaggtc      60
gtggtacttg gggcaggccc cgcaggttac tccgctgcct ccgttgcgc tgatttaggt     120
ctggaaaccg taatcgtaga acgttacaac acccttggcg tgtttgcct gaacgtcggc     180
tgtatccctt ctaaagcact gctgcacgta gcaaaagtta tcgaagaagc caaagcgctg     240
gctgaacacg gtatcgtctt cggcgaaccg aaaaccgata tcgacaagat tcgtacctgg     300
aaagagaaag tgatcaatca gctgaccggt ggtctggctg gtatggcgaa aggccgcaaa     360
gtcaaagtgg tcaacggtct gggtaaattc accggggcta cacctctgga agttgaaggt     420
gagaacggca aaccgtgat caacttcgac aacgcgatca ttgcagcggg ttctcgcccg     480
atccaactgc cgtttattcc gcatgaagat ccgcgtatct gggactccac tgacgcgctg     540
gaactgaaag aagtaccaga acgcctgctg gtaatgggtg cggtatcat cggtctggaa     600
atgggcaccg tttaccacgc gctgggttca cagattgacg tggttgaaat gttcgaccag     660
gttatcccgg cagctgacaa agacatcgtt aaagtcttca ccaagcgtat cagcaagaaa     720
ttcaacctga tgctggaaac caagttacc gccgttgaag cgaaagaaga cggcatttat     780
gtgacgatgg aagcaaaaa agcacccgct gaaccgcagc gttacgacgc cgtgctggta     840
gcgattggtc gtgtgccgaa cggtaaaaac ctcgacgcag gcaaagcagg cgtggaagtt     900
gacgaccgtg gtttcatccg cgttgacaaa cagctgcgta ccaacgtacc gcacatcttt     960
gctatcggcg atatcgtcgg tcaaccgatg ctggcacaca aaggtgttca cgaaggtcac    1020
gttgccgctg aagttatcgc cggtaagaaa cactacttcg atccgaaagt tatcccgtcc    1080
atcgcctata ccgaaccaga agttgcatgg gtgggtctga ctgagaaaga agcgaaagag    1140
aaaggcatca gctatgaaac cgccaccttc ccgtgggctg cttctggtcg tgctatcgct    1200
tccgactgcg cagacggtat gaccaagctg atttcgaca agaatctca ccgtgtgatc    1260
ggtggtgcga ttgtcggtac taacggcggc gagctgctgg gtgaaatcgg cctggcaatc    1320
gaaatgggtt gtgatgctga agacatcgca ctgaccatcc acgcgcaccc gactctgcac    1380
gagtctgtgg gcctggcggc agaagtgttc gaaggtagca ttaccgacct gccgaacccg    1440
aaagcgaaga agaagtaa                                                 1458
```

<210> SEQ ID NO 6
<211> LENGTH: 474
<212> TYPE: PRT
<213> ORGANISM: Eschericia coli

<400> SEQUENCE: 6

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

-continued

Val Ile Val Glu Arg Tyr Asn Thr Leu Gly Gly Val Cys Leu Asn Val
                35                  40                  45

Gly Cys Ile Pro Ser Lys Ala Leu Leu His Val Ala Lys Val Ile Glu
 50                  55                  60

Glu Ala Lys Ala Leu Ala Glu His Gly Ile Val Phe Gly Glu Pro Lys
 65                  70                  75                  80

Thr Asp Ile Asp Lys Ile Arg Thr Trp Lys Glu Lys Val Ile Asn Gln
                 85                  90                  95

Leu Thr Gly Gly Leu Ala Gly Met Ala Lys Gly Arg Lys Val Lys Val
                100                 105                 110

Val Asn Gly Leu Gly Lys Phe Thr Gly Ala Asn Thr Leu Glu Val Glu
                115                 120                 125

Gly Glu Asn Gly Lys Thr Val Ile Asn Phe Asp Asn Ala Ile Ile Ala
130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
                180                 185                 190

Val Tyr His Ala Leu Gly Ser Gln Ile Asp Val Val Glu Met Phe Asp
                195                 200                 205

Gln Val Ile Pro Ala Ala Asp Lys Asp Ile Val Lys Val Phe Thr Lys
                210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
                260                 265                 270

Arg Val Pro Asn Gly Lys Asn Leu Asp Ala Gly Lys Ala Gly Val Glu
                275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
                340                 345                 350

Thr Glu Pro Glu Val Ala Trp Val Gly Leu Thr Glu Lys Glu Ala Lys
                355                 360                 365

Glu Lys Gly Ile Ser Tyr Glu Thr Ala Thr Phe Pro Trp Ala Ala Ser
                370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
                420                 425                 430

Cys Asp Ala Glu Asp Ile Ala Leu Thr Ile His Ala His Pro Thr Leu
                435                 440                 445

His Glu Ser Val Gly Leu Ala Ala Glu Val Phe Glu Gly Ser Ile Thr
450                 455                 460

Asp Leu Pro Asn Pro Lys Ala Lys Lys Lys
465                 470

<210> SEQ ID NO 7
<211> LENGTH: 254
<212> TYPE: PRT
<213> ORGANISM: Eschericia coli

<400> SEQUENCE: 7

Met Ala Tyr Ser Lys Ile Arg Gln Pro Lys Leu Ser Asp Val Ile Glu
1               5                   10                  15

Gln Gln Leu Glu Phe Leu Ile Leu Glu Gly Thr Leu Arg Pro Gly Glu
            20                  25                  30

Lys Leu Pro Pro Glu Arg Glu Leu Ala Lys Gln Phe Asp Val Ser Arg
        35                  40                  45

Pro Ser Leu Arg Glu Ala Ile Gln Arg Leu Glu Ala Lys Gly Leu Leu
    50                  55                  60

Leu Arg Arg Gln Gly Gly Gly Thr Phe Val Gln Ser Ser Leu Trp Gln
65              70                  75                  80

Ser Phe Ser Asp Pro Leu Val Glu Leu Ser Asp His Pro Glu Ser
            85                  90                  95

Gln Tyr Asp Leu Leu Glu Thr Arg His Ala Leu Glu Gly Ile Ala Ala
            100                 105                 110

Tyr Tyr Ala Ala Leu Arg Ser Thr Asp Glu Asp Lys Glu Arg Ile Arg
        115                 120                 125

Glu Leu His His Ala Ile Glu Leu Ala Gln Gln Ser Gly Asp Leu Asp
130                 135                 140

Ala Glu Ser Asn Ala Val Leu Gln Tyr Gln Ile Ala Val Thr Glu Ala
145                 150                 155                 160

Ala His Asn Val Val Leu Leu His Leu Leu Arg Cys Met Glu Pro Met
                165                 170                 175

Leu Ala Gln Asn Val Arg Gln Asn Phe Glu Leu Leu Tyr Ser Arg Arg
            180                 185                 190

Glu Met Leu Pro Leu Val Ser Ser His Arg Thr Arg Ile Phe Glu Ala
        195                 200                 205

Ile Met Ala Gly Lys Pro Glu Glu Ala Arg Glu Ala Ser His Arg His
    210                 215                 220

Leu Ala Phe Ile Glu Glu Ile Leu Leu Asp Arg Ser Arg Glu Glu Ser
225                 230                 235                 240

Arg Arg Glu Arg Ser Leu Arg Arg Leu Glu Gln Arg Lys Asn
                245                 250

<210> SEQ ID NO 8
<211> LENGTH: 255
<212> TYPE: PRT
<213> ORGANISM: Eschericia coli

<400> SEQUENCE: 8

Met Ala Tyr Ser Lys Ile Arg Gln Pro Lys Leu Pro Asp Val Ile Glu
1               5                   10                  15

Gln Gln Leu Glu Phe Leu Ile Leu Glu Gly Thr Leu Arg Pro Gly Glu
            20                  25                  30

Lys Leu Pro Pro Glu Arg Glu Leu Ala Lys Gln Phe Asp Val Ser Arg
        35                  40                  45

Pro Ser Leu Arg Glu Ala Ile Gln Arg Leu Glu Ala Lys Gly Leu Leu
    50                  55                  60

```
Leu Arg Arg Gln Gly Gly Gly Thr Phe Val Gln Ser Ser Leu Trp Gln
 65                  70                  75                  80

Ser Phe Ser Asp Pro Leu Val Glu Leu Leu Ser Asp His Pro Glu Ser
                 85                  90                  95

Gln Tyr Asp Leu Leu Glu Thr Arg His Ala Leu Glu Gly Ile Ala Ala
            100                 105                 110

Tyr Tyr Ala Ala Leu Leu Arg Ser Thr Asp Glu Asp Lys Glu Arg Ile
        115                 120                 125

Arg Glu Leu His His Ala Ile Glu Leu Ala Gln Gln Ser Gly Asp Leu
    130                 135                 140

Asp Ala Glu Ser Asn Ala Val Leu Gln Tyr Gln Ile Ala Val Thr Glu
145                 150                 155                 160

Ala Ala His Asn Val Val Leu Leu His Leu Leu Arg Cys Met Glu Pro
                165                 170                 175

Met Leu Ala Gln Asn Val Arg Gln Asn Phe Glu Leu Leu Tyr Ser Arg
            180                 185                 190

Arg Glu Met Leu Pro Leu Val Ser Ser His Arg Thr Arg Ile Phe Glu
        195                 200                 205

Ala Ile Met Ala Gly Lys Pro Glu Glu Ala Arg Glu Ala Ser His Arg
    210                 215                 220

His Leu Ala Phe Ile Glu Glu Ile Leu Leu Asp Arg Ser Arg Glu Glu
225                 230                 235                 240

Ser Arg Arg Glu Arg Ser Leu Arg Arg Leu Glu Gln Arg Lys Asn
                245                 250                 255

<210> SEQ ID NO 9
<211> LENGTH: 193
<212> TYPE: DNA
<213> ORGANISM: Eschericia coli

<400> SEQUENCE: 9
aacgaaagaa ttagtgattt ttctggtaaa aattatccag aagatgttgt aaatcaagcg      60
catataaaag cgcggcaact aaacgtagaa cctgtcttat tgagctttcc ggcgagagtt     120
caatgggaca ggttccagaa aactcaacgt tattagatag ataaggaata acccatgtca     180
gaacgtttcc caa                                                       193

<210> SEQ ID NO 10
<211> LENGTH: 193
<212> TYPE: DNA
<213> ORGANISM: Eschericia coli

<400> SEQUENCE: 10
aacgaaagaa ttagtgattt ttctggtaaa aattatccag aagatgttgt aaatcaagcg      60
catataaaag cgcggcaact aaacgtagaa cctgtcttat tgagctttcc ggcgaaagtt     120
caatgggaca ggttccagaa aactcaacgt tattagatag ataaggaata acccatgtca     180
gaacgtttcc caa                                                       193

<210> SEQ ID NO 11
<211> LENGTH: 589
<212> TYPE: PRT
<213> ORGANISM: Clostridium tetani

<400> SEQUENCE: 11

Met Asn Phe Lys Lys Thr Ile Ala Ile Leu Ile Ile Arg Ile Ala Met
  1               5                  10                  15

Val Phe Lys Ile Cys Lys Lys Arg Gly Val Tyr Met Ile Lys Glu Ile
```

-continued

```
                20                  25                  30
Lys Leu Glu Lys Leu Phe Pro Gly Ser Lys Glu Gly Lys Val Gly Lys
                35                  40                  45
Ile His Lys Ser Ile Gly Asp Gly Ile Lys Ser Gly Glu Val Leu Val
         50                  55                  60
Glu Val Glu Gly Lys Lys Gly Asn Ile Pro Ile Lys Ala Lys Glu Glu
 65                  70                  75                  80
Gly Lys Ile His Ser Ile Glu Ile Glu Glu Gly Thr Thr Val Lys Ile
                 85                  90                  95
Gly Asp Val Leu Leu Lys Ile Glu Ile Glu Glu Val Thr Leu Asp Glu
                100                 105                 110
Phe Val Ile Asp Lys Asp Glu Phe Ala Lys Lys Ser Glu Leu Lys Ser
            115                 120                 125
Leu Glu Cys Asp Val Ala Ile Leu Gly Ala Gly Pro Gly Gly Tyr Val
        130                 135                 140
Ala Ala Ile Gln Ala Ala Lys Leu Gly Ala Lys Val Val Ile Val Glu
145                 150                 155                 160
Lys Asp Lys Val Gly Gly Thr Cys Leu Asn Arg Gly Cys Ile Pro Thr
                165                 170                 175
Lys Ala Phe Val Arg Ser Ser Glu Val Tyr Ser Asn Val Lys Asn Ser
            180                 185                 190
Glu Lys Tyr Gly Ile Ser Leu Glu Asn Pro Ser Ile Asp Ile Lys Lys
        195                 200                 205
Val Val Ala Arg Lys Asp Asn Ile Val Asp Lys Leu Val Gly Gly Ile
    210                 215                 220
Gln Tyr Leu Ile Gln Lys His Asn Ile Glu Leu Ile Ser Gly Asn Gly
225                 230                 235                 240
Lys Leu Ile Asp Arg Asn Thr Ile Glu Thr Lys Asp Ala Leu Ile Lys
                245                 250                 255
Ala Lys Asn Ile Val Ile Ala Ser Gly Ser Lys Ala Ser Val Leu Pro
            260                 265                 270
Ile Lys Gly Ser Asn Leu Lys Gln Val Ile Thr Ser Glu Glu Ala Leu
        275                 280                 285
Asp Leu Lys Glu Val Pro Glu Lys Ile Ala Ile Ile Gly Gly Gly Val
    290                 295                 300
Ile Gly Met Glu Phe Ala Phe Ile Tyr Ala Asn Met Gly Val Glu Val
305                 310                 315                 320
Ser Val Ile Glu Tyr Phe Asp Asn Ile Leu Ser Met Leu Asp Glu Asp
                325                 330                 335
Val Ile Lys Glu Ile Thr Asp Ile Gly Lys Glu Lys Gly Ile Lys Phe
            340                 345                 350
Tyr Thr Ser Ser Lys Val Glu Glu Ile Leu Glu Asp Glu Asn Glu Gly
        355                 360                 365
Cys Ile Val Lys Phe Thr Asn Lys Gly Glu Glu Lys Phe Ile Phe Cys
    370                 375                 380
Asp Lys Val Leu Met Ser Val Gly Arg Gln Pro Tyr Met Glu Asn Met
385                 390                 395                 400
Gly Val Glu Glu Leu Gly Ile Glu Leu Asn Gln Asn Lys Arg Gly Ile
                405                 410                 415
Lys Val Asn Thr Lys Met Glu Thr Ser Val Ser Asn Ile Tyr Ala Ile
            420                 425                 430
Gly Asp Val Thr Asn Val Ile Gln Leu Ala His Val Ala Ser His Gln
        435                 440                 445
```

```
Gly Ile Val Ala Val Lys Asn Ile Met Gly Lys Asp Ile Gln Ile Asp
            450                 455                 460

Tyr Ser Ala Val Pro Ser Val Ile Phe Thr Glu Pro Glu Ile Ala Val
465                 470                 475                 480

Val Gly Val Cys Glu Lys Ile Ala Lys Glu Asn Asn Leu Asp Val Glu
            485                 490                 495

Val Gly Lys Phe Pro Phe Ser Ala Asn Gly Lys Ala Leu Thr Leu Gly
            500                 505                 510

Glu Asp Arg Gly Phe Ile Lys Val Ile Lys Glu Lys Ala Thr Gly Lys
            515                 520                 525

Val Val Gly Ala Ser Ile Ile Gly Ala His Ala Ser Asp Leu Ile Ala
            530                 535                 540

Glu Leu Thr Leu Ala Val Lys Asn Gly Leu Thr Ser Glu Gln Ile Ala
545                 550                 555                 560

Glu Thr Ile His Ala His Pro Thr Thr Ala Glu Val Val His Glu Ala
            565                 570                 575

Ser Leu Ala Val Glu Gly Gly Ala Leu His Phe Ala Glu
            580                 585

<210> SEQ ID NO 12
<211> LENGTH: 479
<212> TYPE: PRT
<213> ORGANISM: Thermoanaerobacter ethanolicus

<400> SEQUENCE: 12

Met Met Lys Glu Gly Phe Leu Arg Leu Ser Val Glu Ile Asn Lys Lys
1               5                   10                  15

Ile Asn Gln Ala Ser Ile His Ser Lys Arg Ile Lys Met Asp Tyr
            20                  25                  30

Asp Val Ile Val Leu Gly Gly Gly Pro Gly Gly Tyr Thr Ala Ala Ile
            35                  40                  45

Arg Leu Ser Glu Leu Gly Lys Lys Val Ala Val Val Glu Glu Tyr Ser
    50                  55                  60

Leu Gly Gly Thr Cys Leu Asn Arg Gly Cys Ile Pro Thr Lys Val Tyr
65                  70                  75                  80

Ser His Ala Ala Glu Leu Ile Asn Ala Ile Lys Asp Ala Lys Asp Phe
                85                  90                  95

Gly Ile Met Ala Gln Tyr Ala Val Asp Ile Ala Lys Leu Arg Gln Lys
            100                 105                 110

Lys Glu Arg Val Val Lys Arg Leu Val Gly Gly Val Gly Tyr Leu Met
            115                 120                 125

Asn Leu His His Ile Asp Val Ile Lys Gly Arg Gly Arg Phe Val Asp
            130                 135                 140

Glu Asn Thr Ile Glu Val Asp Lys Arg Tyr Thr Ala Glu Asn Phe Ile
145                 150                 155                 160

Ile Ala Thr Gly Ser Lys Val Phe Leu Pro Pro Ile Glu Gly Ile Asn
                165                 170                 175

Leu Glu Gly Val Ile Thr Ser Asp Lys Ala Leu Glu Leu Glu Arg Ile
            180                 185                 190

Pro Glu Lys Ile Val Ile Gly Ala Gly Ile Ile Gly Leu Glu Phe
            195                 200                 205

Ala Asn Ile Tyr Ser Ala Leu Gly Ser Lys Val Val Ile Ile Glu Met
            210                 215                 220

Leu Pro Gln Leu Leu Pro Met Leu Asp Arg Asp Ile Ala Asp Thr Met
225                 230                 235                 240
```

```
Glu Lys Ile Leu Arg His Lys Lys Phe Glu Leu His Leu Asn Ser Lys
                245                 250                 255

Val Glu Lys Ile Glu Glu Gly Leu Lys Val Val Tyr Thr Thr Glu Gly
            260                 265                 270

Asn Thr Gln Val Val Glu Cys Asp Thr Val Leu Val Ala Val Gly Arg
        275                 280                 285

Val Ala Asn Val Asn Gly Ile Glu Ala Leu Asn Leu Asp Met Asp Lys
    290                 295                 300

Lys Gly Ile Lys Val Asp Ser His Met Arg Thr Ser Ile Lys Asn Ile
305                 310                 315                 320

Tyr Ala Ile Gly Asp Val Thr Gly Gly Ile Gln Leu Ala His Val Ala
                325                 330                 335

Ser Tyr Gln Gly Ile Val Ala Ala His Asn Ile Ala Gly Glu Glu Lys
            340                 345                 350

Glu Ala Asp Leu Ser Ile Val Pro Asn Cys Leu Tyr Thr Asn Pro Glu
        355                 360                 365

Ile Ala Trp Ala Gly Leu Asn Glu Val Gln Ala Arg Glu Lys Phe Gly
    370                 375                 380

Asp Val Lys Ile Gly Thr Phe Pro Tyr Thr Ala Leu Gly Arg Ala Met
385                 390                 395                 400

Thr Met Gly Gln Asn Asp Gly Phe Val Lys Ile Ile Ala Glu Ala Lys
                405                 410                 415

Tyr Asn Arg Val Val Gly Met Glu Ile Ile Gly Ala Gly Ala Thr Glu
            420                 425                 430

Ile Ile His Glu Gly Val Leu Ala Ile Lys Glu Glu Phe Thr Leu Glu
        435                 440                 445

Glu Leu Ala Asp Ala Ile His Ala His Pro Thr Leu Ser Glu Ser Val
    450                 455                 460

Lys Glu Ala Ala Glu Asp Ala Leu Gly Met Pro Ile Asn Lys Gly
465                 470                 475

<210> SEQ ID NO 13
<211> LENGTH: 470
<212> TYPE: PRT
<213> ORGANISM: Bacillus cereus

<400> SEQUENCE: 13

Met Val Val Gly Asp Phe Pro Ile Glu Leu Asp Thr Val Val Val Gly
  1               5                  10                  15

Ala Gly Pro Gly Gly Tyr Val Ala Ala Ile Arg Ala Ala Gln Leu Gly
            20                  25                  30

Gln Lys Val Ala Ile Ile Glu Lys Ala Asn Leu Gly Gly Val Cys Leu
        35                  40                  45

Asn Val Gly Cys Ile Pro Ser Lys Ala Leu Ile Asn Ala Gly His Arg
    50                  55                  60

Tyr Glu Asn Ala Met His Ser Asp Asp Met Gly Ile Thr Ala Glu Asn
 65                  70                  75                  80

Val Lys Val Asp Phe Thr Lys Val Gln Glu Trp Lys Asn Gly Val Val
                85                  90                  95

Lys Lys Leu Thr Gly Gly Val Glu Gly Leu Leu Lys Gly Asn Lys Val
            100                 105                 110

Glu Ile Ile Arg Gly Glu Ala Tyr Phe Val Asp Ala Asn Thr Leu Arg
        115                 120                 125

Val Met Thr Glu Asp Ala Ala Gln Thr Tyr Thr Phe Lys Asn Ala Val
    130                 135                 140

```
Leu Ala Thr Gly Ser Thr Pro Ile Glu Ile Pro Gly Phe Lys Tyr Ser
145                 150                 155                 160

Lys Arg Val Ile Asn Ser Thr Gly Ala Leu Ser Leu Pro Glu Ile Pro
                165                 170                 175

Lys Lys Leu Val Val Ile Gly Gly Tyr Ile Gly Met Glu Leu Gly
            180                 185                 190

Thr Ala Tyr Ala Asn Phe Gly Thr Glu Val Thr Val Glu Ala Gly
        195                 200                 205

Asp Glu Ile Leu Ala Gly Phe Glu Lys Ala Met Ser Ser Val Val Lys
210                 215                 220

Arg Ala Leu Gln Lys Lys Gly Asn Val Thr Ile His Thr Lys Ala Met
225                 230                 235                 240

Ala Lys Gly Val Glu Glu Thr Glu Thr Gly Val Lys Val Ser Phe Glu
            245                 250                 255

Val Lys Gly Glu Ile Gln Thr Val Glu Ala Asp Tyr Val Leu Val Thr
            260                 265                 270

Val Gly Arg Arg Pro Asn Thr Gln Glu Ile Gly Leu Glu Gln Val Gly
            275                 280                 285

Val Lys Met Thr Asp Arg Gly Ile Ile Glu Ile Asp Glu Gln Cys Arg
290                 295                 300

Thr Asn Val Pro Asn Ile Tyr Ala Ile Gly Asp Ile Val Pro Gly Pro
305                 310                 315                 320

Pro Leu Ala His Lys Ala Ser Tyr Glu Gly Lys Val Ala Val Glu Ala
                325                 330                 335

Ile Ser Gly His Ala Ser Ala Ile Asp Tyr Ile Gly Ile Pro Ala Val
            340                 345                 350

Cys Phe Thr Asp Pro Glu Leu Ala Ser Val Gly Tyr Thr Lys Lys Gln
355                 360                 365

Ala Glu Glu Ala Gly Met Thr Val Thr Val Ser Lys Phe Pro Phe Ala
        370                 375                 380

Ala Asn Gly Arg Ala Leu Ser Leu Asn Ser Thr Asp Gly Phe Leu Gln
385                 390                 395                 400

Leu Val Thr Arg Lys Glu Asp Gly Leu Leu Val Gly Ala Gln Val Ala
                405                 410                 415

Gly Ala Gly Ala Ser Asp Ile Ile Ser Glu Ile Gly Leu Ala Ile Glu
            420                 425                 430

Ala Gly Met Thr Ala Glu Asp Ile Ala Gln Thr Ile His Ala His Pro
        435                 440                 445

Thr Leu Gly Glu Ile Thr Met Glu Ala Ala Glu Val Ala Leu Gly Met
450                 455                 460

Pro Ile His Ile Val Lys
465                 470

<210> SEQ ID NO 14
<211> LENGTH: 470
<212> TYPE: PRT
<213> ORGANISM: Lactobacillus plantarum

<400> SEQUENCE: 14

Met Val Val Gly Asp Phe Ala Glu Glu Arg Asp Thr Met Ile Ile Gly
1               5                   10                  15

Ala Gly Pro Gly Gly Tyr Val Ala Ala Ile Arg Ala Ala Glu Leu Gly
            20                  25                  30

Gln Lys Val Thr Val Val Glu Lys Glu Tyr Ile Gly Gly Val Cys Leu
        35                  40                  45
```

-continued

```
Asn Val Gly Cys Ile Pro Ser Lys Ala Leu Ile Ser Ala Gly His Arg
 50                  55                  60
Leu Gln Glu Ala Lys Asp Ser Lys Ile Phe Gly Ile Lys Asn Ile Gln
 65                  70                  75                  80
Asp Pro Val Leu Asp Phe Lys Val Thr Gln Asp Trp Lys Asp His Gln
                     85                  90                  95
Val Val Asp Arg Leu Thr Gly Gly Val Glu Met Leu Leu Lys Lys His
            100                 105                 110
Lys Val Glu Val Val Arg Gly Glu Ala Tyr Met His Asp Asn His Thr
        115                 120                 125
Leu Arg Val Met Asn Gly Asp His Thr Gly Gln Thr Tyr Lys Phe Lys
130                 135                 140
His Leu Ile Ile Ala Thr Gly Ser Arg Pro Val Glu Ile Pro Gly Phe
145                 150                 155                 160
Lys Phe Ser Gly Arg Val Val Asp Ser Thr Gly Gly Leu Asn Leu Pro
                    165                 170                 175
Glu Val Pro Lys Glu Leu Val Val Ile Gly Gly Gly Tyr Ile Gly Ser
                180                 185                 190
Glu Leu Ala Gly Ala Tyr Ala Asn Leu Gly Ala His Val Thr Ile Leu
            195                 200                 205
Glu Gly Thr Pro Gln Ile Leu Pro Asn Phe Glu Lys Asp Met Val Lys
        210                 215                 220
Leu Val Leu Asn Ser Phe Lys Lys Gly Val Asp Val Ile Thr Asn
225                 230                 235                 240
Ala Met Ala Lys Asn Ser Glu Gln Asp Ser Gly Val Thr Val Thr
                    245                 250                 255
Tyr Ala Val Asp Gly Lys Glu Thr Glu Ile His Ala Asp Tyr Val Met
                260                 265                 270
Val Thr Val Gly Arg Arg Pro Asn Thr Asp Asp Met Gly Leu Glu Tyr
            275                 280                 285
Thr Asp Val Lys Leu Thr Lys Arg Gly Leu Ile Glu Val Asp Glu Gln
        290                 295                 300
Gly Arg Thr Ala Ala Glu Asp Ile Phe Ala Ile Gly Asp Ile Val Ala
305                 310                 315                 320
Gly Ala Ala Leu Ala His Lys Ala Phe Ala Glu Ala Lys Val Ala Ala
                    325                 330                 335
Gly Ala Ile Ser Gly Lys Lys Thr Ala Asn Asp Tyr Val Ser Ile Pro
                340                 345                 350
Ala Val Cys Phe Thr Asp Pro Glu Leu Ala Thr Val Gly Met Thr Lys
            355                 360                 365
Ala Glu Ala Glu Glu Ala Gly Leu Gln Val Lys Thr Ser Lys Phe Pro
        370                 375                 380
Phe Ala Gly Asn Gly Arg Ala Ile Ser Leu Asn Ala Met Asp Gly Phe
385                 390                 395                 400
Phe Arg Leu Val Ser Thr Lys Asp Glu Gly Thr Ile Val Gly Ala Gln
                    405                 410                 415
Ile Ala Gly Pro Gly Ala Ser Asp Leu Ile Ser Glu Leu Ser Val Ala
                420                 425                 430
Val Asn Gly Gly Met Asn Val Glu Asp Leu Ala Leu Thr Ile His Pro
            435                 440                 445
His Pro Thr Leu Gly Glu Val Val Gln Glu Ala Ala Asp Glu Ala Met
        450                 455                 460
Gly Tyr Pro Thr His Ile
465                 470
```

<210> SEQ ID NO 15
<211> LENGTH: 472
<212> TYPE: PRT
<213> ORGANISM: Lactococcus lactis

<400> SEQUENCE: 15

Met Val Val Gly Ala Gln Ala Thr Glu Val Asp Leu Val Ile Ile Gly
1               5                   10                  15

Ser Gly Pro Gly Gly Tyr Val Ala Ala Ile Arg Ala Ala Glu Leu Gly
            20                  25                  30

Lys Lys Val Thr Ile Ile Glu Lys Asp Asn Val Gly Gly Val Cys Leu
        35                  40                  45

Asn Ile Gly Cys Ile Pro Ser Lys Ala Leu Ile Asn Ile Gly His His
    50                  55                  60

Tyr Gln Glu Ser Leu Glu Glu Lys Gly Glu Asn Pro Phe Gly Leu
65                  70                  75                  80

Ser Val Gly Asn Val Lys Leu Asn Trp Glu Ser Ala Gln Lys Trp Lys
                85                  90                  95

Gln Asp Lys Val Val Asn Gln Leu Thr Gly Gly Val Lys Met Leu Leu
            100                 105                 110

Lys Lys His Lys Val Asp Val Ile Gln Gly Thr Ala Glu Phe Ile Asp
        115                 120                 125

Asn Asn Thr Ile Asn Val Glu Gln Glu Asp Gly Phe Gln Leu Leu Gln
    130                 135                 140

Phe Asn Asp Val Ile Ile Ser Thr Gly Ser Arg Pro Ile Glu Ile Pro
145                 150                 155                 160

Ser Phe Pro Phe Gly Gly Arg Ile Ile Asp Ser Thr Gly Ala Leu Ser
                165                 170                 175

Leu Pro Glu Val Pro Lys His Leu Ile Ile Val Gly Gly Gly Val Ile
            180                 185                 190

Gly Ser Glu Leu Gly Gly Ala Tyr Arg Met Leu Gly Ser Lys Ile Thr
        195                 200                 205

Ile Val Glu Gly Leu Asp His Ile Leu Asn Gly Phe Asp Lys Glu Met
    210                 215                 220

Ser Asp Ile Ile Ala Asn Arg Val Lys Ser Ala Gly Ser Glu Ile Phe
225                 230                 235                 240

Thr Ser Ala Met Ala Lys Ser Ala Thr Gln Thr Asp Lys Asp Val Thr
                245                 250                 255

Leu Thr Phe Glu Val Asp Gly Lys Glu Gln Thr Val Thr Gly Asp Tyr
            260                 265                 270

Leu Leu Val Ser Val Gly Arg Arg Pro Asn Thr Asp Leu Ile Gly Leu
        275                 280                 285

Asn Asn Thr Asp Val Lys Leu Thr Asp Arg Gly Leu Ile Glu Val Asp
    290                 295                 300

Asp Ser Tyr Ala Thr Asn Val Pro His Ile Tyr Ala Ile Gly Asp Val
305                 310                 315                 320

Val Pro Gly Pro Met Leu Ala His Lys Ala Ser Phe Gln Ala Lys Val
                325                 330                 335

Ala Ala Ala Ala Ile Ala Gly Ala Glu Asp Asp Val Asp Leu His Val
            340                 345                 350

Ala Leu Pro Ala Val Ala Tyr Thr Thr Thr Glu Leu Ala Thr Val Gly
        355                 360                 365

Glu Thr Pro Glu Ser Val Lys Asp Arg Lys Asp Val Lys Ile Ser Lys
    370                 375                 380

```
Phe Pro Phe Ala Ala Asn Gly Arg Ala Ile Ser Met Asn Asp Thr Thr
385                 390                 395                 400

Gly Phe Leu Arg Leu Ile Thr Glu Thr Lys Glu Gly Ala Leu Ile Gly
            405                 410                 415

Ala Gln Ile Val Gly Pro Gly Ala Ser Asp Leu Ile Ser Gly Leu Ser
        420                 425                 430

Leu Ala Ile Glu Asn Gly Leu Thr Ser Lys Asp Ile Ser Leu Thr Ile
    435                 440                 445

Gln Pro His Pro Thr Leu Gly Glu Ala Ile Met Asp Thr Ala Glu Leu
450                 455                 460

Ala Asp Gly Leu Pro Ile His Val
465                 470

<210> SEQ ID NO 16
<211> LENGTH: 473
<212> TYPE: PRT
<213> ORGANISM: Oenococcus oeni

<400> SEQUENCE: 16

Met Ala Thr Gly Gly Val Val Gly Ala Gln Ala Thr Asp Ile Asp Thr
1               5                   10                  15

Val Val Ile Gly Ser Gly Pro Gly Gly Tyr Val Ala Ala Ile Arg Ala
            20                  25                  30

Ala Glu Leu Gly Gln Lys Val Thr Ile Ile Glu Ser Thr Phe Ile Gly
        35                  40                  45

Gly Val Cys Leu Asn Val Gly Cys Ile Pro Ser Lys Ala Leu Ile Asn
    50                  55                  60

Val Gly His His Tyr His Asp Ala Val Ser Glu Gln Pro Phe Gly Leu
65                  70                  75                  80

Lys Ser Ser Gly Thr Glu Leu Asp Trp Lys Thr Thr Gln Glu Trp Lys
                85                  90                  95

Gln Lys Lys Val Val Asn Gln Leu Thr Gly Gly Val Glu Met Leu Leu
            100                 105                 110

Lys Lys His Arg Val Asp Ile Ile His Gly Val Ala Ser Phe Val Asp
        115                 120                 125

Asn Lys Gln Ile Asn Val Lys Gly Asp Asp His Glu Leu Phe Gln
    130                 135                 140

Phe Asn Asn Cys Ile Leu Ala Thr Gly Ser Arg Pro Ile Glu Ile Pro
145                 150                 155                 160

Gly Phe Ala Phe Gly Lys Arg Ile Val Asp Ser Thr Ala Ala Leu Ser
                165                 170                 175

Leu Pro Glu Ile Pro Lys His Leu Ile Val Ile Gly Gly Gly Val Ile
            180                 185                 190

Gly Phe Glu Leu Gly Ser Val Tyr Gln Asn Leu Gly Ser Lys Val Thr
        195                 200                 205

Val Ile Glu Gly Leu Asp His Val Leu Ser Gly Phe Asp Lys Glu Met
    210                 215                 220

Ile Gln Pro Val Leu Asp Asp Phe Lys Ala Gln Gly Gly Glu Ile Phe
225                 230                 235                 240

Thr Ser Ala Lys Ala Lys Ser Ala Ser Gln Thr Glu Lys Asp Val Thr
                245                 250                 255

Val Thr Phe Glu Ala Asp Gly Lys Glu Gln Thr Val Asp Gly Asp Tyr
            260                 265                 270

Leu Leu Val Ser Val Gly Arg Arg Pro Asn Thr Asp Asn Ile Gly Leu
        275                 280                 285
```

Asn Asn Thr Asn Val Lys Leu Thr Asp Arg Gly Leu Val Glu Ile Asp
    290                 295                 300

Asp Thr Met Lys Thr Asn Val Ser His Ile Tyr Ala Ile Gly Asp Ile
305                 310                 315                 320

Thr Val Gly Pro Ala Leu Ala His Lys Ala Ser Phe Gln Gly Lys Ile
                325                 330                 335

Ala Ala Ala Ala Ile Ser Gly Asp Gln Asn Ala His Asp Leu His Tyr
            340                 345                 350

Ser Leu Pro Ala Val Ala Tyr Thr Asn Tyr Glu Leu Ala Thr Thr Gly
        355                 360                 365

Glu Thr Pro Glu Ser Val Lys Glu Lys Leu Asp Ala Lys Ala Tyr
    370                 375                 380

Lys Phe Pro Phe Ala Ala Asn Gly Arg Ala Leu Ser Ile Asn Glu Gly
385                 390                 395                 400

Lys Gly Phe Ile Arg Leu Ile Ser Asp Asn Gln Thr Lys Ala Leu Ile
                405                 410                 415

Gly Ser Gln Ile Val Gly Pro Gly Ala Ser Asp Leu Ile Ser Glu Leu
            420                 425                 430

Ser Leu Ala Ile Glu Asn Gly Leu Thr Thr Glu Asp Ile Ser Leu Thr
        435                 440                 445

Ile His Pro His Pro Thr Leu Gly Glu Ala Ile Met Asp Ala Ser Glu
    450                 455                 460

Leu Ala Asp Gly Leu Pro Ile His Ile
465                 470

<210> SEQ ID NO 17
<211> LENGTH: 474
<212> TYPE: PRT
<213> ORGANISM: Escherichia coli

<400> SEQUENCE: 17

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Glu Met Phe Asp
            195                 200                 205

Gln Val Ile Pro Ala Ala Asp Lys Asp Ile Val Lys Val Phe Thr Lys
210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
            245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
            325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
            355                 360                 365

Glu Lys Gly Ile Ser Tyr Glu Thr Ala Thr Phe Pro Trp Ala Ala Ser
            370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
            405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
            435                 440                 445

His Glu Ser Val Gly Leu Ala Ala Glu Val Phe Glu Gly Ser Ile Thr
            450                 455                 460

Asp Leu Pro Asn Pro Lys Ala Lys Lys Lys
465                 470

<210> SEQ ID NO 18
<211> LENGTH: 474
<212> TYPE: PRT
<213> ORGANISM: Salmonella typhimurium

<400> SEQUENCE: 18

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Thr Gln
            85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
130                 135                 140

Ala Gly Ser Arg Pro Ile Gln Leu Pro Phe Ile Pro His Glu Asp Pro
145                 150                 155                 160

Arg Val Trp Asp Ser Thr Asp Ala Leu Glu Leu Lys Glu Val Pro Lys
                165                 170                 175

Arg Met Leu Val Met Gly Gly Ile Ile Gly Leu Glu Met Gly Thr
            180                 185                 190

Val Tyr His Ala Leu Gly Ser Glu Ile Asp Val Val Glu Met Phe Asp
        195                 200                 205

Gln Val Ile Pro Ala Ala Asp Lys Asp Ile Val Lys Val Phe Thr Lys
210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Ser Met Glu Gly Lys Lys
                245                 250                 255

Ala Pro Ala Glu Ala Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
450                 455                 460

Asp Leu Pro Asn Pro Lys Ala Lys Lys Lys
465                 470

<210> SEQ ID NO 19
<211> LENGTH: 475
<212> TYPE: PRT
<213> ORGANISM: Vibrio fischeri

<400> SEQUENCE: 19

```
Met Ser Lys Gln Val Lys Ala Gln Val Val Leu Gly Ser Gly Pro
 1               5                  10                  15

Ala Gly Tyr Ser Ala Ala Phe Arg Cys Ala Asp Leu Gly Leu Glu Thr
             20                  25                  30

Val Leu Ile Glu Arg Tyr Ser Thr Leu Gly Gly Val Cys Leu Asn Val
         35                  40                  45

Gly Cys Ile Pro Ser Lys Ala Leu Leu His Val Ser Lys Val Ile Glu
     50                  55                  60

Glu Ala Lys Ala Met Ala Glu His Gly Val Val Phe Gly Glu Pro Gln
 65                  70                  75                  80

Thr Asp Ile Asn Lys Ile Arg Ile Trp Lys Asp Lys Val Val Thr Gln
                 85                  90                  95

Leu Thr Gly Gly Leu Gly Gly Met Ala Lys Met Arg Asn Val Thr Val
             100                 105                 110

Val Asn Gly Tyr Gly Lys Phe Thr Gly Pro Asn Thr Ile Glu Val Glu
         115                 120                 125

Gly Glu Glu Asn Thr Thr Val Thr Phe Asp Asn Ala Ile Ile Ala Ala
130                 135                 140

Gly Ser Arg Pro Ile Lys Leu Pro Phe Ile Pro His Glu Asp Pro Arg
145                 150                 155                 160

Ile Trp Asp Ser Thr Asp Ala Leu Glu Leu Lys Glu Val Pro Glu Lys
                 165                 170                 175

Leu Leu Ile Met Gly Gly Gly Ile Ile Gly Leu Glu Met Gly Thr Val
             180                 185                 190

Tyr His Ser Leu Gly Ser Lys Val Glu Val Val Glu Met Phe Asp Gln
         195                 200                 205

Val Ile Pro Ala Ala Asp Lys Asp Ile Val Lys Val Tyr Thr Lys Arg
210                 215                 220

Ile Lys Asp Lys Phe Lys Leu Met Leu Glu Thr Lys Val Thr Ala Val
225                 230                 235                 240

Glu Ala Lys Glu Asp Gly Ile Tyr Val Ser Met Glu Gly Lys Lys Ala
                 245                 250                 255

Pro Ala Glu Ala Glu Arg Tyr Asp Ala Val Leu Val Ala Ile Gly Arg
             260                 265                 270

Val Pro Asn Gly Lys Leu Ile Asp Ala Glu Lys Ala Gly Ile Glu Val
         275                 280                 285

Asp Glu Arg Gly Phe Ile Asn Val Asp Lys Gln Met Arg Thr Asn Val
290                 295                 300

Ala His Ile His Ala Ile Gly Asp Val Val Gly Gln Pro Met Leu Ala
305                 310                 315                 320

His Lys Gly Val His Glu Gly His Val Ala Ala Glu Val Ile Ser Gly
                 325                 330                 335

Lys Lys His Tyr Phe Asp Pro Lys Val Ile Pro Ser Ile Ala Tyr Thr
             340                 345                 350

Glu Pro Glu Val Ala Trp Val Gly Lys Thr Glu Lys Glu Ala Lys Glu
         355                 360                 365

Glu Gly Leu Asn Phe Glu Val Ala Thr Phe Pro Trp Ala Ala Ser Gly
370                 375                 380

Arg Ala Ile Ala Ser Asp Cys Ala Asp Gly Met Thr Lys Leu Ile Phe
385                 390                 395                 400

Asp Lys Glu Thr His Arg Val Ile Gly Gly Ala Ile Val Gly Thr Asn
                 405                 410                 415

Gly Gly Glu Leu Leu Gly Glu Ile Gly Leu Ala Ile Glu Met Gly Cys
```

```
                     420                 425                 430
Asp Ala Glu Asp Ile Ala Leu Thr Ile His Ala His Pro Thr Leu His
                435                 440                 445

Glu Ser Val Gly Leu Ala Ala Glu Val Phe Glu Gly Ser Ile Thr Asp
            450                 455                 460

Leu Pro Asn Lys Lys Ala Val Lys Lys Lys
465                 470                 475

<210> SEQ ID NO 20
<211> LENGTH: 475
<212> TYPE: PRT
<213> ORGANISM: Shewanella sp.

<400> SEQUENCE: 20

Met Ser Asn Glu Ile Lys Thr Gln Val Val Leu Gly Ala Gly Pro
  1               5                  10                  15

Ala Gly Tyr Ser Ala Ala Phe Arg Ala Ala Asp Leu Gly Leu Glu Thr
                 20                  25                  30

Val Ile Val Glu Arg Phe Ser Thr Leu Gly Gly Val Cys Leu Asn Val
             35                  40                  45

Gly Cys Ile Pro Ser Lys Ala Leu Leu His Val Ala Lys Val Ile Glu
         50                  55                  60

Glu Ala Lys Ala Val Ala Ala His Gly Val Val Phe Gly Glu Pro Thr
 65                  70                  75                  80

Ile Asp Leu Asp Lys Leu Arg Ser Phe Lys Gln Lys Val Ile Ser Gln
                 85                  90                  95

Leu Thr Gly Gly Leu Gly Gly Met Ser Lys Met Arg Lys Val Asn Val
            100                 105                 110

Val Asn Gly Phe Gly Lys Phe Thr Gly Pro Asn Ser Leu Glu Val Thr
        115                 120                 125

Ala Glu Asp Gly Thr Val Thr Val Val Lys Phe Asp Gln Ala Ile Ile
    130                 135                 140

Ala Ala Gly Ser Arg Pro Ile Lys Leu Pro Phe Ile Pro His Glu Asp
145                 150                 155                 160

Pro Arg Ile Trp Asp Ser Thr Asp Ala Leu Glu Leu Lys Glu Val Pro
                165                 170                 175

Gly Lys Leu Leu Val Met Gly Gly Gly Ile Ile Gly Leu Glu Met Gly
            180                 185                 190

Thr Val Tyr Ser Ser Leu Gly Ser Glu Ile Asp Val Val Glu Met Phe
        195                 200                 205

Asp Gln Val Ile Pro Ala Ala Asp Lys Asp Val Val Arg Val Phe Thr
    210                 215                 220

Lys Gln Ile Lys Lys Phe Asn Leu Ile Leu Glu Thr Lys Val Thr
225                 230                 235                 240

Ala Val Glu Ala Arg Glu Asp Gly Ile Tyr Val Ser Met Glu Gly Lys
                245                 250                 255

Ser Ala Pro Thr Glu Pro Val Arg Tyr Asp Ala Val Leu Val Ala Ile
            260                 265                 270

Gly Arg Thr Pro Asn Gly Lys Leu Ile Asp Ala Glu Lys Ala Gly Val
        275                 280                 285

Lys Ile Asp Glu Arg Gly Phe Ile Asn Val Asp Lys Gln Leu Arg Thr
    290                 295                 300

Asn Val Pro His Ile Tyr Ala Ile Gly Asp Ile Val Gly Gln Pro Met
305                 310                 315                 320

Leu Ala His Lys Gly Val His Glu Gly His Val Ala Ala Glu Val Ile
```

```
                    325                 330                 335
Ala Gly Met Lys His Tyr Phe Asp Pro Lys Val Ile Pro Ser Ile Ala
            340                 345                 350

Tyr Thr Asp Pro Glu Val Ala Trp Val Gly Leu Thr Glu Lys Glu Ala
            355                 360                 365

Lys Glu Gln Gly Ile Ala Tyr Glu Thr Ala Thr Phe Pro Trp Ala Ala
            370                 375                 380

Ser Gly Arg Ala Ile Ala Ser Asp Cys Ser Glu Gly Met Thr Lys Leu
385                 390                 395                 400

Ile Phe Asp Lys Asp Thr His Arg Val Ile Gly Gly Ala Ile Val Gly
                405                 410                 415

Val Asn Gly Gly Glu Leu Leu Gly Glu Ile Gly Leu Ala Ile Glu Met
            420                 425                 430

Gly Cys Asp Ala Glu Asp Leu Ala Leu Thr Ile His Ala His Pro Thr
            435                 440                 445

Leu His Glu Ser Val Gly Leu Ala Ala Glu Ile Tyr Glu Gly Ser Ile
            450                 455                 460

Thr Asp Leu Pro Asn Pro Lys Ala Lys Lys Lys
465                 470                 475

<210> SEQ ID NO 21
<211> LENGTH: 467
<212> TYPE: PRT
<213> ORGANISM: Pseudomonas aeruginosa

<400> SEQUENCE: 21

Met Met Glu Ser Tyr Asp Val Ile Val Ile Gly Ala Gly Pro Gly Gly
  1               5                  10                  15

Tyr Asn Ala Ala Ile Arg Ala Gly Gln Leu Gly Leu Lys Val Ala Cys
                 20                  25                  30

Val Glu Gly Arg Glu Thr Leu Gly Gly Thr Cys Leu Asn Val Gly Cys
             35                  40                  45

Met Pro Ser Lys Ala Leu Leu His Ala Ser Glu Leu Tyr Ala Ala Ala
         50                  55                  60

Ser Gly Gly Glu Phe Ala Arg Leu Gly Ile Arg Val Ser Pro Glu Leu
 65                  70                  75                  80

Asp Leu Ala Gln Met Met Lys Gln Lys Asp Glu Ser Val Ala Ala Leu
                 85                  90                  95

Thr Arg Gly Val Glu Phe Leu Phe Arg Lys His Lys Val Gln Trp Ile
            100                 105                 110

Lys Gly Trp Ala Arg Leu Gln Gly Glu Gly Arg Val Gly Val Ala Leu
        115                 120                 125

Ala Asp Gly Gly His Ala Gln Leu Glu Ala Arg Asp Ile Val Ile Ala
    130                 135                 140

Thr Gly Ser Glu Pro Ala Pro Leu Pro Gly Val Pro Val Asp Asn Gln
145                 150                 155                 160

Arg Ile Leu Asp Ser Thr Gly Ala Leu Glu Leu Val Glu Val Pro Arg
                165                 170                 175

His Leu Val Val Ile Gly Ala Gly Val Ile Gly Leu Glu Leu Gly Ser
            180                 185                 190

Val Trp Arg Arg Leu Gly Ala Gln Val Thr Val Leu Glu Tyr Leu Glu
        195                 200                 205

Arg Ile Cys Pro Gly Leu Asp Gly Glu Thr Ala Arg Thr Leu Gln Arg
    210                 215                 220

Ala Leu Thr Arg Gln Gly Met Arg Phe Arg Leu Gly Thr Arg Val Val
```

```
                 225                 230                 235                 240

Ala Ala Arg Ser Gly Glu Gln Gly Val Glu Leu Asp Leu Gln Pro Ala
                245                 250                 255

Ala Gly Gly Ala Thr Glu Ser Leu Gln Ala Asp Tyr Val Leu Val Ala
            260                 265                 270

Ile Gly Arg Arg Pro Tyr Thr Glu Gly Leu Gly Leu Glu Thr Val Gly
        275                 280                 285

Leu Ala Ser Asp Arg Arg Gly Met Leu Glu Asn Gln Gly Gln Arg Ser
    290                 295                 300

Ala Ala Pro Gly Val Trp Val Ile Gly Asp Val Thr Ser Gly Pro Met
305                 310                 315                 320

Leu Ala His Lys Ala Glu Glu Ala Ile Val Cys Ile Glu Arg Ile
                325                 330                 335

Ala Gly His Ala Ala Glu Met Asn Ala Glu Val Ile Pro Ser Val Ile
                340                 345                 350

Tyr Thr Gln Pro Glu Val Ala Ser Val Gly Leu Gly Glu Glu Gln Leu
            355                 360                 365

Gln Ala Ala Arg Arg Glu Tyr Lys Val Gly Arg Phe Pro Phe Ser Ala
        370                 375                 380

Asn Ser Arg Ala Lys Ile Asn His Glu Ser Glu Gly Phe Ile Lys Ile
385                 390                 395                 400

Leu Ser Asp Ala Arg Ser Asp Gln Val Leu Gly Val His Met Ile Gly
                405                 410                 415

Pro Gly Val Ser Glu Met Ile Gly Glu Ala Cys Val Ala Met Glu Phe
                420                 425                 430

Ser Ala Ser Ala Glu Asp Leu Ala Leu Thr Cys His Pro His Pro Thr
            435                 440                 445

Arg Ser Glu Ala Leu Arg Gln Ala Ala Met Asp Val His Gly Arg Ala
        450                 455                 460

Met Gln Asn
465

<210> SEQ ID NO 22
<211> LENGTH: 462
<212> TYPE: PRT
<213> ORGANISM: Rhodobacter sphaeroides

<400> SEQUENCE: 22

Met Ala Thr Phe Asp Val Ile Ile Gly Ala Gly Pro Gly Gly Tyr
  1               5                  10                  15

Val Ser Ala Ile Arg Cys Ala Gln Leu Gly Leu Lys Thr Ala Val Val
                 20                  25                  30

Glu Gly Arg Glu Ala Leu Gly Gly Thr Cys Leu Asn Val Gly Cys Ile
             35                  40                  45

Pro Ser Lys Ala Leu Leu His Ala Thr His Asn Leu His Glu Val His
         50                  55                  60

Glu Asn Phe Glu Lys Met Gly Leu Met Gly Ala His Pro Thr Val Asp
 65                  70                  75                  80

Trp Ser Lys Met Gln Gly Tyr Lys Gln Glu Val Val Asp Gly Asn Thr
                 85                  90                  95

Lys Gly Ile Glu Phe Leu Phe Lys Lys Asn Lys Ile Thr Trp Leu Lys
            100                 105                 110

Gly Trp Gly Ser Ile Pro Glu Pro Gly Lys Val Lys Val Gly Glu Glu
        115                 120                 125

Ile His Glu Ala Lys Ser Ile Val Ile Ala Thr Gly Ser Glu Pro Ala
```

```
                130             135             140
Ser Leu Pro Gly Val Glu Ala Asp Glu Ser Val Ile Val Thr Ser Thr
145                 150                 155                 160

Gly Ala Leu Ser Leu Gly Arg Ile Pro Glu Thr Met Val Val Ile Gly
                165                 170                 175

Ala Gly Val Ile Gly Leu Glu Leu Gly Ser Val Tyr Ala Arg Leu Gly
            180                 185                 190

Thr Lys Val Thr Val Val Glu Tyr Met Glu Ala Ile Leu Pro Gly Met
        195                 200                 205

Asp Ala Glu Val Val Lys Thr Thr Gln Arg Ile Leu Ala Lys Gln Gly
210                 215                 220

Leu Ser Phe Val Leu Gly Ala Val Lys Gly Ala Thr Val Ser Asp
225                 230                 235                 240

Gly Lys Ala Thr Val Thr Trp Ala Ala Lys Asp Gly Lys Glu Thr
                245                 250                 255

Ser Leu Thr Val Asp Thr Val Leu Val Ala Thr Gly Arg Lys Pro Phe
                260                 265                 270

Thr Glu Gly Leu Gly Leu Glu Ala Leu Gly Val Glu Met Leu Pro Arg
            275                 280                 285

Gly Val Val Lys Ile Asp Asp His Phe Arg Thr Ser Val Pro Gly Ile
290                 295                 300

Tyr Ala Ile Gly Asp Cys Val Pro Gly Met Met Leu Ala His Lys Ala
305                 310                 315                 320

Glu Asp Glu Gly Val Ala Leu Ala Glu Ile Leu Ala Gly Lys His Gly
                325                 330                 335

His Val Asn Tyr Gly Val Ile Pro Gly Val Ile Tyr Thr Thr Pro Glu
            340                 345                 350

Val Ala Ser Val Gly Arg Thr Glu Glu Ser Leu Lys Glu Glu Gly Arg
        355                 360                 365

Ala Tyr Lys Val Gly Lys Phe Pro Phe Met Gly Asn Ala Arg Ala Lys
    370                 375                 380

Ala Val Phe Gln Ala Glu Gly Phe Val Lys Met Ile Ala Asp Lys Glu
385                 390                 395                 400

Thr Asp Arg Ile Leu Gly Cys His Ile Ile Gly Pro Ala Ala Gly Asp
                405                 410                 415

Leu Ile His Glu Val Cys Val Ala Met Glu Phe Gly Ala Ser Ala Gln
            420                 425                 430

Asp Leu Ala Met Thr Cys His Ala His Pro Thr Trp Ser Glu Ala Val
        435                 440                 445

Arg Glu Ala Ala Leu Ala Cys Gly Asp Gly Ala Ile His Ala
    450                 455                 460

<210> SEQ ID NO 23
<211> LENGTH: 476
<212> TYPE: PRT
<213> ORGANISM: Geobacter metallireducens

<400> SEQUENCE: 23

Val Glu Lys Arg Ser Ala Leu Gly Gly Val Cys Leu Asn Glu Gly Cys
1               5                   10                  15

Ile Pro Ser Lys Ala Leu Leu Asp Ser Ser Glu Leu Phe Ala Leu Ala
            20                  25                  30

Arg Asp Arg Phe Ala Gly His Gly Ile Ala Ile Asp Pro Pro Arg Leu
        35                  40                  45

Asp Leu Ala Arg Met Met Ala Arg Lys Asp Asp Val Val Lys Lys Leu
```

```
            50                  55                  60
Thr Asp Gly Val Ala Phe Leu Phe Lys Asn Lys Ile Ala Arg Val
 65                  70                  75                  80

Gln Gly Thr Ala Arg Leu Thr Gly Glu Arg Asp Gly Ala His Gly Val
                 85                  90                  95

Asp Val Glu Gly Gly Asp Gln Gly Pro Gly Thr Gly Asp Arg Glu Lys
                100                 105                 110

Gln Thr Leu Arg Gly Lys Arg Val Leu Leu Ala Thr Gly Ser Glu Ala
            115                 120                 125

Ala Val Ile Pro Phe Met Pro Phe Asp Gly Glu Leu Val Val Ser Ala
130                 135                 140

Arg Glu Ala Leu Ser Phe Asp Arg Val Pro Glu His Leu Leu Val Val
145                 150                 155                 160

Gly Ala Gly Tyr Val Gly Leu Glu Leu Gly Ser Val Trp Arg Arg Leu
                165                 170                 175

Gly Ser Gln Val Thr Val Val Glu Met Leu Pro Lys Met Leu Pro Asn
            180                 185                 190

Thr Asp Gly Gln Val Ala Asp Thr Leu Met Gly Ser Leu Lys Lys Gln
            195                 200                 205

Gly Ile Val Phe Arg Met Glu Thr Lys Val Thr Gly Phe Ala Lys Arg
210                 215                 220

Asp Gly Lys Ala Ala Val Thr Val Glu Ala Gly Gly Ala Thr Glu Glu
225                 230                 235                 240

Ile Val Cys Asp Arg Val Leu Val Ala Ala Gly Arg Arg Pro Leu Thr
                245                 250                 255

Ala Gly Leu Gly Leu Glu Glu Leu Gly Val Arg Leu Glu Ala Gly Arg
            260                 265                 270

Ile Ala Val Asp Asp Asn Tyr Gln Thr Ser Leu Arg Gly Ile Tyr Ala
            275                 280                 285

Ile Gly Asp Leu Ile His Gly Pro Met Leu Ala His Lys Ala Met Ala
            290                 295                 300

Glu Gly Glu Val Phe Ala Glu Arg Leu Thr Gly Gln Ala Ser Val Val
305                 310                 315                 320

Asp Tyr Ala Tyr Ile Pro Gly Ile Val Tyr Thr Trp Pro Glu Ala Ala
                325                 330                 335

Gly Val Gly Arg Thr Glu Glu Leu Lys Thr Glu Gly Val Glu Tyr
                340                 345                 350

Arg Val Gly Lys Phe Pro Phe Met Ala Asn Gly Arg Ala Lys Cys Met
                355                 360                 365

Asp Glu Thr Glu Gly Phe Val Lys Ile Leu Ala Thr Pro Asp Thr Gly
            370                 375                 380

Arg Val Leu Gly Ile His Val Ile Gly Pro Arg Ala Ser Asp Val Ile
385                 390                 395                 400

Ala Glu Ala Val Thr Val Met Thr Tyr Gly Gly Ser Ala Ala Asp Ile
                405                 410                 415

Ala Met Thr Phe His Ala His Pro Thr Leu Ala Glu Ala Met Lys Glu
                420                 425                 430

Ala Ala Leu Asp Val Glu Lys Arg Ala Ile His Ala Thr Arg Arg Phe
            435                 440                 445

Pro Trp Glu Lys Ile Ser Gln Pro Arg Ser Ser Lys Arg Thr Ser Arg
            450                 455                 460

Arg Ala Ser Leu Ser Arg Ala Pro Arg Ser Pro Arg
465                 470                 475
```

<210> SEQ ID NO 24
<211> LENGTH: 468
<212> TYPE: PRT
<213> ORGANISM: Acinetobacter sp.

<400> SEQUENCE: 24

Met Ser Met Ser Asp Thr Gln Phe Asp Leu Val Val Ile Gly Ala Gly
1               5                   10                  15

Pro Gly Gly Tyr Val Ala Ala Ile Arg Ala Ala Gln Leu Gly Leu Lys
            20                  25                  30

Thr Ala Ile Val Glu Ala Thr His Leu Gly Gly Ile Cys Leu Asn Trp
        35                  40                  45

Gly Cys Ile Pro Thr Lys Ala Leu Leu Ala Gly Ala Glu Leu Ala His
    50                  55                  60

Gln Phe Lys His Ala Ser Gln Phe Gly Phe Glu Leu Gly Asp Ile Asn
65                  70                  75                  80

Phe Asp Leu Ser Lys Leu Val Gln His Ser Arg Gln Val Ser Ala Gln
                85                  90                  95

Leu Val Gln Gly Ile Glu His Leu Leu Arg Lys Asn Gln Val Ser Val
            100                 105                 110

Phe Tyr Ala Lys Ala Arg Phe Ile Ala Lys Glu Arg Leu Glu Leu Val
        115                 120                 125

Asp Ala Gln Gln Gln Lys Gln Met Ile Arg Ala Pro His Ile Ile Val
130                 135                 140

Ala Thr Gly Ala His Ala Ala Ser Leu Pro Gln Ile Pro Val Asp Gly
145                 150                 155                 160

Asp Tyr Val Trp Ser Tyr Lys Glu Ala Lys Gln Pro Lys Gln Leu Pro
                165                 170                 175

Lys Ser Leu Leu Val Ile Gly Ser Gly Ala Ile Gly Ser Glu Phe Ala
            180                 185                 190

Ser Leu Tyr Gln Asp Leu Gly Ser Gln Val Thr Leu Leu Asp Leu Ala
        195                 200                 205

Arg Gln Ile Leu Pro Thr Glu Asp His Glu Val Ala Gln Tyr Val Arg
210                 215                 220

Lys Gln Phe Glu Gln Lys Gly Met Arg Ile Leu Thr Glu Ser Thr Val
225                 230                 235                 240

Gln His Leu Glu Val Cys Glu Gly Lys Val His Cys Glu Ile His Asp
                245                 250                 255

Pro Ser Gly Val Gln Ser Leu Ser Phe Asp His Val Leu Ser Ala Val
            260                 265                 270

Gly Val Lys Pro Asn Thr Gln Asn Leu Gly Leu Glu Gln Leu Gly Val
        275                 280                 285

Ala Leu Thr Asn Gly Phe Ile Gln Thr Asp Glu Trp Cys Arg Thr Asn
290                 295                 300

Val Val Gly Ile Tyr Ala Ile Gly Asp Val Ala Gly Ala Pro Cys Leu
305                 310                 315                 320

Ala His Lys Ala Ser His Glu Ala Ile Leu Cys Val Glu Lys Ile Ala
                325                 330                 335

Gly Ile Ala Asp Val His Pro Leu Asn Arg Leu Gln Ile Pro Gly Cys
            340                 345                 350

Ile Phe Thr His Pro Gln Val Ala Ser Ile Gly Leu Thr Glu Gln Gln
        355                 360                 365

Ala Lys Ala Glu Gly Lys Gln Ile His Ile Gly Lys Phe Pro Met Ser
370                 375                 380

```
Ala Asn Gly Lys Ala Ile Ala Leu Gly Gln Thr Ala Gly Phe Val Lys
385                 390                 395                 400

Thr Ile Val Asp Val Glu Ser Gly Glu Leu Gly Ala His Met Val
            405                 410                 415

Gly His Glu Val Thr Glu Gln Ile Gln Gly Tyr Ala Ile Ala Gln Ala
            420                 425                 430

Leu Glu Ala Thr Asp Glu His Leu Ala Gln Val Ile Phe Pro His Pro
            435                 440                 445

Thr Leu Ser Glu Ala Met His Glu Ser Ile Leu Ala Ser Met Gln Arg
        450                 455                 460

Ala Ile His Ile
465
```

<210> SEQ ID NO 25
<211> LENGTH: 468
<212> TYPE: PRT
<213> ORGANISM: Gluconobacter oxydans

<400> SEQUENCE: 25

```
Met Cys Asp Thr Phe Asp Leu Ile Val Val Gly Gly Pro Gly Gly
1               5                   10                  15

Tyr Val Ala Ala Leu Arg Ala Ser Gln Leu Gly Met Ser Val Ala Leu
                20                  25                  30

Val Glu Ser Thr His Phe Gly Val Cys Leu Asn Trp Gly Cys Ile
            35                  40                  45

Pro Thr Lys Ala Leu Leu Arg Ser Ser Glu Ile His His Leu Leu His
    50                  55                  60

Glu Leu Gly Thr Phe Gly Leu Ser Ala Asp Asn Ile Ser Phe Asp Leu
65                  70                  75                  80

Ser Lys Ile Val Gly Arg Ser Arg Ser Ile Ala Arg Arg Met Gly Gly
                85                  90                  95

Gly Ile Ala His Leu Leu Lys Lys Thr Lys Val Thr Thr Phe Asp Gly
            100                 105                 110

Arg Ala Lys Leu Ala Gly Arg Ser Gly Glu Ala His Gln Val Ala Ile
        115                 120                 125

Thr Lys Asp Gly Ala Ala Val Ala Thr Ile Lys Ala Pro His Val Ile
130                 135                 140

Leu Ala Thr Gly Ala Arg Gly Arg Gln Leu Pro Gly Leu Glu Thr Asp
145                 150                 155                 160

Gly Thr Leu Ile Trp Gly Ala Arg Glu Ala Met Thr Pro Lys Glu Leu
                165                 170                 175

Pro Lys Arg Leu Leu Val Ile Gly Ser Gly Ala Ile Gly Ile Glu Phe
            180                 185                 190

Ala Ser Phe Tyr Arg Asn Met Gly Ser Glu Val Thr Ile Ala Glu Val
        195                 200                 205

Ala Asp Arg Ile Leu Ile Ala Glu Asp Pro Glu Ile Ser Ala Ala Ala
    210                 215                 220

Arg Lys Ala Phe Glu Lys Gln Gly Met Lys Ile Ile Thr Ser Ala Lys
225                 230                 235                 240

Val Gly Pro Leu Asn Lys Gly Glu Asn Glu Val Ser Thr Thr Ile Glu
                245                 250                 255

Ser Pro Thr Gly Lys Val Asp Leu Thr Val Asp Arg Val Ile Cys Ala
            260                 265                 270

Val Gly Ile Val Gly Asn Val Glu Asp Leu Gly Leu Glu Gly Thr Lys
        275                 280                 285
```

```
Val Gln Val Glu Arg Thr His Ile Val Thr Asp Gly Phe Cys Arg Thr
        290                 295                 300

Gly Glu Pro Gly Ile Tyr Ala Ile Gly Asp Val Ala Gly Ala Pro Trp
305                 310                 315                 320

Leu Ala His Lys Ala Ser His Glu Gly Ile Leu Cys Val Glu Lys Ile
                325                 330                 335

Ala Gly Arg Ser Pro Gln Pro Leu His Pro Leu Asn Ile Pro Gly Cys
                340                 345                 350

Thr Tyr Ser Arg Pro Gln Ile Ala Ser Val Gly Leu Ser Glu Glu Lys
            355                 360                 365

Ala Ile Ala Ala Gly His Lys Val Lys Val Gly Arg Phe Pro Phe Ile
370                 375                 380

Ala Asn Gly Lys Ala Val Ala Met Gly Glu Thr Asp Gly Met Val Lys
385                 390                 395                 400

Thr Val Phe Asp Ala Thr Ser Gly Glu Leu Leu Gly Ala His Met Ile
                405                 410                 415

Gly Ala Glu Val Thr Glu Met Ile Gln Gly Tyr Val Ile Thr Arg Thr
            420                 425                 430

Gly Glu Leu Thr Glu Ala Glu Leu Val Glu Thr Val Phe Pro His Pro
        435                 440                 445

Thr Ile Ser Glu Thr Met His Glu Ala Thr Leu Ala Ala Phe Asp Gly
    450                 455                 460

Pro Leu His Ile
465

<210> SEQ ID NO 26
<211> LENGTH: 469
<212> TYPE: PRT
<213> ORGANISM: Corynebacterium glutamicum

<400> SEQUENCE: 26

Met Thr Glu His Tyr Asp Val Val Leu Gly Ala Gly Pro Gly Gly
1               5                   10                  15

Tyr Val Ser Ala Ile Arg Ala Ala Gln Leu Gly Lys Lys Val Ala Val
            20                  25                  30

Ile Glu Lys Gln Tyr Trp Gly Gly Val Cys Leu Asn Val Gly Cys Ile
        35                  40                  45

Pro Ser Lys Ser Leu Ile Lys Asn Ala Glu Val Ala His Thr Phe Thr
    50                  55                  60

His Glu Lys Lys Thr Phe Gly Ile Asn Gly Glu Val Thr Phe Asn Tyr
65                  70                  75                  80

Glu Asp Ala His Lys Arg Ser Arg Gly Val Ser Asp Lys Ile Val Gly
                85                  90                  95

Gly Val His Tyr Leu Met Lys Lys Asn Lys Ile Ile Glu Ile His Gly
            100                 105                 110

Leu Gly Asn Phe Lys Asp Ala Lys Thr Leu Glu Val Thr Asp Gly Lys
        115                 120                 125

Asp Ala Gly Lys Thr Ile Thr Phe Asp Cys Ile Ile Ala Thr Gly
    130                 135                 140

Ser Val Val Asn Thr Leu Arg Gly Val Asp Phe Ser Glu Asn Val Val
145                 150                 155                 160

Ser Phe Glu Glu Gln Ile Leu Asn Pro Val Ala Pro Lys Lys Met Val
                165                 170                 175

Ile Val Gly Ala Gly Ala Ile Gly Met Glu Phe Ala Tyr Val Leu Gly
            180                 185                 190
```

```
Asn Tyr Gly Val Asp Val Thr Val Ile Glu Phe Met Asp Arg Val Leu
            195                 200                 205

Pro Asn Glu Asp Ala Glu Val Ser Lys Val Ile Ala Lys Ala Tyr Lys
210                 215                 220

Lys Met Gly Val Lys Leu Leu Pro Gly His Ala Thr Thr Ala Val Arg
225                 230                 235                 240

Asp Asn Gly Asp Phe Val Glu Val Asp Tyr Gln Lys Lys Gly Ser Asp
                245                 250                 255

Lys Thr Glu Thr Leu Thr Val Asp Arg Val Met Val Ser Val Gly Phe
            260                 265                 270

Arg Pro Arg Val Glu Gly Phe Gly Leu Glu Asn Thr Val Lys Leu
            275                 280                 285

Thr Glu Arg Gly Ala Ile Glu Ile Asp Tyr Met Arg Thr Asn Val
290                 295                 300

Asp Gly Ile Tyr Ala Ile Gly Asp Val Thr Ala Lys Leu Gln Leu Ala
305                 310                 315                 320

His Val Ala Glu Ala Gln Gly Ile Val Ala Ala Glu Thr Ile Ala Gly
                325                 330                 335

Ala Glu Thr Gln Thr Leu Gly Asp Tyr Met Met Met Pro Arg Ala Thr
            340                 345                 350

Phe Cys Asn Pro Gln Val Ser Ser Phe Gly Tyr Thr Glu Glu Gln Ala
            355                 360                 365

Lys Glu Lys Trp Pro Asp Arg Glu Ile Lys Val Ala Ser Phe Pro Phe
370                 375                 380

Ser Ala Asn Gly Lys Ala Val Gly Leu Ala Glu Thr Ser Gly Phe Ala
385                 390                 395                 400

Lys Ile Val Ala Asp Ala Glu Phe Gly Glu Leu Leu Gly Ala His Leu
                405                 410                 415

Val Gly Ala Asn Ala Ser Glu Leu Ile Asn Glu Leu Val Leu Ala Gln
            420                 425                 430

Asn Trp Asp Leu Thr Thr Glu Glu Ile Ser Arg Ser Val His Ile His
            435                 440                 445

Pro Thr Leu Ser Glu Ala Val Lys Glu Ala Ala His Gly Ile Ser Gly
    450                 455                 460

His Met Ile Asn Phe
465

<210> SEQ ID NO 27
<211> LENGTH: 471
<212> TYPE: PRT
<213> ORGANISM: Lactobacillus casei

<400> SEQUENCE: 27

Met Thr Met Asn Thr Asp Leu Val Val Leu Gly Gly Gly Pro Gly Gly
1               5                   10                  15

Tyr Val Ala Ala Ile Arg Ala Ala Gln Leu Gly Met Gln Val Val Leu
                20                  25                  30

Val Glu Lys Ala Lys Val Gly Gly Ile Cys Leu His Lys Gly Cys Ile
            35                  40                  45

Pro Thr Lys Ser Leu Leu His Ser Gly Glu Thr Leu Arg Leu Met Gln
        50                  55                  60

Ser Ala Ala Thr Phe Gly Gly Ile Ile Glu Gly Lys Val Gly Ile Asp
65                  70                  75                  80

Phe Ala Lys Ile Gln Ala Arg Lys Ala Thr Val Val Asp Gln Leu Tyr
                85                  90                  95
```

```
Arg Gly Val Gln Gly Leu Met Lys Lys Asn Lys Ile Thr Val Leu Asn
            100                 105                 110

Gly Thr Gly Ala Val Leu Gly Pro Ser Ile Phe Ser Pro Val Ser Gly
        115                 120                 125

Thr Val Ser Val Thr Phe Asp Asp Lys Ser Lys Glu Asp Val Met Ile
130                 135                 140

Val Pro Lys His Val Ile Ile Ala Thr Gly Ser Ser Pro Lys Thr Leu
145                 150                 155                 160

Pro Ser Leu Pro Ile Asp Glu Lys Met Ile Leu Thr Ser Asn Gly Met
                165                 170                 175

Leu Glu Leu Thr Ala Leu Pro Lys Lys Val Ala Ile Ile Gly Gly Gly
            180                 185                 190

Val Ile Gly Val Glu Trp Ala Ser Leu Leu Asn Asp Phe Gly Val Asp
        195                 200                 205

Val Thr Ile Val Glu Phe Leu Asp Gln Leu Val Ile Asn Glu Ser Gln
210                 215                 220

Thr Ile Ala Arg Glu Leu Gln Lys Gln Leu Glu Asn Arg Gly Ile His
225                 230                 235                 240

Ile Gln Leu Gly Ala Lys Val Glu Gln Ala Thr Ile Lys Asn Lys Gln
                245                 250                 255

Val Ala Leu Thr Ile Ala Glu Gln Ser Asp Pro Leu Ile Val Asp Lys
            260                 265                 270

Val Met Val Ala Ile Gly Arg Gln Pro Asn Val Glu Gly Ile Gly Leu
        275                 280                 285

Gln Asn Thr Ser Ile Lys Tyr Ser Ala Lys Gly Ile Thr His Asn Ala
290                 295                 300

Phe Tyr Gln Thr Thr Glu Asp His Ile Tyr Ala Ile Gly Asp Val Ile
305                 310                 315                 320

Asp Thr Leu Gln Leu Ala His Val Ala Met Lys Glu Gly Ile Ile Ala
                325                 330                 335

Val Glu His Met Ala Gly Leu Pro Val Ala Pro Leu Asn Tyr Asn Asp
            340                 345                 350

Val Pro Arg Cys Thr Tyr Thr Asp Pro Glu Ile Ala Ser Val Gly Tyr
        355                 360                 365

Thr Ser Ser Asn Tyr Pro Gln Asp Arg Asp Val Lys Ile Gly Arg Phe
370                 375                 380

Asn Phe Asn Ala Asn Ala Lys Ala Ile Ile Leu Gly Asp Thr Ala Gly
385                 390                 395                 400

Phe Val Glu Val Leu Arg Asp Val Ile Thr Asp Ile Ile Gly Val
                405                 410                 415

Ser Ile Ile Gly Ala His Ala Thr Asp Met Ile Ala Glu Met Ser Asp
            420                 425                 430

Ala Met Tyr Leu Asp Ala Ser Ala Thr Glu Ile Gly Asp Ala Val His
        435                 440                 445

Pro His Pro Ser Leu Ser Glu Ala Ile Gln Glu Ala Thr Leu Asp Thr
450                 455                 460

His Lys Ile Ala Ile His Lys
465                 470

<210> SEQ ID NO 28
<211> LENGTH: 486
<212> TYPE: PRT
<213> ORGANISM: Streptomyces coelicolor

<400> SEQUENCE: 28
```

-continued

```
Met Ser Gly Arg Thr Pro Ala Ala Asp Arg Ser Leu Glu Thr Gly Val
 1               5                  10                  15

Ala His Met His Gly Arg Asp Val Ala Asn Asp Ala Ser Thr Val
             20                  25                  30

Phe Asp Leu Val Ile Leu Gly Gly Ser Gly Gly Tyr Ala Ala Ala
         35                  40                  45

Leu Arg Gly Ala Gln Leu Gly Leu Asp Val Ala Leu Ile Glu Lys Asn
     50                  55                  60

Lys Leu Gly Gly Thr Cys Leu His Asn Gly Cys Ile Pro Thr Lys Ala
 65                  70                  75                  80

Leu Leu His Ala Gly Glu Val Ala Asp Gln Ser Arg Glu Ser Glu Gln
                 85                  90                  95

Phe Gly Val Lys Thr Ser Phe Glu Gly Val Asp Met Ala Gly Val His
             100                 105                 110

Lys Tyr Lys Asp Glu Val Ile Ala Gly Leu Tyr Lys Gly Leu Gln Gly
         115                 120                 125

Leu Val Ala Ser Arg Lys Ile Thr Tyr Ile Glu Gly Gly Arg Leu
     130                 135                 140

Ser Ser Pro Thr Ser Val Asp Val Asn Gly Gln Arg Val Gln Gly Arg
145                 150                 155                 160

His Val Leu Leu Ala Thr Gly Ser Val Pro Lys Thr Leu Pro Gly Leu
                 165                 170                 175

Glu Ile Asp Gly Asn Arg Ile Ile Ser Ser Asp His Ala Leu Thr Leu
             180                 185                 190

Asp Arg Val Pro Lys Ser Ala Ile Val Leu Gly Gly Gly Val Ile Gly
         195                 200                 205

Val Glu Phe Ala Ser Ala Trp Lys Ser Phe Gly Ser Glu Val Thr Val
     210                 215                 220

Ile Glu Gly Leu Lys His Leu Val Pro Val Glu Asp Glu Asn Ser Ser
225                 230                 235                 240

Lys Leu Leu Glu Arg Ala Phe Arg Lys Arg Gly Ile Lys Phe Asn Leu
                 245                 250                 255

Gly Thr Phe Phe Gln Lys Ala Glu Tyr Thr Gln Asp Gly Val Lys Val
             260                 265                 270

Thr Leu Ala Asp Gly Lys Glu Phe Glu Ala Glu Val Leu Leu Val Ala
         275                 280                 285

Ile Gly Arg Gly Pro Val Ser Gln Gly Leu Gly Tyr Glu Glu Asn Gly
     290                 295                 300

Val Ala Thr Asp Arg Gly Phe Val Leu Val Asp Glu Tyr Met Arg Thr
305                 310                 315                 320

Asn Val Pro Thr Ile Ser Ala Val Gly Asp Leu Val Pro Thr Leu Gln
                 325                 330                 335

Leu Ala His Val Gly Phe Ala Glu Gly Ile Leu Val Ala Glu Arg Leu
             340                 345                 350

Ala Gly Leu Lys Thr Val Pro Val Asp Tyr Asp Gly Val Pro Arg Val
         355                 360                 365

Thr Tyr Cys His Pro Glu Val Ala Ser Val Gly Leu Thr Glu Ala Arg
     370                 375                 380

Ala Lys Glu Val Tyr Gly Ala Asp Lys Val Val Ser Ile Lys Phe Pro
385                 390                 395                 400

Leu Gly Gly Asn Gly Lys Ser Arg Ile Leu Lys Thr Ala Gly Glu Ile
                 405                 410                 415

Lys Leu Val Gln Val Lys Asp Gly Ala Val Val Gly Val His Met Val
             420                 425                 430
```

Gly Asp Arg Met Gly Glu Gln Val Gly Glu Ala Gln Leu Ile Tyr Asn
435                 440                 445

Trp Glu Ala Leu Pro Ala Glu Val Ala Gln Leu Ile His Ala His Pro
450                 455                 460

Thr Gln Asn Glu Ala Leu Gly Glu Ala His Leu Ala Leu Ala Gly Lys
465                 470                 475                 480

Pro Leu His Met His Asp
            485

<210> SEQ ID NO 29
<211> LENGTH: 581
<212> TYPE: PRT
<213> ORGANISM: Streptococcus mutans

<400> SEQUENCE: 29

Met Ala Val Glu Ile Ile Met Pro Lys Leu Gly Val Asp Met Gln Glu
1               5                   10                  15

Gly Glu Ile Ile Glu Trp Lys Lys Gln Gly Asp Glu Val Lys Glu
            20                  25                  30

Gly Asp Ile Leu Leu Glu Ile Met Ser Asp Lys Thr Asn Met Glu Ile
            35                  40                  45

Glu Ala Glu Asp Ser Gly Val Leu Leu Lys Ile Val Lys Gly Asn Gly
    50                  55                  60

Gln Val Val Pro Val Thr Glu Val Ile Gly Tyr Ile Gly Ser Ala Gly
65                  70                  75                  80

Glu Thr Ile Glu Thr Asn Ala Ala Pro Ala Ser Ala Asp Asp Leu
                85                  90                  95

Lys Ala Ala Gly Leu Glu Val Pro Asp Thr Leu Gly Glu Ser Ala Ala
            100                 105                 110

Pro Ala Ala Gln Lys Thr Pro Leu Ala Asp Asp Glu Tyr Asp Met Ile
        115                 120                 125

Val Val Gly Gly Gly Pro Ala Gly Tyr Tyr Ala Ala Ile Arg Gly Ala
    130                 135                 140

Gln Leu Gly Gly Lys Val Ala Ile Val Glu Lys Ser Glu Phe Gly Gly
145                 150                 155                 160

Thr Cys Leu Asn Lys Gly Cys Ile Pro Thr Lys Thr Tyr Leu Lys Asn
                165                 170                 175

Ala Glu Ile Leu Asp Gly Ile Lys Ile Ala Ala Gly Arg Gly Ile Asn
            180                 185                 190

Phe Ala Ser Thr Asn Tyr Thr Ile Asp Met Asp Lys Thr Val Ala Phe
        195                 200                 205

Lys Asp Thr Val Val Lys Thr Leu Thr Ser Gly Val Gln Gly Leu Leu
    210                 215                 220

Lys Ala Asn Lys Val Thr Ile Phe Asn Gly Leu Gly Gln Val Asn Pro
225                 230                 235                 240

Asp Lys Thr Val Thr Val Gly Ser Glu Thr Ile Lys Gly His Asn Ile
                245                 250                 255

Ile Leu Ala Thr Gly Ser Lys Val Ser Arg Ile Asn Ile Pro Gly Ile
            260                 265                 270

Asp Ser Pro Leu Val Leu Thr Ser Asp Asp Ile Leu Asp Leu Arg Glu
        275                 280                 285

Ile Pro Lys Ser Leu Ala Val Met Gly Gly Gly Val Val Gly Ile Glu
    290                 295                 300

Leu Gly Leu Val Tyr Ala Ser Tyr Gly Thr Glu Val Thr Val Ile Glu
305                 310                 315                 320

Met Ala Asp Arg Ile Ile Pro Ala Met Asp Lys Glu Val Ser Leu Glu
                325                 330                 335

Leu Gln Lys Ile Leu Ser Lys Lys Gly Met Asn Ile Lys Thr Ser Val
                340                 345                 350

Gly Val Ala Glu Ile Val Glu Ala Asn Asn Gln Leu Thr Leu Lys Leu
                355                 360                 365

Asn Asp Gly Ser Glu Val Ala Glu Lys Ala Leu Leu Ser Ile Gly
                370                 375                 380

Arg Val Pro Gln Leu Ser Gly Leu Glu Asn Leu Asn Leu Glu Leu Glu
385                 390                 395                 400

Arg Gly Arg Ile Lys Val Asp Asp Tyr Gln Glu Thr Ser Ile Ser Gly
                405                 410                 415

Ile Tyr Ala Pro Gly Asp Val Asn Gly Arg Lys Met Leu Ala His Ala
                420                 425                 430

Ala Tyr Arg Met Gly Glu Val Ala Ala Glu Asn Ala Ile Trp Gly Asn
                435                 440                 445

Val Arg Lys Ala Asn Leu Lys Tyr Thr Pro Ala Ala Val Tyr Thr His
                450                 455                 460

Pro Glu Val Ala Met Cys Gly Ile Thr Glu Glu Gln Ala Arg Gln Glu
465                 470                 475                 480

Tyr Gly Asn Val Leu Val Gly Lys Ser Ser Phe Ser Gly Asn Gly Arg
                485                 490                 495

Ala Ile Ala Ser Asn Glu Ala Gln Gly Phe Val Lys Val Val Ala Asp
                500                 505                 510

Ala Lys Tyr His Glu Ile Leu Gly Val His Ile Ile Gly Pro Ala Ala
                515                 520                 525

Ala Glu Met Ile Asn Glu Ala Ser Thr Ile Met Glu Asn Glu Leu Thr
                530                 535                 540

Val Asp Glu Leu Leu Arg Ser Ile His Gly His Pro Thr Phe Ser Glu
545                 550                 555                 560

Val Met Tyr Glu Ala Phe Ala Asp Val Leu Gly Glu Ala Ile His Asn
                565                 570                 575

Pro Pro Lys Arg Arg
                580

<210> SEQ ID NO 30
<211> LENGTH: 476
<212> TYPE: PRT
<213> ORGANISM: Methanosarcina barkeri

<400> SEQUENCE: 30

Val Glu Asn Tyr Asp Leu Ile Ile Ile Gly Thr Gly Ser Ala Met Asn
1               5                   10                  15

Tyr Ile Asn Pro Ile Leu Asp Ser Asn Leu Lys Met Arg Val Ala Val
                20                  25                  30

Ile Asp Lys Asp Glu Pro Gly Gly Ile Cys Leu Thr Arg Gly Cys Ile
                35                  40                  45

Pro Ser Lys Ile Leu Leu Tyr Pro Ala Glu Leu Ile Arg Glu Ile Glu
            50                  55                  60

Thr Ala Ser Ile Phe Gly Ile Lys Leu Glu Ile Lys Asp Ile Asp Phe
65                  70                  75                  80

Leu Ala Ile Met Glu Arg Met Arg Arg Lys Ser Gly Glu Asp Ile Glu
                85                  90                  95

Ala Ile Arg Lys Ser Leu Thr Asp Asp Pro Tyr Leu Asp Tyr Tyr His
                100                 105                 110

```
Glu Ser Ala Glu Phe Ile Ser Pro Tyr Thr Leu Lys Val Gly Glu Lys
            115                 120                 125
Thr Leu His Ser Lys Met Ile Phe Leu Cys Thr Gly Ser Lys Pro Ala
            130                 135                 140
Ile Pro Thr Ile Lys Gly Leu Glu Glu Ala Gly Tyr Leu Thr Ser Asp
145                 150                 155                 160
Thr Val Leu Lys Leu Thr Glu Cys Pro Lys Lys Leu Ala Ile Leu Gly
            165                 170                 175
Gly Ser Tyr Ile Ala Ala Glu Tyr Gly Asn Phe Phe Ser Ala Ile Gly
            180                 185                 190
Ser Arg Val Thr Val Ile Gly Arg Asn Ser Gln Phe Leu Pro Gln Glu
            195                 200                 205
Glu Pro Glu Ile Ser Arg Leu Ala Ser Met Lys Met Ser Glu Tyr Met
            210                 215                 220
Gln Ile Ile Thr Asn His Glu Ala Ile Glu Val Arg Lys Glu Asp Asn
225                 230                 235                 240
Gly Gln Lys Thr Val Val Ala Arg Asn Lys Asn Ser Gly Lys Glu Val
            245                 250                 255
Lys Val Thr Val Asp Glu Val Leu Val Ala Thr Gly Arg Ala Pro Asn
            260                 265                 270
Thr Asp Ile Leu His Pro Asp Arg Ala Gly Ile Lys Thr Asp Thr His
            275                 280                 285
Gly Trp Ile Leu Val Asn Glu Phe Leu Glu Thr Ser Gln Pro Asn Ile
            290                 295                 300
Trp Ala Phe Gly Asp Ala Asn Gly Lys Tyr Leu Leu Lys His Val Ala
305                 310                 315                 320
Asn Tyr Glu Ser Gly Ile Val Tyr Leu Asn Ala Ile Leu Lys Glu Lys
            325                 330                 335
Ala Lys Ala Asp Tyr His Ala Val Pro His Ala Val Phe Ser Tyr Pro
            340                 345                 350
Glu Ile Ala Gly Val Gly Met Arg Glu Gln Glu Ala Val Glu Lys Tyr
            355                 360                 365
Gly Glu Glu Arg Ile Leu Ile Gly Leu Lys Phe Phe Glu Asp Thr Ala
            370                 375                 380
Lys Gly Ser Ala Met Glu Ile Arg Asp Tyr Phe Val Lys Val Ile Leu
385                 390                 395                 400
Asp Ser Glu Glu Glu Lys Ile Leu Gly Ala His Ile Ile Gly Pro His
                405                 410                 415
Ala Ser Val Leu Ile His Gln Ile Ile Pro Leu Met Tyr Thr Glu Ser
            420                 425                 430
Arg Ser Pro Glu Pro Ile Met Arg Gly Met Asp Ile His Pro Ser Leu
            435                 440                 445
Ser Glu Val Val Thr Arg Ala Phe Tyr Ser Arg Leu Pro Pro Glu His
            450                 455                 460
Tyr His His Phe Leu Lys His Ile Gly Leu Glu Asp
465                 470                 475
```